United States Patent
Koltai et al.

(10) Patent No.: US 12,303,541 B2
(45) Date of Patent: May 20, 2025

(54) ERODIUM CRASSIFOLIUM L'HER PLANT EXTRACTS AND USES THEREOF

(71) Applicants: THE STATE OF ISRAEL, MINISTRY OF AGRICULTURE & RURAL DEVELOPMENT, AGRICULTURAL RESEARCH, Rishon-LeZion (IL); THE ECONOMIC COMPANY FOR THE DEVELOPMENT OF RAMAT HANEGEV LTD., Ramat HaNegev (IL)

(72) Inventors: Hinanit Koltai, Rishon-LeZion (IL); Yoram Kapulnik, Karmey Yosef (IL); Marcelo Fridlender, Mazkeret Batia (IL); Einav Mayzlish Gati, Moshav Hemed (IL); Nasser Ahmed, Jerusalem (IL); Shemer Ben Zion, Moshav Kadesh Barnea (IL)

(73) Assignees: THE STATE OF ISRAEL, MINISTRY OF AGRICULTURE & RURAL DEVELOPMENT, AGRICULTURAL RESEARCH ORGANIZATION (ARO) (VOLCANI CENTER), Rishon-LeZion (IL); THE ECONOMIC COMPANY FOR THE DEVELOPMENT OF RAMAT HANEGEV LTD., Ramat HaNegev (IL)

( * ) Notice: Subject to any disclaimer, the term of this patent is extended or adjusted under 35 U.S.C. 154(b) by 931 days.

(21) Appl. No.: 17/215,329

(22) Filed: Mar. 29, 2021

(65) Prior Publication Data

US 2021/0290712 A1    Sep. 23, 2021

Related U.S. Application Data

(63) Continuation-in-part of application No. 15/563,595, filed as application No. PCT/IL2016/050348 on Mar. 31, 2016, now Pat. No. 10,960,035.

(60) Provisional application No. 62/141,313, filed on Apr. 1, 2015.

(51) Int. Cl.
| | |
|---|---|
| *A61K 36/185* | (2006.01) |
| *A23L 33/105* | (2016.01) |
| *A61K 31/192* | (2006.01) |
| *A61K 31/20* | (2006.01) |
| *A61K 31/353* | (2006.01) |
| *A61K 31/7004* | (2006.01) |

(52) U.S. Cl.
CPC .......... *A61K 36/185* (2013.01); *A23L 33/105* (2016.08); *A61K 31/192* (2013.01); *A61K 31/20* (2013.01); *A61K 31/353* (2013.01); *A61K 31/7004* (2013.01); *A61K 2236/333* (2013.01)

(58) Field of Classification Search
None
See application file for complete search history.

(56) References Cited

U.S. PATENT DOCUMENTS

| | | |
|---|---|---|
| 6,410,588 B1 | 6/2002 | Feldmann et al. |
| 6,949,582 B1 | 9/2005 | Wallace |
| 8,980,942 B2 | 3/2015 | Stinchcomb et al. |
| 2002/0132021 A1 | 9/2002 | Raskin et al. |
| 2004/0175367 A1 | 9/2004 | Herlyn et al. |
| 2007/0032544 A1 | 2/2007 | Korthout et al. |
| 2009/0197941 A1 | 8/2009 | Guy et al. |
| 2010/0249223 A1 | 9/2010 | Di Marzo et al. |
| 2010/0286098 A1 | 11/2010 | Robson et al. |
| 2012/0128777 A1 | 5/2012 | Keck et al. |
| 2013/0059018 A1 | 3/2013 | Parolaro et al. |
| 2013/0122114 A1 | 5/2013 | Golan et al. |
| 2013/0224151 A1 | 8/2013 | Pearson et al. |
| 2014/0221469 A1 | 8/2014 | Ross et al. |
| 2015/0086653 A1 | 3/2015 | Parolaro et al. |
| 2015/0297654 A1 | 10/2015 | Speier |
| 2016/0106705 A1 | 4/2016 | Verzura et al. |
| 2017/0007540 A1 | 1/2017 | Gupta |

FOREIGN PATENT DOCUMENTS

| | | |
|---|---|---|
| CN | 101524405 A | 9/2009 |
| CN | 101904881 A | 12/2010 |
| EP | 2298283 A2 | 3/2011 |
| GB | 2393721 A | 4/2004 |
| WO | 03061563 A2 | 7/2003 |
| WO | 2009004302 A1 | 1/2009 |
| WO | 2011051947 A1 | 5/2011 |
| WO | 2014159688 A1 | 10/2014 |
| WO | 2016103254 A1 | 6/2016 |
| WO | 2016157192 A1 | 10/2016 |
| WO | 2016189525 A1 | 12/2016 |
| WO | 2017013661 A1 | 1/2017 |

(Continued)

OTHER PUBLICATIONS

Communication Pursuant to Article 94(3) EPC Dated Jan. 29, 2020 From the European Patent Office Re. Application No. 16771541.6. (5 Pages).

(Continued)

*Primary Examiner* — Susan Hoffman
(74) *Attorney, Agent, or Firm* — The Roy Gross Law Firm, LLC; Roy Gross

(57) ABSTRACT

The present invention is directed to a composition consisting essentially of epigallocatechin, mannofuranose, α-D-xylopyranose, gallic acid, palmitic acid, stearic acid, trans-catechin, cis-catechin, and an acceptable carrier, and a method of using same, such as for treating an inflammatory disease.

21 Claims, 26 Drawing Sheets
Specification includes a Sequence Listing.

(56) References Cited

FOREIGN PATENT DOCUMENTS

| WO | 2017158609 A1 | 9/2017 |
|---|---|---|
| WO | 2018/163163 A1 | 9/2018 |
| WO | 2018/163164 A1 | 9/2018 |

OTHER PUBLICATIONS

Office Action Dated Jan. 20, 2020 From the Israel Patent Office Re. Application No. 254823. (3 Pages).
International Preliminary Report on Patentability Dated Sep. 19, 2019 From the International Bureau of WIPO Re. Application No. PCT/IL2018/050248. (10 Pages).
International Preliminary Report on Patentability Dated Sep. 19, 2019 From the International Bureau of WIPO Re. Application No. PCT/IL2018/050249. (10 Pages).
Supplementary European Search Report and the European Search Opinion Dated Nov. 6, 2018 From the European Patent Office Re. Application No. 16771541.6. (8 Pages).
Perera et al. "Immunomodulatory Activity of A Chinese Herbal Drug Yi Shen Juan Bi in Adjuvant Arthritis", Indian Journal of Pharmacology, XP055517710, 42(2): 65-69, Apr. 2010.
International Preliminary Report on Patentability Dated Sep. 27, 2018 From the International Bureau of WIPO Re. Application No. PCT/IL2017/050338. (7 Pages).
International Search Report and the Written Opinion Dated Jun. 7, 2018 From the International Searching Authority Re. Application No. PCT/ 1L2018/050248. (15 Pages).
International Search Report and the Written Opinion Dated Jun. 17, 2018 From the International Searching Authority Re. Application No. PCT/1L2018/050249. (13 Pages).
Aizpurua-Olaizola et al. "Evolution of the Cannabinoid and Terpene Content During the Growth of Cannabis Sativa Plants From Different Chemotypes", Journal of Natural Products, 79(2): 324-331, Feb. 2, 2016.
Aviello et al. "Chemopreventive Effect of the Non-Psychotropic Phytocannabinoid Cannabidiol on Experimental Colon Cancer", Journal of Molecular Medicine, 90(8): 925-934, Published Online Jan. 10, 2012.
Ben-Shabat et al. "An Entourage Effect: Inactive Endogenous Fatty Acid Glycerol Esters Enhance 2-Arachidonoyl-Glycerol Cannabinoid Activity", European Journal of Pharmacology, 353(1): 23-31, Jul. 17, 1998.
Borrelli et al. "Colon Carcinogenesis Is Inhibited by the TRPM8 Antagonist Cannabigerol, A Cannabis-Derived Non-Psychotropic Cannabinoid", Carcinogenesis, 35(12): 2787-2797, Advance Access Publication Sep. 30, 2014.
D'Haens et al. "Future Directions in Inflammatory Bowel Disease Management", Journal ofCrohn's and Colitis, 8(8): 726-734, Aug. 2014.
ElSohly et al. "Phytochemistry of *Cannabis sativa* L.", Progress in the Chemistry of Organic Natural Products: Phytocannabinoids, Pogrchem, 103: 1-36, Published Online Jan. 25, 2017.
Greenhough et al. "The Cannabinoid [Delta]9-Tetrahydrocannabinol Inhibits RAS-MAPK and P13K-AKT Survival Signalling and Induces BAD-Mediated Apoptosis in Colorectal Cancer Cells", International Journal of Cancer, 121 ( 10): 2172-2180, Published Online Jun. 21, 2007.
Greineisen et al. "Immunoactive Effects of Cannabinoids: Considerations for the Therapeutic Use of Cannabinoid Receptor Agonists and Antagonists", International Immunopharmacology, 10(5): 547-555, May 2010.
Hill et al. "Cannabidivarin-Rich Cannabis Extracts Are Anticonvulsant in Mouse and Rat Via A CBI Receptor-Independent Mechanism", British Journal of Pharmacology, 170(3): 679-692, Oct. 2013.
Ihenetu et al. "Inhibition of Interleukin-8 Release in the Human Colonic Epithelial Cell Line HT-29 by Cannabinoids", European Journal of Pharmacology, 458( 1-2): 207-215, Jan. 2003.
Izzo et al. "Cannabinoids Is An Intestinal Inflammation and Cancer", Pharmacological Research, 60(2): 117-125, Aug. 2009.
Javid et al. "Cannabinoid Pharmacology in Cancer Research: A New Hope for Cancer Patients?", European Journal of Pharmacology, 775: 1-4, Mar. 15, 2016.
Mechoulam et al. "Cannabidiol: An Overview of Some Pharmacological Aspects", The Journal of Clinical Pharmacology, 42(S 1): 11S-19S, Nov. 2002.
Mechoulam et al. "Chemical Basis of Hashish Activity", Science, 169(3945): 611-612, Aug. 7, 1970.
Mechoulam et al. "Hashish-IV: The Isolation and Structure of Cannabinolic Cannabidiolic and Cannabigerolic Acids", Tetrahedron, 21(5): 1223-1229, Jan. 1965.
Naftali et al. "Cannabis Induces A Clinical Response in Patients With Crohn's Disease: A Prospective Placebo-Controlled Study", Clinical Gastroenterology and Hepatology, 11(10): 1276-1280, Oct. 2013.
Naftali et al. "Treatment of Crohn's Disease With Cannabis: An Observational Study", The Israel Medical Association Journal, IMAJ, 13(8): 455-458, Aug. 2011.
Pagano et al. "An Orally Active Cannabis Extract With High Content in Cannabidiol Attenuates Chemically-Induced Intestinal Inflammation and Hypermotility in the Mouse", Frontiers in Pharmacology, 7(Art.341): 1-12, Oct. 4, 2016.
Romano et al. "Inhibition of Colon Carcinogenesis by A Standarized Cannabis Sativa Extract With High Content of Cannabidiol", Phytomedicine, 21(5): 631-639, Apr. 15, 2014.
Romano et al. "Pure [Delta]9-Tetrahydrocannabivarin and A Cannabis Sativa Extract With High Content in [Delta]9- Tetrahydrocannabivarin Inhibit Nitrite Production in Murine Peritoneal Macrophages", Pharmacological Research, 113: 199-208, Available Online Aug. 3, 2016.
Russo et al. "Taming THC: Potential Cannabis Synergy and Phytocannabinoid-Terpenoid Entourage Effects", British Journal of Pharmacology, 163(7): 1344-1364, Aug. 2011.
Ryberg et al. "The Orphan Receptor GPR55 Is A Novel Cannabinoid Receptor", British Journal of Pharmacology, 152(7): 1092-1101, Published Online Sep. 17, 2007.
Sartor "Mechanisms of Disease: Pathogenesis of Crohn's Disease and Ulcerative Colitis", Nature Clinical Practice Gastroenterology & Hepatology, 3(7): 390-407, Jul. 2006.
Schicho et al. "Cannabis Finds Its Way Into Treatment of Crohn's Disease", Pharmacology, 93(1-2): 1-3, Published Online Dec. 17, 2013.
Stancic et al. "The GPR55 Antagonist CID16020046 Protects Against Intestinal Inflammation", Neurogastroenterology & Motility, 27(10): 1432-1445, Oct. 2015.
Storr et al. "Activation of the Cannabinoid 2 Receptor (CB2) Protects Against Experimental Colitis", Inflammation Bowel Disease, 15(11): 1678-1685, Published Online Apr. 30, 2009.
Sturm et al. "Epithelial Restitution and Wound Healing in Inflammatory Bowel Disease", World Journal of Gastroenterology, 14(3): 348-353, Jan. 21, 2008.
Wright et al. "Cannabinoid CB2 Receptors in the Gastrointestinal Tract: A Regulatory System in States of Inflammation", British Journal of Pharniacology, 153(2): 263-270, Published Online Oct. 1, 2007.
Hynds (Disease Models and Mechanisms (2018), vol. 11, p. 1-5).
International Preliminary Report on Patentability Dated Oct. 31, 2017 From the International Bureau of WIPO Re. Application No. PCT/IL2016/050348. (7 Pages).
International Search Report and the Written Opinion Dated Jul. 7, 2016 From the International Searching Authority Re. Application No. PCT/IL2016/050348. (7 pages).
International Search Report and the Written Opinion Dated Jun. 26, 2017 From the International Searching Authority Re. Application No. PCT/IL2017/050338. (10 Pages).
Colbert "Cannabinoid Profile: Tetrahydrocannabinolic Acid (THCa)", TheLeafOnline, 5 P., Jul. 15, 2014.
Sroka et al. "Antioxidative Effect of Extracts From *Erodium cicutarium* L.", Zeitung fuer Naturforschung, 49(11-12): 881-884, Nov.-Dec. 1994.
De Filippis et al. "Cannabidiol Reduces Intestinal Inflammation Through the Control of Neuroimmune Axis", PLoS One, 6(12): e28159-1-e28159-9, Dec. 6, 2011. Figs.5-8.

(56) References Cited

OTHER PUBLICATIONS

De Graaf et al. "Preparation and Incubation of Precision-Cut Liver and Intestinal Slices for Application in Drug Metabolism and Toxicity Studies", Nature Protocols, 5(9): 1540-1551, Published Online Aug. 19, 2010.

De Kanter et al. "Precision-Cut Organ Slices as A Tool to Study Toxicity and Metabolism of Xenobiotics With Special Reference to Non-Hepatic Tissues", Current Drug Metabolism, 3(1): 39-59, Feb. 2002.

Evans et al. "The Development of A Method for the Preparation of Rat Intestinal Epithelial Cell Primary Cultures", Journal of Cell Science, 101: 219-231, Jan. 31, 1992. Abstract, Figs. I, 2, Table 1, p. 222, Left col. Para 5, p. 228, Left col. 1st Para.

Gohar et al. "Antibacterial Polyphenol From Erodium Glaucophyllum", Zeitung fuer Naturforschung, 58(9-10): 670-674, Sep.-Oct. 2003. p. 670, 672-673.

Harvey et al. "Interleukin 17 A Evoked Mucosal Damage Is Attenuated by Cannabidiol and Anandamide in A Human Colonic Explant Model", Cytokine, 65(2): 236-244, Available Online Nov. 13, 2013. p. 239, Left col. 1st Para, p. 243, Left col. 3rd Para, Figs. I, 2.

Sato et al. "Long-Term Expansion of Epithelial Organoids From Human Colon, Adenoma, Adenocarcinoma, and Barrett's Epithelium", Gastroenterology, 141: 1762-1772, Sep. 2, 2011. p. 1763, Left col. 5th Para, Right col. Para 1-2, p. 1764, Right col. 3rd Para, p. 1765, Left col. 2nd Para, Fig. 1.

Gillet (J Natl Cancer Inst (2013), vol. 105, pp. 452-458).

MatTek Corporation "Epiintestina1n1", Overiew, MatTek Corporation, 8 P., 2017.

Danin "Erodimn Crassifolium, Erodium Hirtmn, Hoary-Leaved Heron's-Bill", Flowers of Israel, Retrieved From the Internet, p. 1-3, Aug. 8, 2014.

Korbecki J, Bajdak-Rusinek K. The effect of palmitic acid on inflammatory response in macrophages: an overview of molecular mechanisms. Inflamm Res. Nov. 2019;68(11):915-932. doi: 10.1007/s00011-019-01273-5. Epub Jul. 30, 2019. PMID: 31363792; PMCID: PMC6813288.

Miao H, Chen L, Hao L, Zhang X, Chen Y, Ruan Z, Liang H. Stearic acid induces proinflammatory cytokine production partly through activation of lactate-HIF1α pathway in chondrocytes. Sci Rep. Aug. 14, 2015;5:13092. doi: 10.1038/srep13092. PMID: 26271607; PMCID: PMC4536527.

Sivasubramanian MK, Monteiro R, Jagadeesh M, Balasubramanian P, Subramanian M. Palmitic Acid Induces Oxidative Stress and Senescence in Human Brainstem Astrocytes, Downregulating Glutamate Reuptake Transporters-Implications for Obesity-Related Sympathoexcitation. Nutrients. Aug. 26, 2024; 16(17):2852. doi: 10.3390/nu16172852. PMID: 39275168; PMCID: PMC11397225.

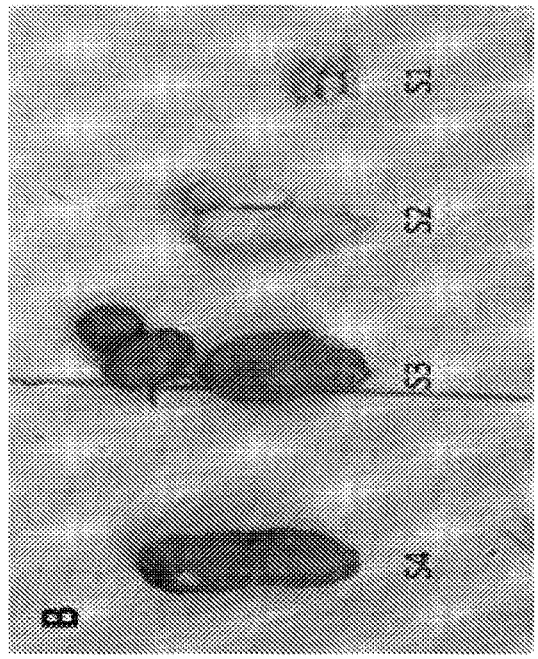
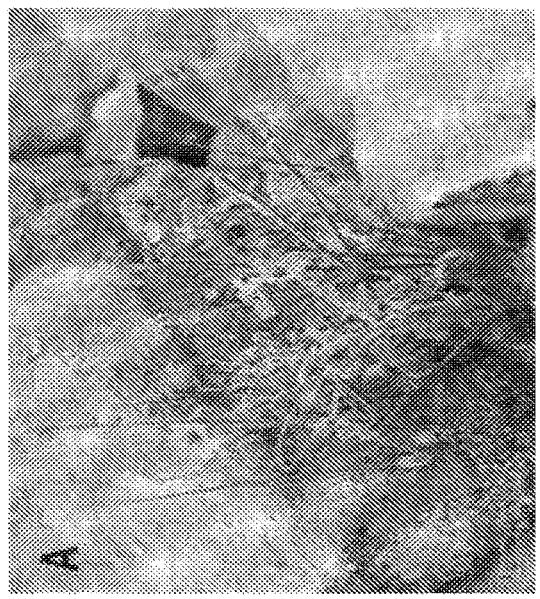
FIG. 1B
FIG. 1A

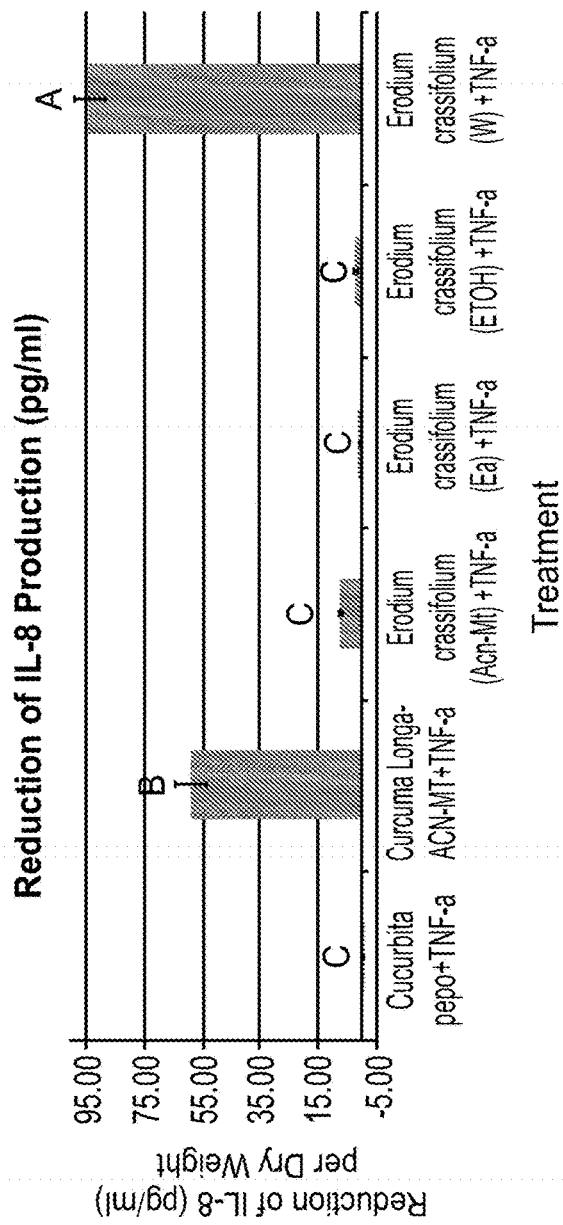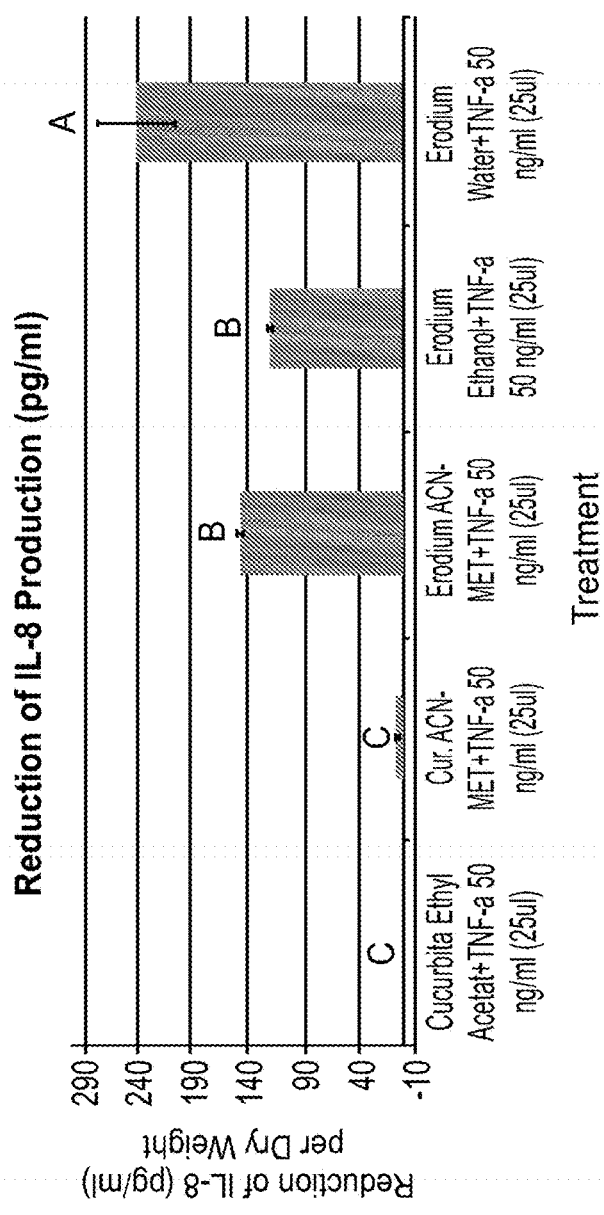
FIG. 3A
FIG. 3B

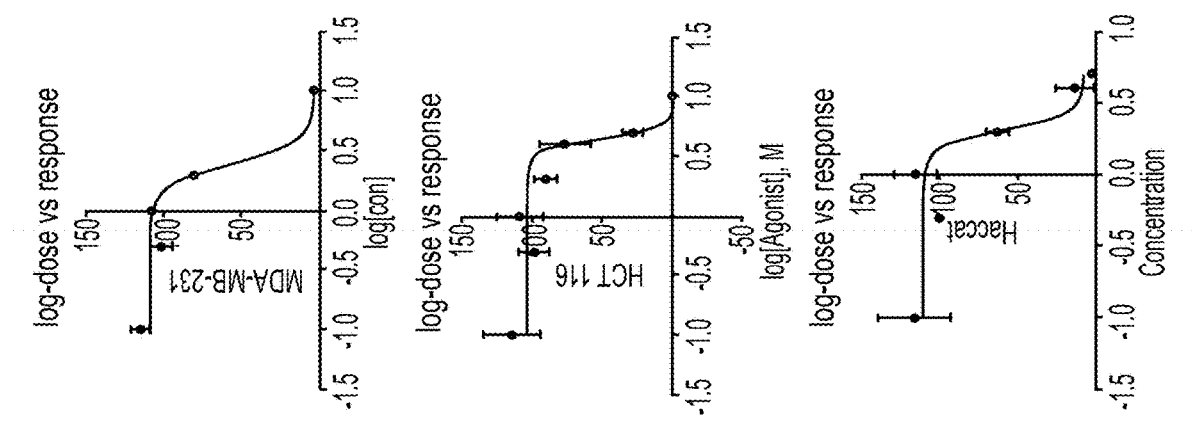
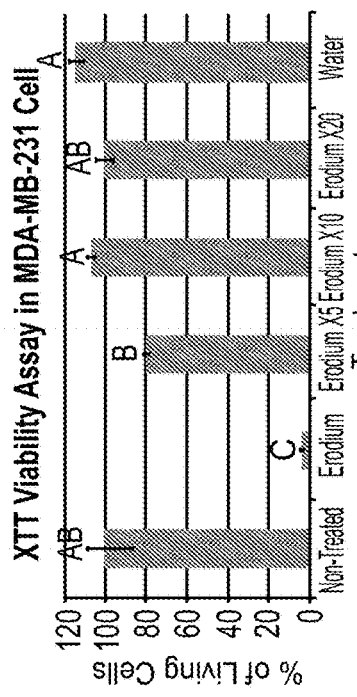
FIG. 4A
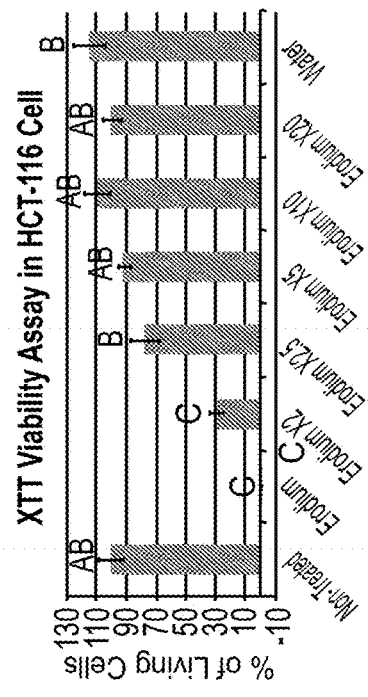
FIG. 4B
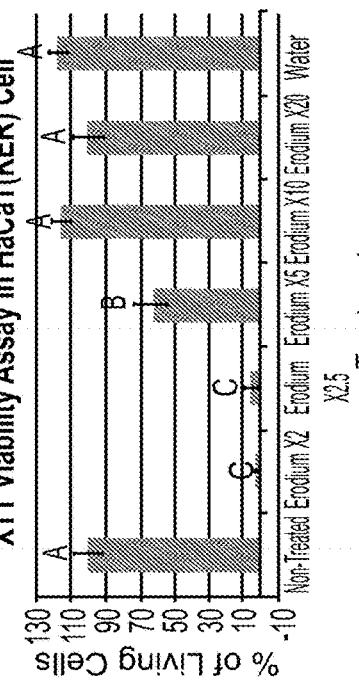
FIG. 4C

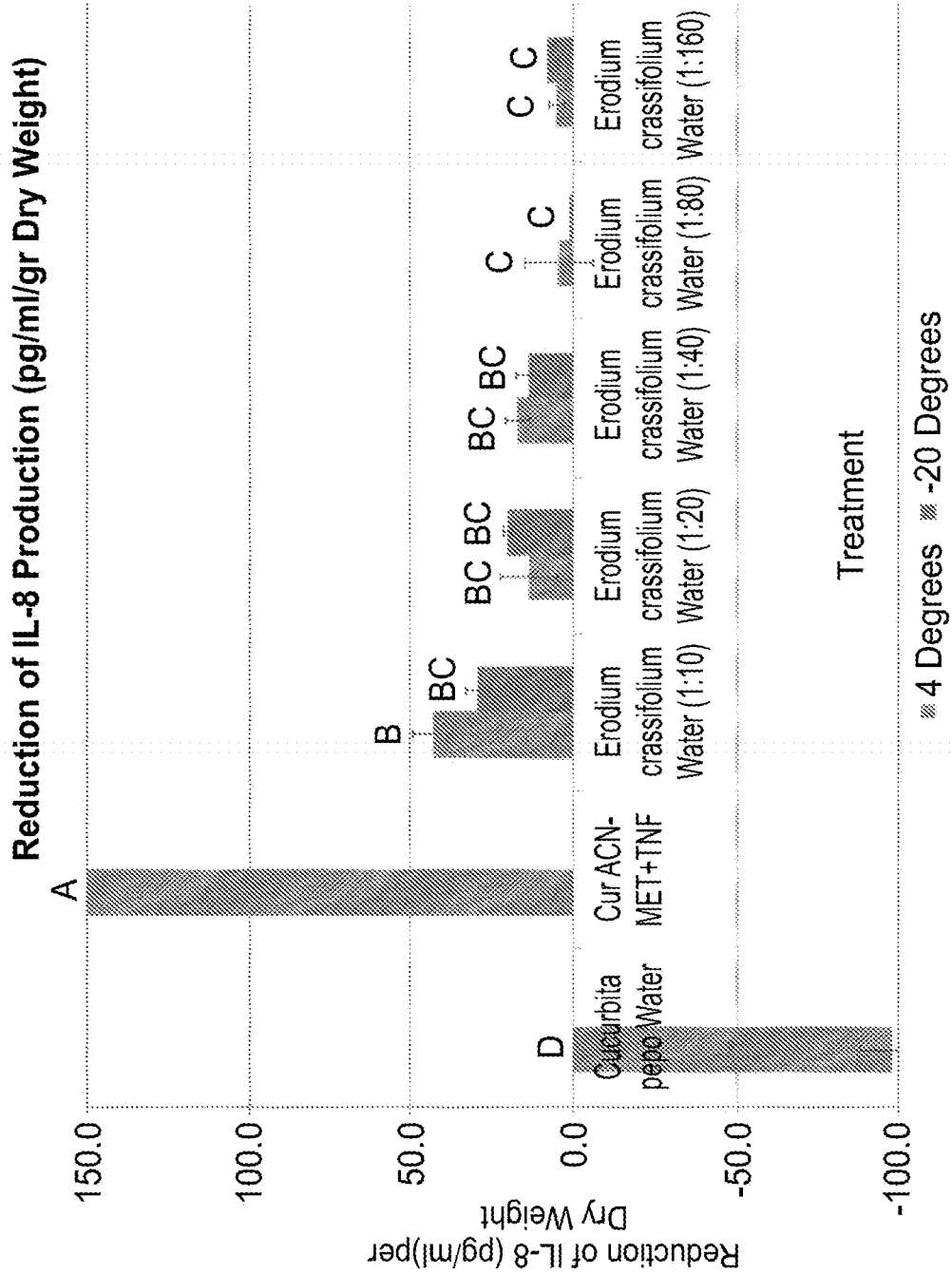

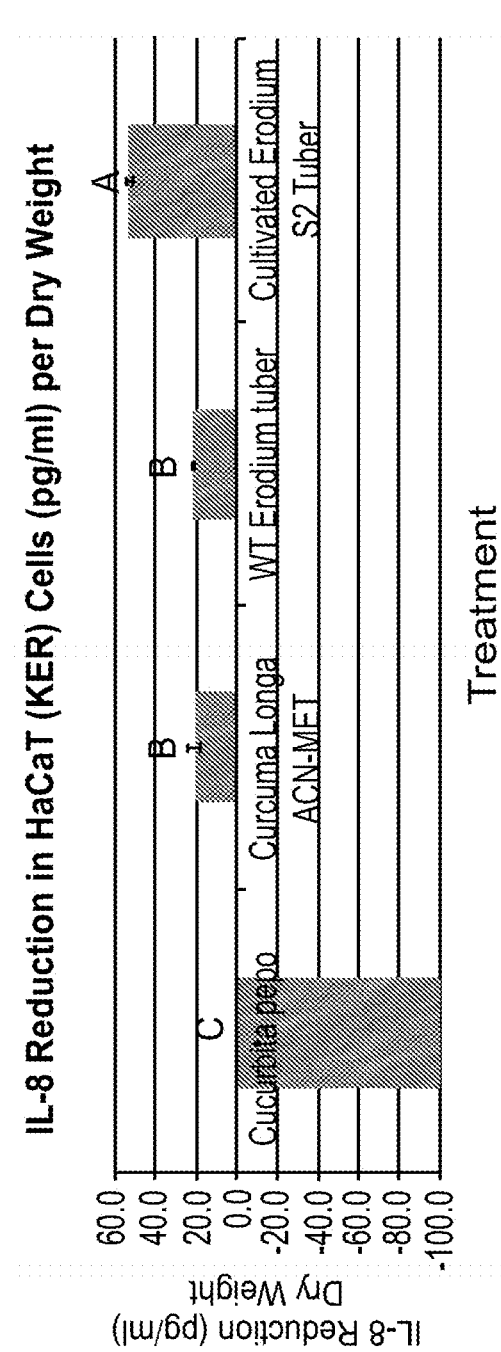
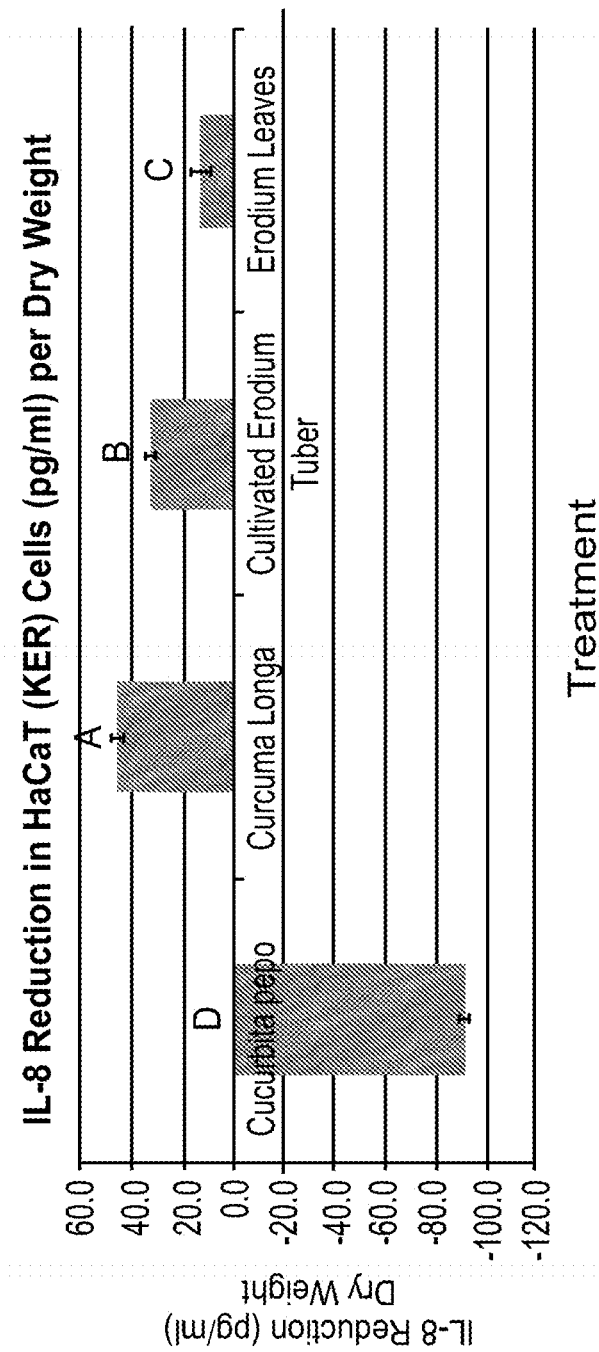
FIG. 10A
FIG. 10B

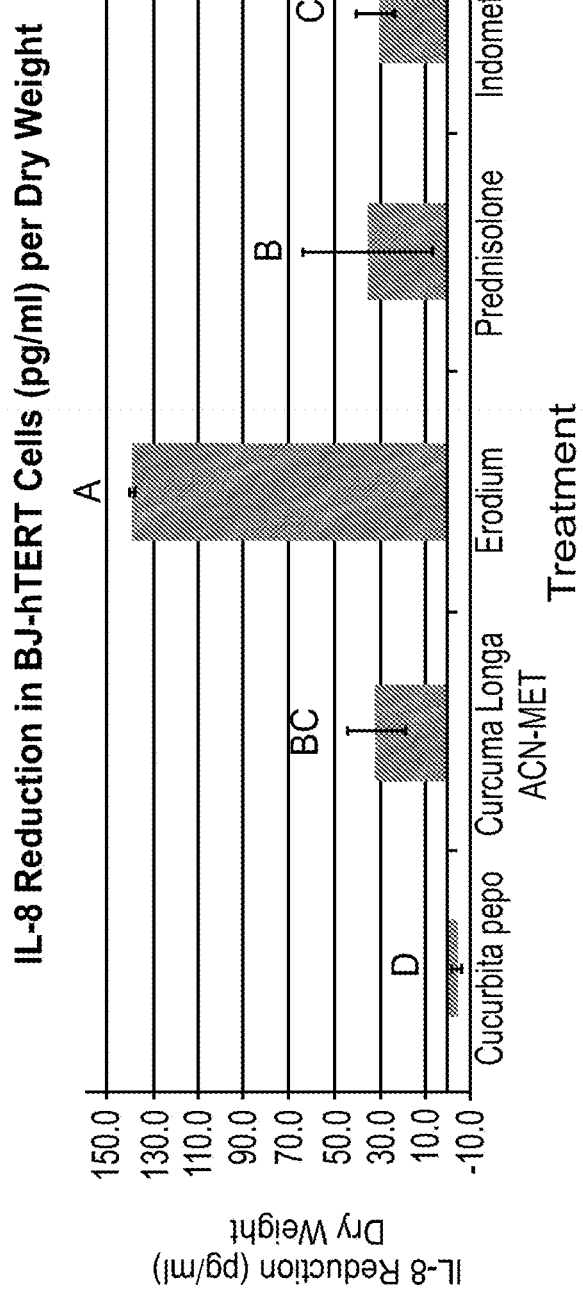
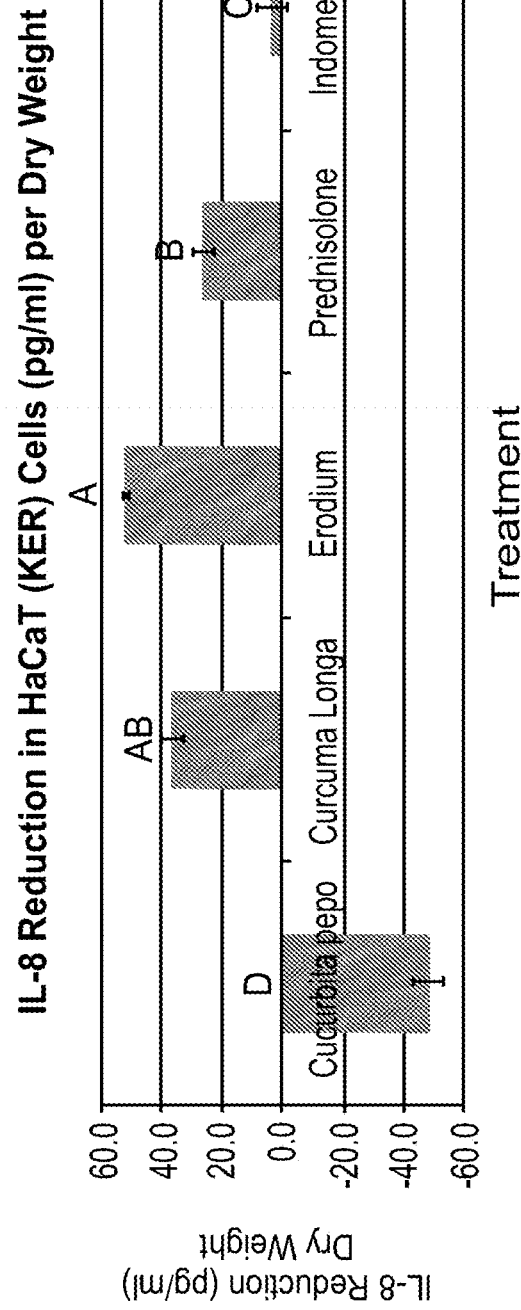
FIG. 11A
FIG. 11B

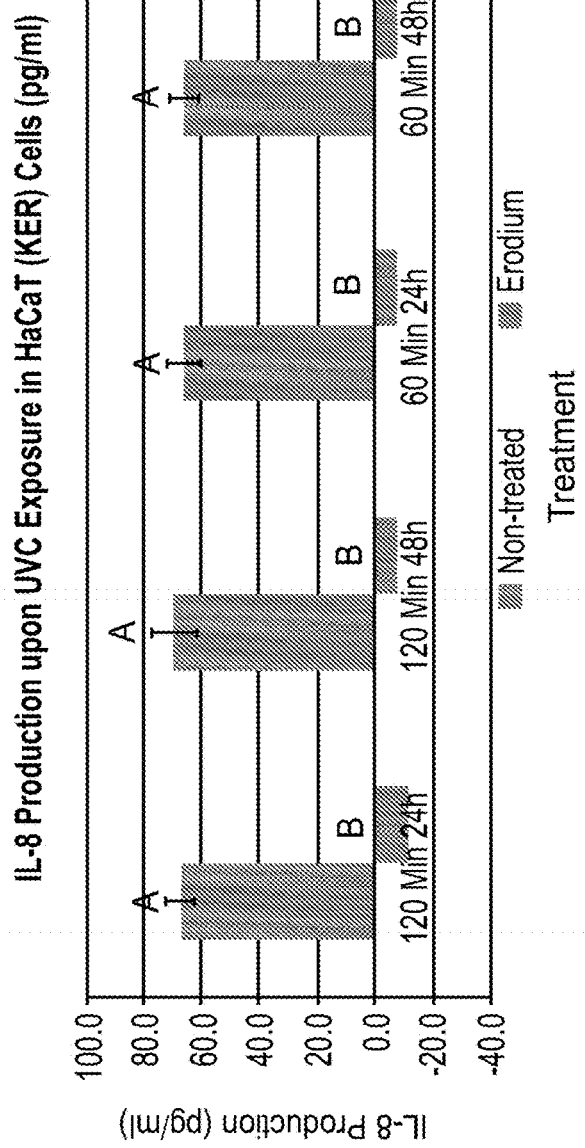
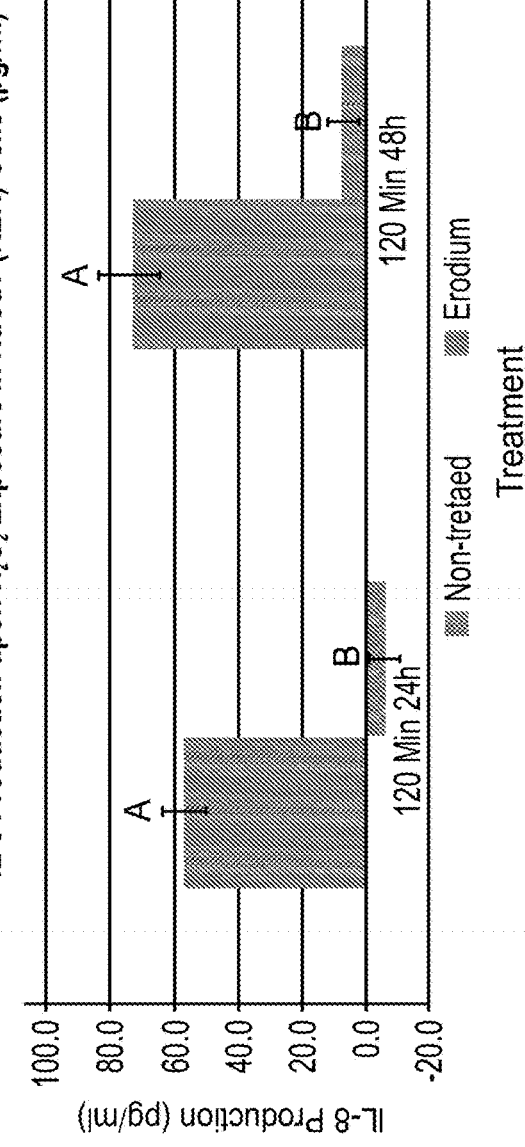
FIG. 15A
FIG. 15B

ERODIUM CRASSIFOLIUM L'HER PLANT EXTRACTS AND USES THEREOF

CROSS-REFERENCE TO RELATED APPLICATIONS

This application is also a continuation-in-part of U.S. patent application Ser. No. 15/563,595, filed Oct. 1, 2017, now U.S. Pat. No. 10,960,036, titled "ERODIUM CRASSIFOLIUM L'HER PLANT EXTRACTS AND USES THEREOF", which is a national phase of International Patent Application No. PCT/IL2016/050348, filed Mar. 31, 2016, titled "ERODIUM CRASSIFOLIUM L'HER PLANT EXTRACTS AND USES THEREOF", which claims the benefit of priority of U.S. Provisional Patent Application No. 62/141,313, filed Apr. 1, 2015, titled "DEVELOPMENT OF THERAPEUTIC/NUTRITIONAL PRODUCTS BASED ON ERODIUM CRASSIFOLIUM L'HER PLANT EXTRACTS".

The contents of all the above applications are incorporated herein by reference in their entirety.

FIELD OF THE INVENTION

The present invention, in some embodiments, relates to extracts of *Erodium* plants and, more particularly, but not exclusively, to polar extracts of tubers of *Erodium* plants.

BACKGROUND OF THE INVENTION

From an ethnobotanical perspective, many plants from the Geraniaceae family are considered to have medicinal value. In particular, some of the species belonging to the genus *Erodium* of this family have recognized medicinal applications known from folklore and empirical data. *Erodium* species are used to treat a variety of human ailments such as colds, coughs, diarrhea, hemorrhaging and are used to dress wounds. One of the species, *Erodium botrys* is known from the ethnobotanical explorations conducted by the British anthropologist Melville William Hilton-Simpson (1881-1938) as a traditional dressing for wounds.

*Erodium crassifolium* L'Her (Hairy storks bill) is a hemicryptophyte (i.e. buds at or near the soil surface). It develops tubers on its roots. It has a suffruticose branching stem and flowering branches which are erect, slender, reddish brown, and thickly clothed with unequal villous hairs. Its leaves are alternate, rosette, pinnated or deeply lacinated. The flowers of this plant are hermaphrodite; pink and violet. The plant habitat is shrub-steppes and desert (FIG. 1). *Erodium crassifolium* L'Her is common in the Negev Highlands of Israel, with less than 90 mm annual precipitation. The plant produces a small tuber in the ground about 20 cm deep. This organ serves as a water and nutrient reservoir enabling the plant to overcome the dry season (FIG. 1). It is traditionally known that the tubers are edible, used mainly by the Bedouin nomadic tribes. The tubers have a sweet taste and are best in late winter or early spring when they are whitish in color.

Traditional knowledge considers the tubers useful in the treatment of epilepsy and some skin disorders, including insect bites (http://www(dot)cretanflora(dot)com/*Erodium_crassifolium*(dot)html).

Due to the traditional uses of *E. crassifolium*, the inventors are interested in examining its anti-oxidant and anti-inflammatory activities in vitro on a skin model.

SUMMARY OF THE INVENTION

The present invention, in some embodiments, discloses the measuring of anti-inflammatory activity of *Erodium* extracts, by quantifying the level of interleukin-8 (IL-8), a pro-inflammatory chemokine involved in inflammation, including in skin diseases.

In some embodiments, the present invention is based, in part, on the finding the *E. crassifolium* tuber ethanol extract (EE) and its fractions, induced a significant in vitro anti-inflammatory activity on normal keratinocyte cell line (HaCaT). Further, the inventors have identified some of the active compounds, and accordingly, suggest that the EE in vitro anti-inflammatory activity may be attributed to a combination of these compounds.

According to a first aspect, there is provided a composition consisting essentially of: epigallocatechin, mannofuranose, α-D-xylopyranose, gallic acid, palmitic acid, stearic acid, trans-catechin, cis-catechin, and an acceptable carrier.

According to another aspect, there is provided a method for treating a subject afflicted with an inflammatory or a condition associated therewith, comprising administering to the subject a therapeutically effective amount of the composition of the invention.

In some embodiments, epigallocatechin is present in an amount of 35-50% (w/w) of the composition.

In some embodiments, mannofuranose is present in an amount of 15-22% (w/w) of the composition.

In some embodiments, α-D-xylopyranose is present in an amount of 1.5-3.5% (w/w) of the composition.

In some embodiments, gallic acid is present in an amount of 3-7% (w/w) of the composition.

In some embodiments, palmitic acid is present in an amount of 4-8% (w/w) of the composition.

In some embodiments, stearic acid is present in an amount of 0.5-3.5% (w/w) of the composition.

In some embodiments, trans-catechin is present in an amount of 8-15% (w/w) of the composition.

In some embodiments, cis-catechin is present in an amount of 7-16% (w/w) of the composition.

In some embodiments, any one of the: epigallocatechin, mannofuranose, α-D-xylopyranose, gallic acid, palmitic acid, stearic acid, trans-catechin, and cis-catechin, is derived from a polar extract of *Erodium* plant tuber.

In some embodiments, the polar solvent comprises 50-90% (v/v) ethanol.

In some embodiments, the *Erodium* plant is *Erodium crassifolium* L'Her.

In some embodiments, the composition is a pharmaceutical composition or a nutraceutical composition.

In some embodiments, the composition is suitable for topical administration or oral administration.

In some embodiments, the inflammatory disease comprises an inflammatory skin disease.

In some embodiments, the skin disease is selected from the group consisting of: a cutaneous disease, a dermal disease, a bullous skin disease, *Pemphigus vulgaris*, bullous pemphigoid, *Pemphigus foliaceus*, and any combination thereof.

In some embodiments, the inflammatory disease is induced by irradiation, oxidative stress, or both.

In some embodiments, treating comprises reducing the expression level, the activity, or both, of interleukin 8 (IL-8), matrix metalloprotease 3 (MMP3), MMP9, or any combination thereof, in said subject.

In some embodiments, the administering comprises: topically administering, orally administering, or both.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 1A-1B include photographs of *Erodium crassifolium* L'Her. (1A) A desert shrub. (1B) Different stages of tubers. S1-younger tubers; S4 older ones.

FIGS. 3A-3B include graphs illustrating the anti-inflammatory activity in different *Erodium crassifolium* extracts. (3A) Reduced IL-8 level in HCT-116 colon cells. (3B) Reduced IL-8 level in BJ-hTERT skin cells. Anti-inflammatory specific activity (pg/ml per 1 gr dry weight) was calculated as previously described. Means of replicates statistically analyzed by multiple comparison Tukey-Kramer test ($P \leq 0.05$). Levels not connected by same letter are significantly different. Ea=Ethyl acetate; W=Water; ACN-MET=Acetonitrile-Methanol (1:1); ETOH=ethanol.

FIGS. 4A-4C include graphs showing dose response curves of MDA-MB-231, HCT-116 and HaCaT (KER) exposed to different concentrations of *E. crassifolium* extracts. (4A) Viability assay using MDA-MB-231 cells. On the left XXT results and on the right log-dose vs. response curve from which IC50 was calculated. IC50=7.438. (4B) Viability assay using HCT-116 cells. IC50=13.55 (4C) Viability assay using HaCaT (KER) cells. IC50=6.132. *Erodium*=Non-diluted extract while *Erodium* X2, X2.5, X5, X10 and X20 are extracts diluted 2, 2.5. 5, 10 or 20 times.

FIG. 5 includes a graph illustrating the stability and dilution of *Erodium* extracts. Extracts were stored at either 4° C. or −20° C. for two weeks. The extracts were spun and filtered and stored at 4° C. until used. The ratios 1:10, 1:20, 1:40, 1:80 and 1:160 represent *Erodium* dilutions with water. Levels not connected by same letter are significantly different. ACN-MET=Acetonitrile-Methanol (1:1).

FIGS. 10A-10B include graphs illustrating the anti-inflammatory activity comprised in wild type (WT) tubers and leaves of *Erodium* plants. Activity was evaluated by IL-8 ELISA assay performed on HaCaT (KER) skin cells. (10A) Comparison of anti-inflammatory activity in WT tubers vs. cultivated tubers. (10B) Comparison of anti-inflammatory activity in tubers vs. leaves of cultivated plants. Levels not connected by same letter are significantly different. ACN-MET=Acetonitrile-Methanol (1:1).

FIGS. 11A-11B include graphs showing that *Erodium* water extracts can replace steroids and NSAIDs in inflammation treatment. Activity was evaluated by IL-8 ELISA assay performed in both BJ-hTERT (11A) and HaCaT (KER) skin cells (11B). Prednisolone and indomethacin working solutions were prepared as described in material and methods. Levels not connected by same letter are significantly different. ACN-MET=Acetonitrile-Methanol (1:1).

Each cytokine was tested using the appropriate ELISA kit. Two different extractions *Erodium* extracts (*Erodium* S2

10/6/15 and *Erodium* S2 24/6/15) were tested. (13A) Reduction of IL-6 levels. (13B) Reduction of IL-12 levels. (13C) Reduction of IL-27 levels. (13D) Reduction of IL-8 levels. This assay (IL-8) served as a control for all other ELISA assays. Levels not connected by same letter are significantly different.

FIGS. 14A-14D include graphs showing antioxidant activity found in *Erodium* water extracts. (14A) antioxidant activity of *Erodium* water extracts in HaCaT (KER) skin cells. Bars represent the specific activity calculated as the area (manufacturer instructions) under the curve for each treatment relatively to the antioxidant activity of the standard Trolox™ divided by the dried weight of each extract. (14B) Curves show the fluorescence unit obtained for non-treated (NT), Quercetin treated cells (blank) and cells treated with the *Erodium* extracts. (14C) and (14D) Assay in HaCaT (KER) skin cells (14C) and HCT-116 colon cells (14D). Bars represent specific activity calculated as the area (kit instructions) under the curve for each treatment relatively to the antioxidant activity of the standard Quercetin divided by the dried weight of each extract. Levels not connected by same letter are significantly different.

FIGS. 15A-15B include graphs illustrating the anti-UV and hydrogen peroxide induced inflammatory activity of *Erodium* water extracts. HaCaT (KER) skin cells were exposed for 24 h or 48 h to either UVC or hydrogen peroxide (H2O2) in the presence or absence of *Erodium* water extract. Anti-pollutant activity was measured using the IL-8 ELISA assay. (15A) Exposure to UVC. (15B) Exposure to hydrogen peroxide (H2O2). Levels not connected by same letter are significantly different.

Figure 16:
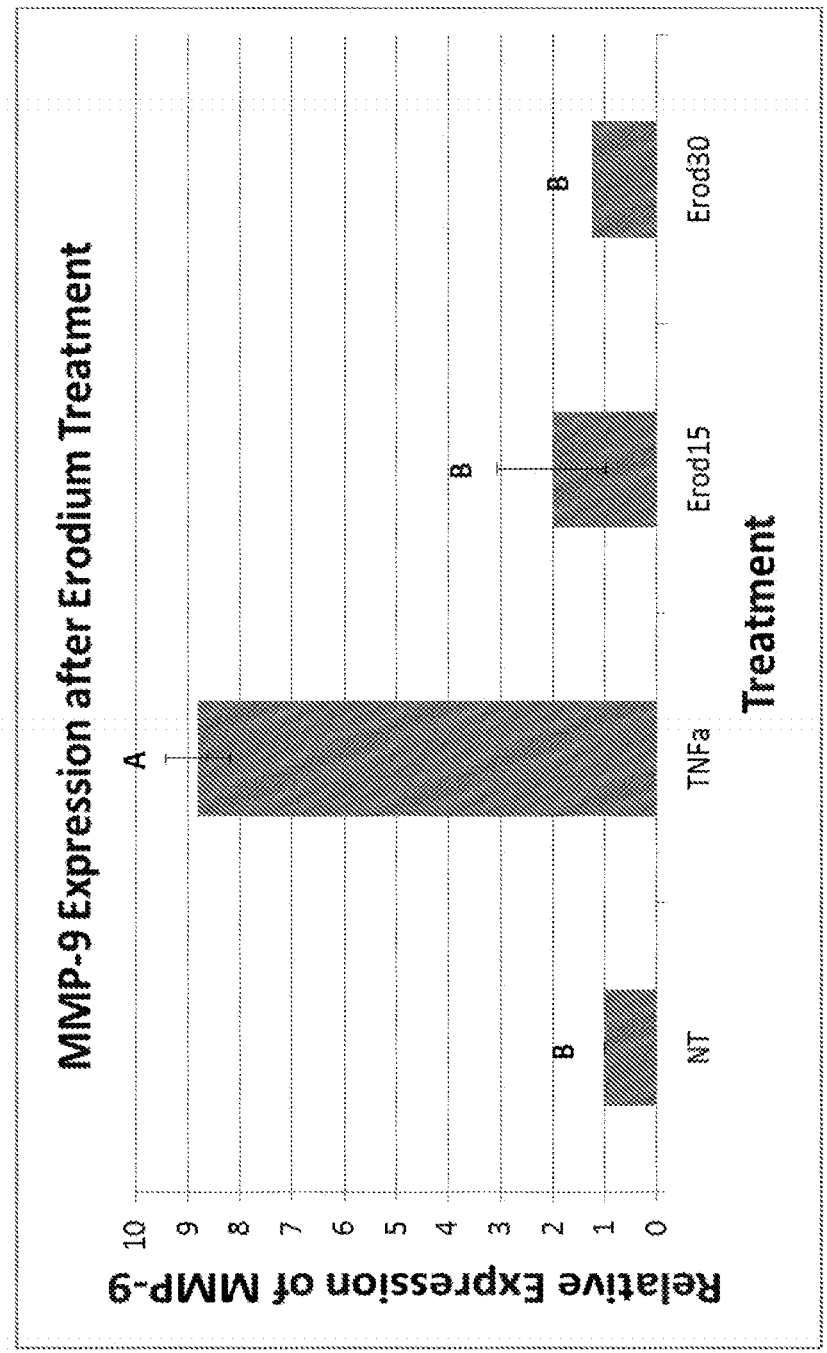

FIG. 16 includes a graph illustrating the changes in MMP-9 expression upon treatment of HaCaT skin cells with *Erodium* water extract. Following TNF-α treatment, cells were treated with *Erodium* water extract. Erod5 and Erod10 are 5× and 10× dilutions respectively. Expression levels of MMP-9 were normalized to the expression of GAPDH mRNA and presented as the relative to GAPDH mRNA. Levels not connected by same letter are significantly different.

Figure 17:
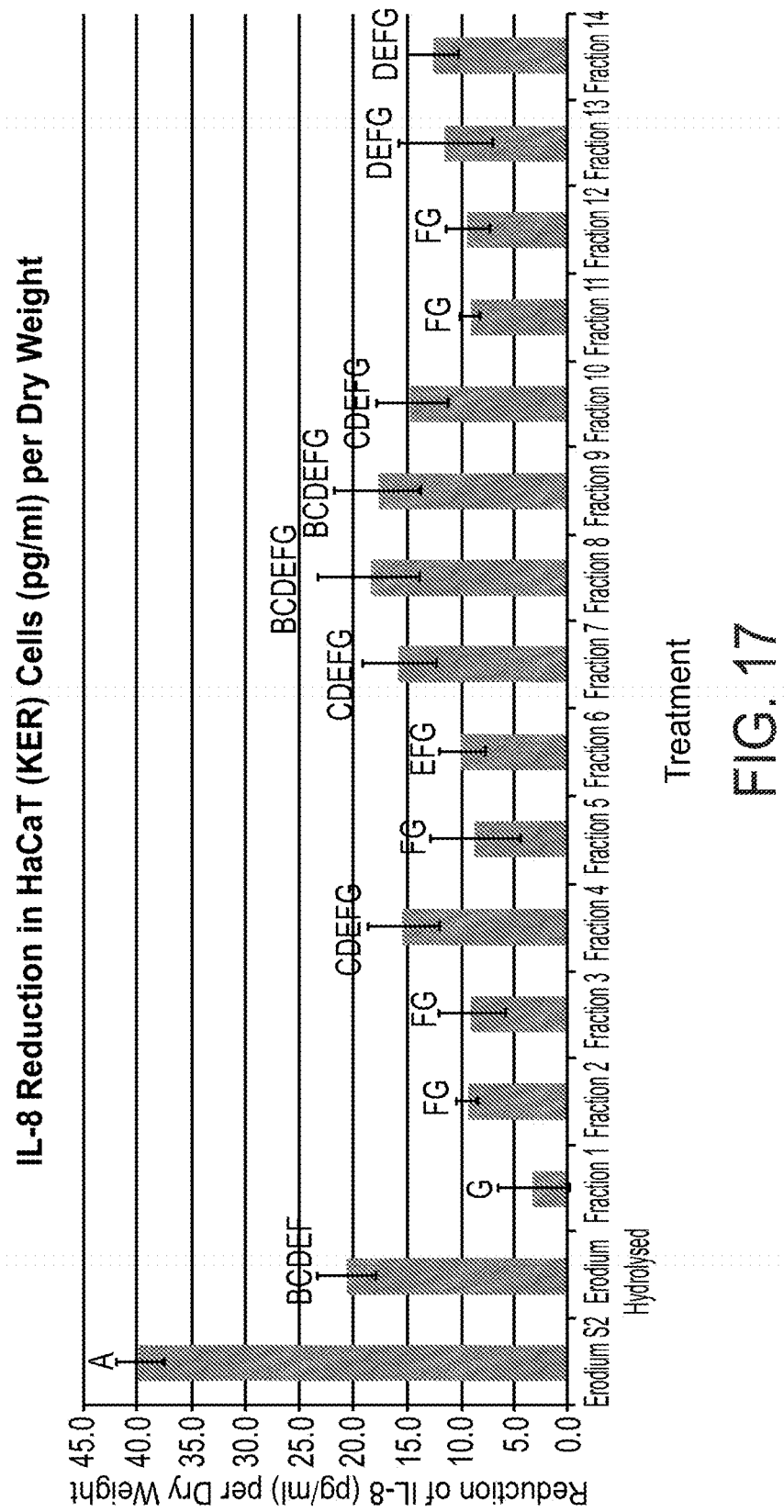

FIG. 17 includes a graph illustrating the anti-inflammatory activity of peaks on HaCaT (KER) skin cells as detected by IL-8 ELISA assay. Levels not connected by same letter are significantly different.

Figure 18A:
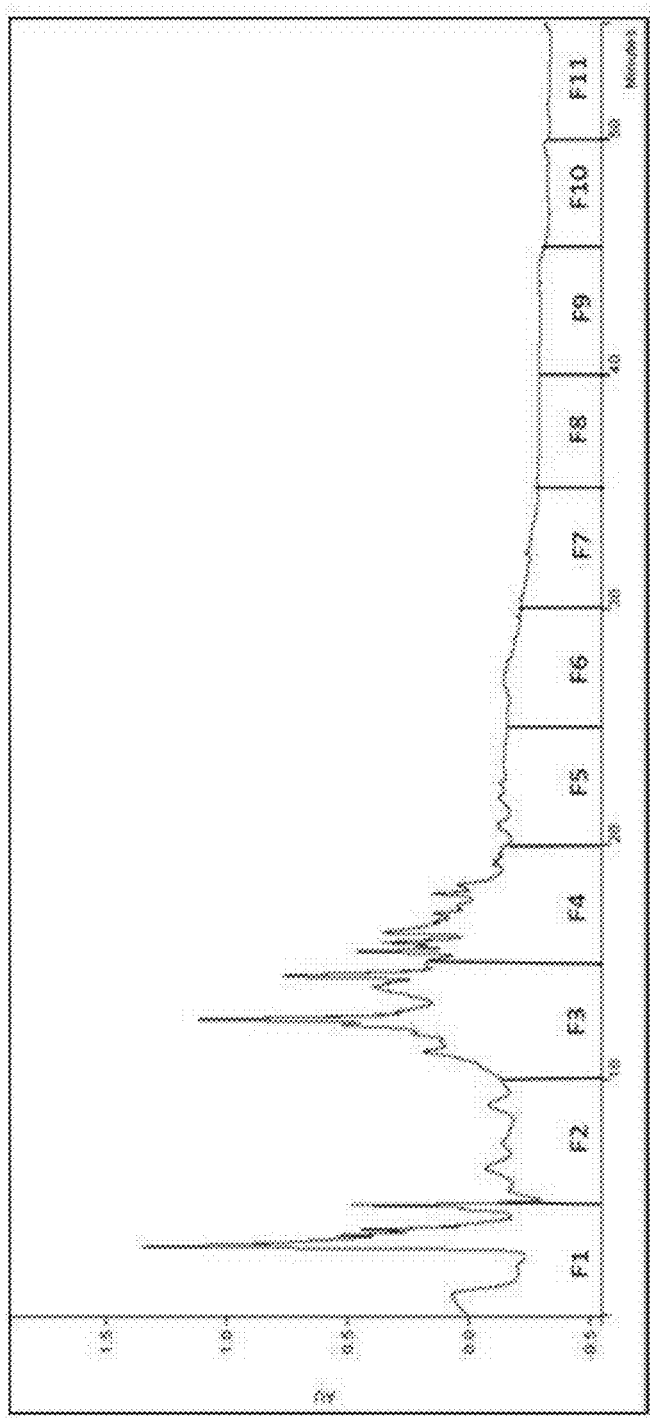
Figure 18B:
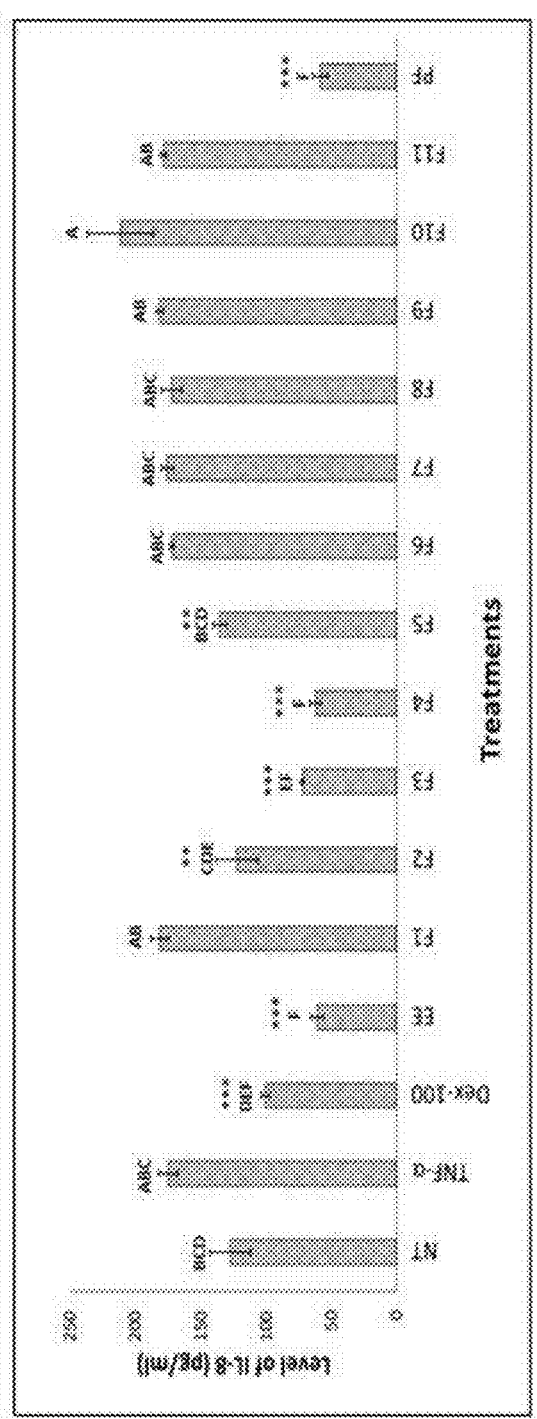

FIGS. 18A-18B include a chromatograph and a vertical bar. (18A) HPLC profile of 70% ethanol extract of *E. crassifolium* tubers (EE) at 220 nm. Solvent gradients were formed by varying the proportion of solvent A (water with 0.1% acetic acid [v/v]) to solvent B (methanol) with the flow rate of 1.0 mL/min. Each fraction (F1-F 11) is from 5 min of HPLC run out of the total 55 min of run; (18B) Levels of IL-8 in HaCaT cells following treatment with the EE and fractions (F1-F 11) and the pooled fractions (PF). HaCaT cells were seeded (50,000 per well) in triplicate in 500 µL growing media and incubated for 24 h at 37° C. in a humidified 5% CO$_2$-95% air atmosphere. Cells were treated with 50 ng/mL TNFα and 50 µL of the EE, F1-F11 and PF for 16 h (all derived from the EE at the concentration of 600 µg/µL). Levels of IL-8 were measured from the supernatant using a commercial ELISA kit. Values (pg/mL) were calculated relative to a TNF-α-treated control. Data represent mean±SE. Multiple comparison was done using Tukey HSD (highly significant difference) test. Means that do not share common letters are significantly different. A pairwise comparison of means between TNF-α and individual treatments was done based on statistical analysis with Student's t-test at $p \leq 0.05^*$; $p \leq 0.01^{}$; $p \leq 0.001^{*}$. Dex-110, Dexamethasone 100 µM.

Figure 19:
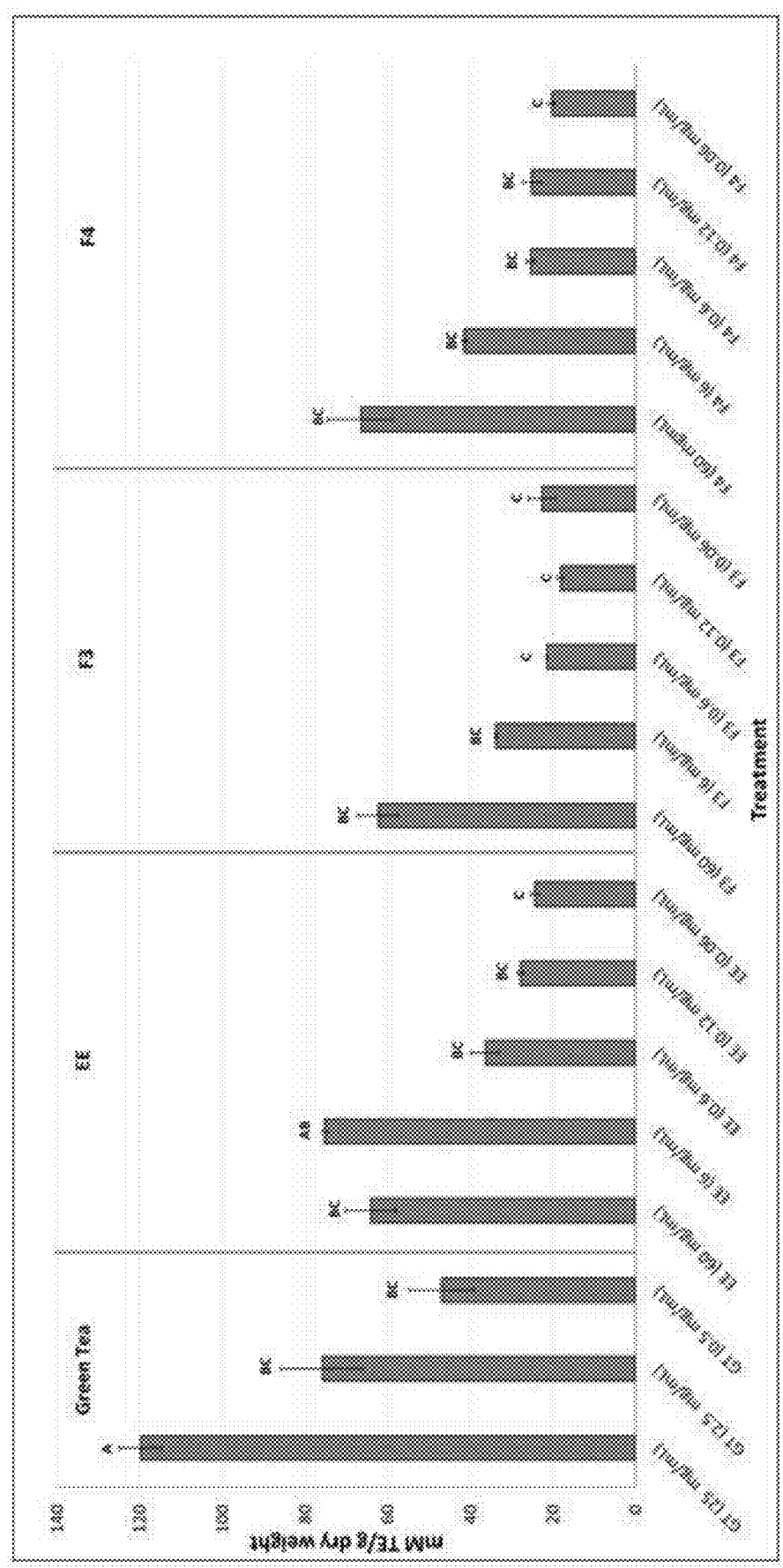

FIG. 19 includes a vertical bar graph showing in vitro anti-oxidant activity of 70% ethanol extract of *E. crassifolium* tubers (EE) and fractions (F3 and F4) in comparison to green tea infusions. An anti-oxidant assay was done using commercial ORAC kit, and Trolox was used as Standard. Data represent mean±SE. Multiple comparison was done using Tukey HSD (highly significant difference) test. Means that do not share common letters are significantly different. GT, green tea decoction.

Figure 20:
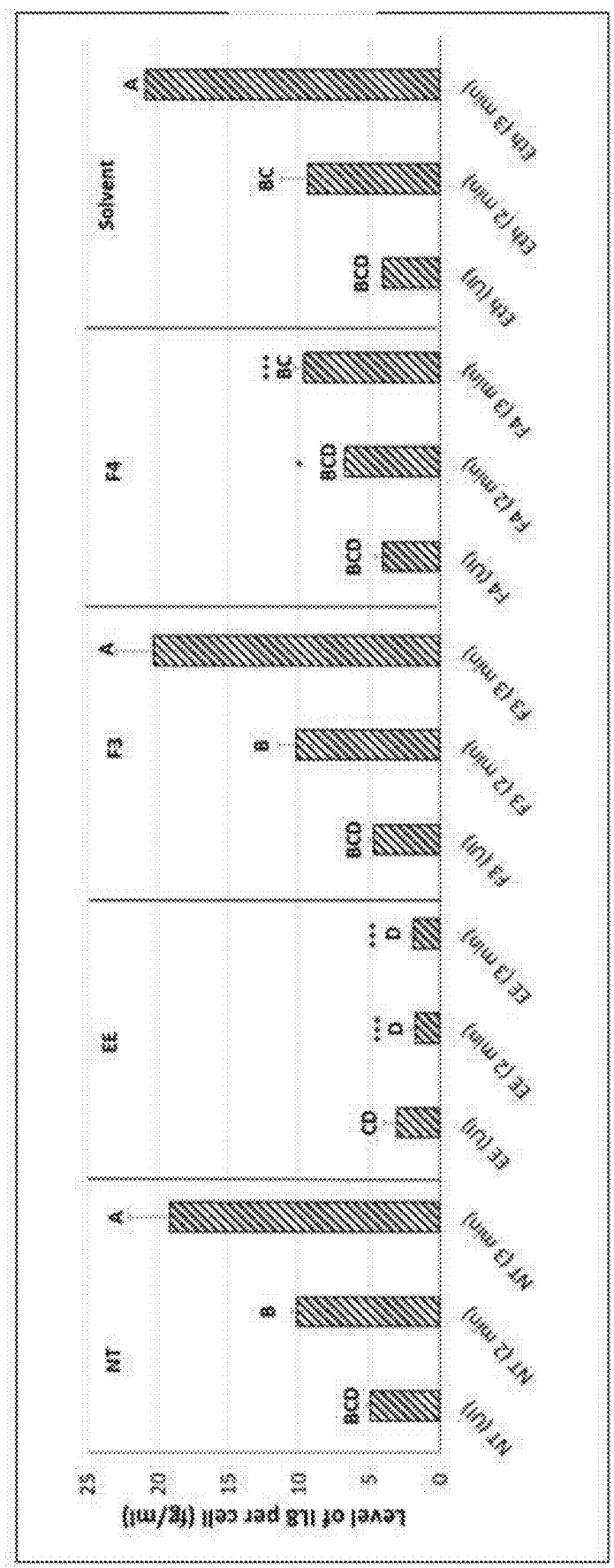

FIG. 20 includes a vertical bar graph showing levels of IL-8 in HaCaT cells following treatment with *E. crassifolium* tubers (EE) and fractions (F3 and F4) following UVB-induction of inflammation for 0, 2 and 3 min. HaCaT cells were seeded (50,000 per well) in triplicate in 500 µL growing media and incubated for 24 h at 37° C. in a humidified 5% CO$_2$-95% air atmosphere. Cells were treated with UVB for the indicated time and then treated with the EE, F3 or F4 (600 µg/mL) for 16 h. Levels of IL-8 were measured from the supernatant using a commercial kit. Values (fg/mL per cell) were calculated relative to a TNF-α-treated control. Data represent mean±SE. Multiple comparison was done using Tukey HSD (highly significant difference) test. Means that do not share common letters are significantly different. A pairwise comparison of means between TNF-α and individual treatments were done based on statistical analysis with Student's t-test at $p \leq 0.05^*$; $p \leq 0.01^{}$; $p \leq 0.001^{*}$. NT-non-treated by the EE, F3 or F4. UI, un-irradiated by UVB. Eth, solvent control.

Figures 21A, 21B:
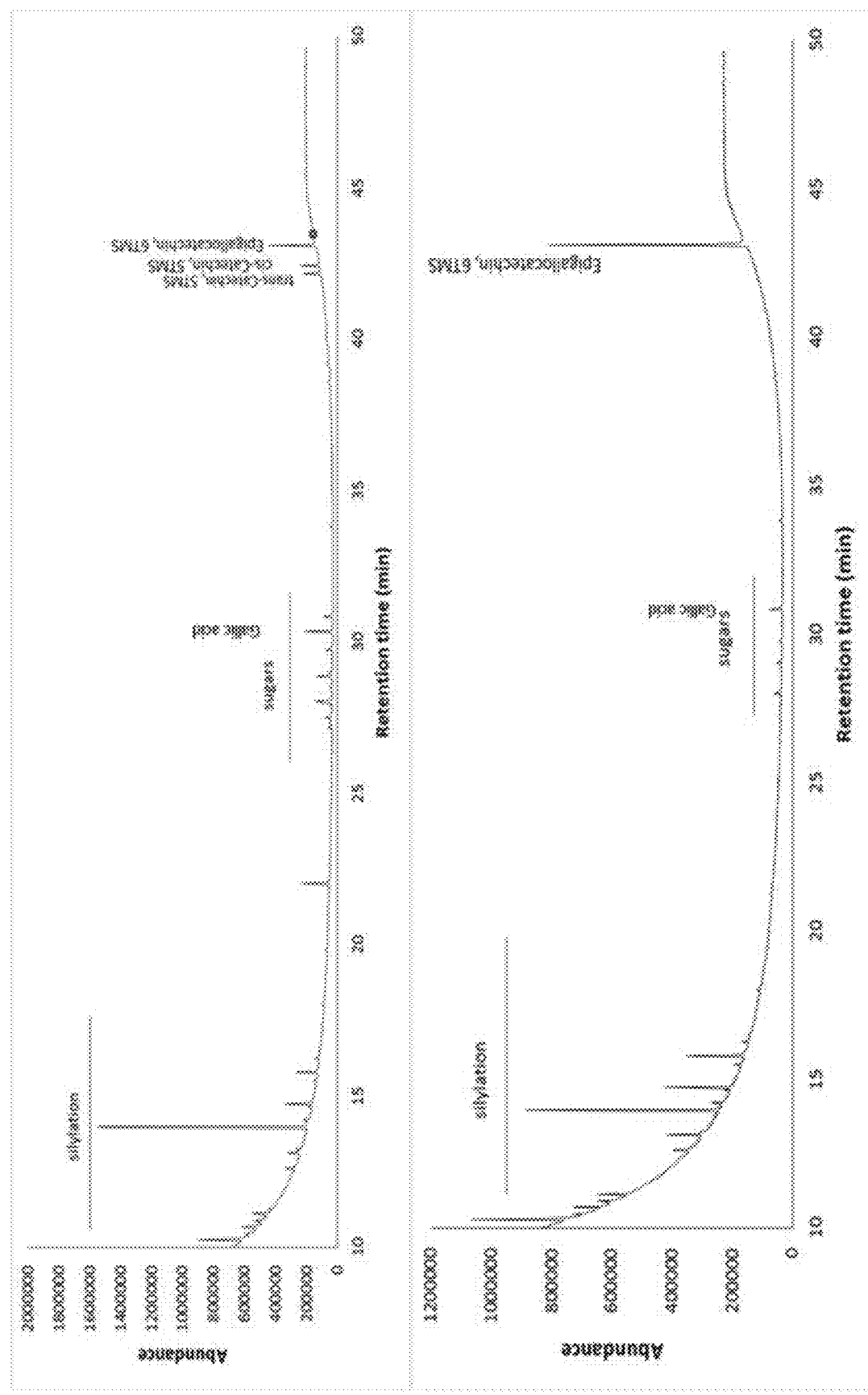

FIGS. 21A-21B include gas chromatography—mass spectrometry (GC/MS)-based chromatograms of F4 (21A) and F4-6 (21B). Prior to GC/MS analysis, 200 µl of N,O-bis(trimethylsilyl)trifluoroacetamide (BSTFA) containing 1% of trimethylchlorosilane (TMCS) was added to each completely dried extract and heated to 70° C. for 20 min. One µL of each sample was injected into the GC/MS using a 1:10 split ratio injection mode. Tables 3 and 4 provides the detailed list of compounds, their respective retention time and percentage of each with regard to the total.

Figure 22A:
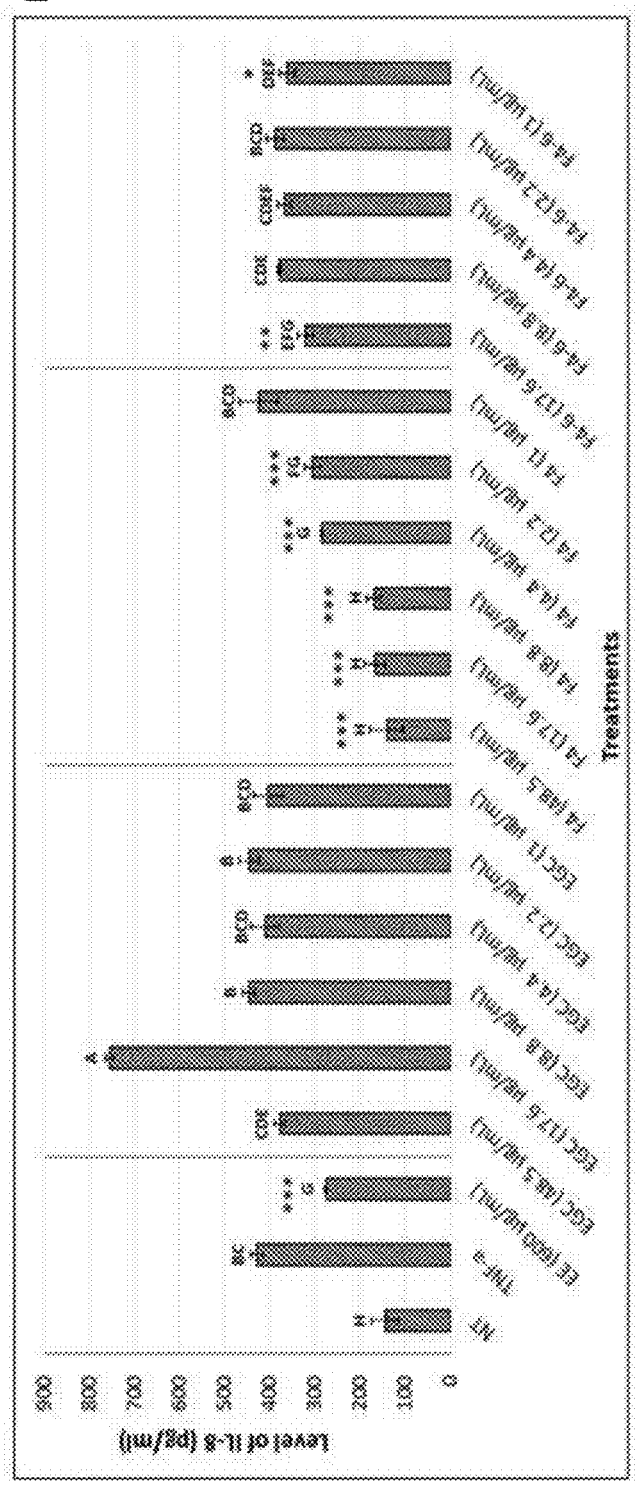
Figure 22B:
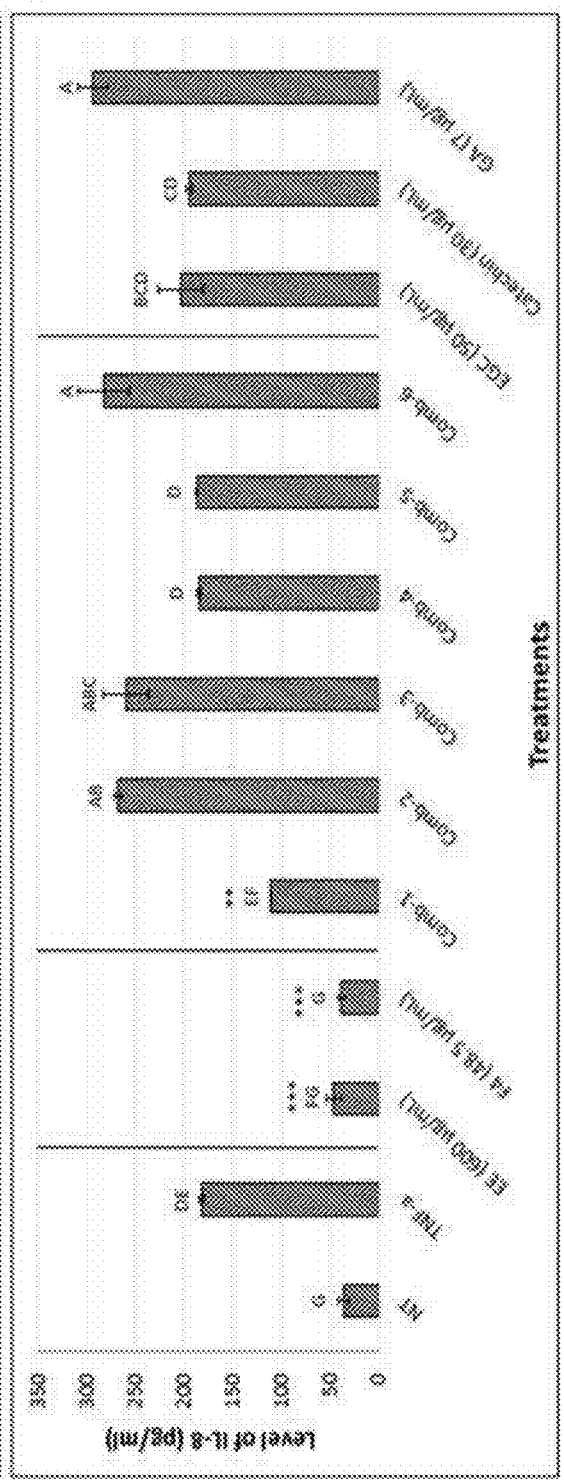

FIGS. 22A-22B include vertical bar graphs showing (22A) levels of IL-8 in HaCaT cells following treatment with *E. crassifolium* tubers (EE), purified EGC or EE fractions (F4 and F4-6). Fraction 4 and F4-6 concentrations are those of their EGC content. (22B) Levels of IL-8 in HaCaT cells following treatment with EE, F4, combinations of EGC, catechin and GA, or each of these compounds separately. Combination 1 (comb-1) contained 50 µg/mL of EGC, 30 µg/mL catechin and 7 µg/mL GA; combination 2 (comb-2) contained 25 µg/mL of EGC, 15 µg/mL catechin and 3.50 µg/mL GA; combination 3 (comb-3) contained 12.50 µg/mL of EGC, 7.50 µg/mL catechin and 1.75 µg/mL GA; combination 4 (comb-4) contained 6.25 µg/mL of EGC, 3.75 µg/mL catechin and 0.88 g/mL GA; combination 5 (comb-5) contained 3.13 µg/mL of EGC, 1.88 µg/mL catechin and 0.44 µg/mL GA, combination 6 (comb-6) contained 1.56 µg/mL of EGC, 0.94 µg/mL of catechin and 0.22 µg/mL of GA. HaCaT cells were seeded (50,000 per well) in triplicate in 500 µL growing media and incubated for 24 h at 37° C. in a humidified 5% CO$_2$—95% air atmosphere. Cells were treated with 50 µg/mL TNF-α and 50 µL of EE, F4, combinations or purified compounds for 16 h. Levels of IL-8 were measured from the supernatant using a commercial kit. Values (pg/mL) were calculated relative to a TNF-α-treated control. Data represent mean±SE. Multiple comparison was done using Tukey HSD (highly significant difference) test. Means that do not share common letters are significantly different. A pairwise comparison of means between TNF-α and individual treatments were done based on statistical analysis with Student's t-test at p≤0.05*; p≤0.01; p≤0.001*. GA—gallic acid; NT—non-treated.

Figures 23A, 23B:
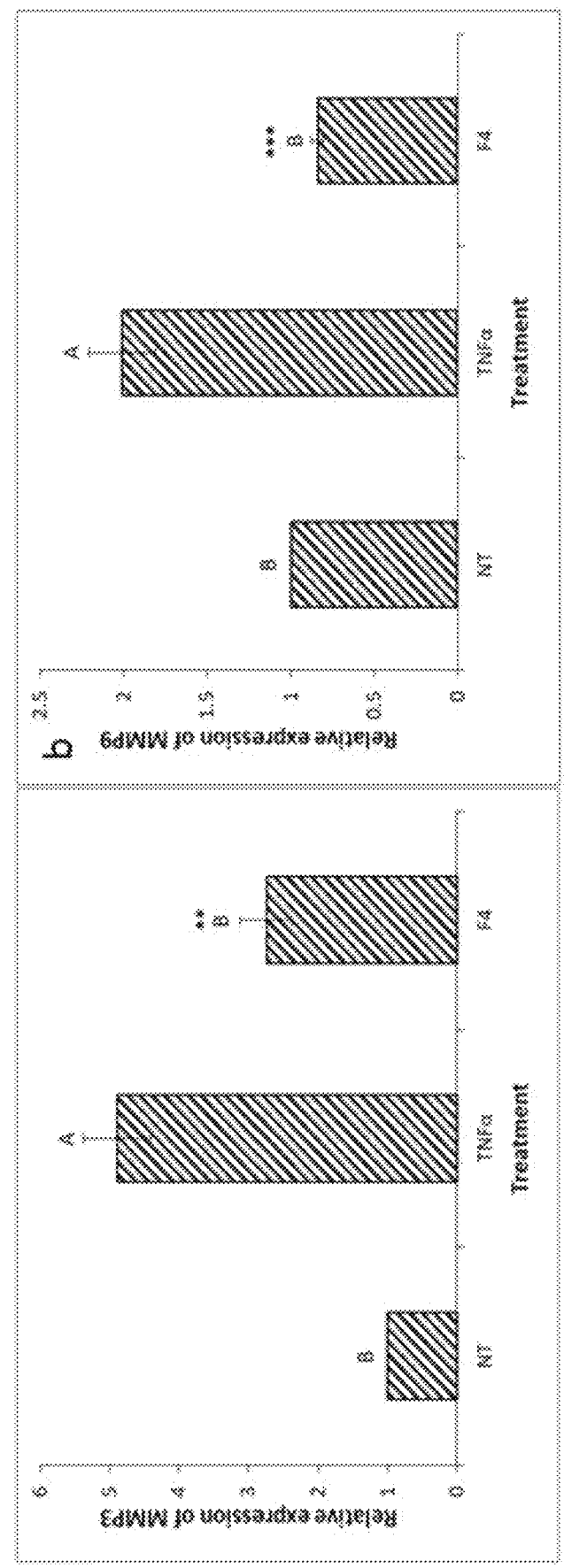

FIGS. 23A-23B include vertical bar graphs showing MMP3 (23A) and MMP9 (23B) gene expression in HaCaT cells following treatment with fraction 4 (F4) of 70% ethanol extract of *E. crassifolium* tubers. Cells were seeded (1,500,000 per well) in triplicate in 500 μL growing media and incubated for 24 h at 37° C. in a humidified 5% $CO_2$-95% air atmosphere. Cells were treated with 400 ng/mL TNF-α overnight and then treated with F4 (3 μg/mL of EGC in F4, $IC_{50}$ concentration) for 16 h before RNA extraction. RNA was extracted and reverse transcribed, and values of the steady-state level of gene transcripts were determined as the ratio between the target gene (MPP3 or MMP9) and a reference gene (GAPDH), and that of treatment vs. no treatment (NT), using the 2-ΔΔCt method. The experiment was performed in three biological replicates, with three technical repeats for each (n=3). Data represent mean±SE. Means that do not share common letters are significantly different based on statistical analysis with Tukey's HSD test. A pairwise comparison of means between TNF-α and individual treatments were done based on statistical analysis with Student's t-test at p≤0.05*; p≤0.01; p≤0.001*. NT-non-treated.

Figures 24A, 24B, 24C:
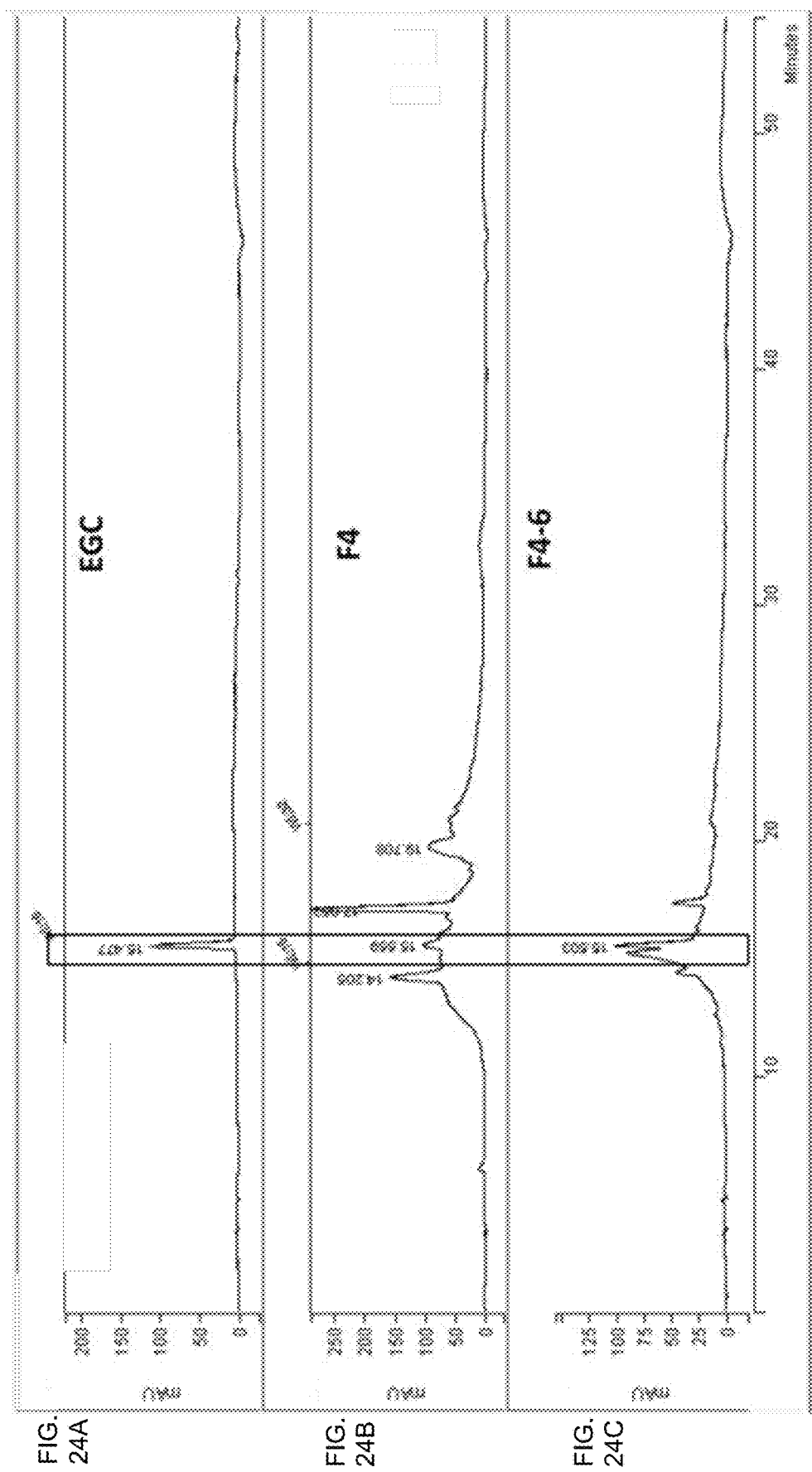

FIGS. 24A-24C include chromatograms showing HPLC profile of (24A) EGC standard with RT (retention time) peak of 15.477 and (24B) fraction F4 with RT peak of 15.559 and (24C) the purified sub-fraction F4-6 with RT peak of 15.503.

Figure 25:
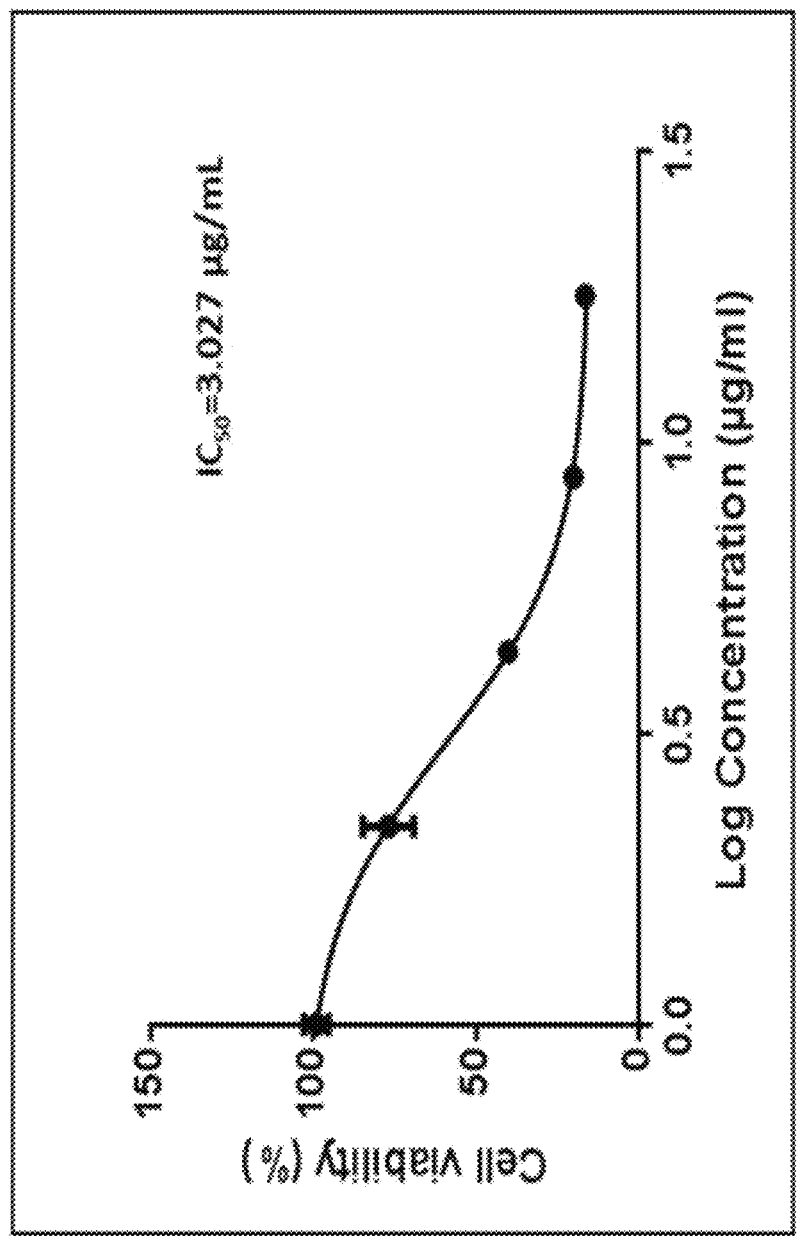

FIG. 25 includes a graph showing the effect of F4 (calculated for EGC content) on the viability of HaCaT cells. Cells were seeded (50,000 per well) in triplicate in 500 μL growing media in 24-well plate and incubated for 24 h at 37° C. in a humidified 5% $CO_2$-95% air atmosphere. Cells were seeded and treated with F4 at various concentrations that were calculated for EGC content in F4, along with 50 ng/mL of TNF-α for 16 h. The cells were then incubated with 10% of resazurin for 4 h. Relative fluorescence at the excitation/emission of 544/590 nm was measured. Values were calculated as the percentage of live cells relative to the non-treated control after reducing the auto-fluorescence of resazurin without cells. $IC_{50}$=3.027 μg/mL of EGC in F4. $IC_{50}$ value was determined using nonlinear regression analysis using GraphPad Prism software.

DETAILED DESCRIPTION OF THE INVENTION

According to some embodiments, there is provided a composition comprising or consisting essentially of: epigallocatechin, mannofuranose, α-D-xylopyranose, gallic acid, palmitic acid, stearic acid, trans-catechin, and cis-catechin.

As used herein, the term "consisting essentially of" denotes that a given compound or substance constitutes the vast majority of the active ingredient's portion or fraction of the composition.

In some embodiments, consisting essentially of means that the combination of epigallocatechin, mannofuranose, α-D-xylopyranose, gallic acid, palmitic acid, stearic acid, trans-catechin, and cis-catechin, constitutes at least 95%, at least 98%, at least 99%, or at least 99.9% by weight, of the active ingredient(s) of the composition, or any value and range therebetween. Each possibility represents a separate embodiment of the invention.

In some embodiments, epigallocatechin is present in the composition in an amount of 35-50% (w/w), 36-60 (w/w), 40-50% (w/w), 38-44% (w/w), 39-47% (w/w), or 40-46% (w/w) of the composition. Each possibility represents a separate embodiment of the invention.

In some embodiments, mannofuranose is present in the composition in an amount of 15-22% (w/w), 16-25% (w/w), 17-23% (w/w), 18-22% (w/w), or 13-21% (w/w) of the composition. Each possibility represents a separate embodiment of the invention.

In some embodiments, α-D-xylopyranose is present in the composition in an amount of 1.5-3.5% (w/w), 1.0-2.5% (w/w), 1.6-3.2% (w/w), or 1.8-2.9% (w/w) of the composition. Each possibility represents a separate embodiment of the invention.

In some embodiments, gallic acid is present in the composition in an amount of 3-7% (w/w), 2-6% (w/w), 1-8% (w/w), 4-7% (w/w), or 3-6% (w/w) of the composition. Each possibility represents a separate embodiment of the invention.

In some embodiments, palmitic acid is present in the composition in an amount of 4-8% (w/w), 3-7% (w/w), 2-9% (w/w), 5-8% (w/w), or 6-9% (w/w) of the composition. Each possibility represents a separate embodiment of the invention.

In some embodiments, stearic acid is present in the composition in an amount of 1.5-3.5% (w/w), 1.0-2.5% (w/w), 1.6-3.2% (w/w), or 1.8-2.9% (w/w) of the composition.

Each possibility represents a separate embodiment of the invention.

In some embodiments, trans-catechin is present in the composition in an amount of 7-16% (w/w), 8-15% (w/w), 9-13% (w/w), 10-15% (w/w), or 6-14% (w/w) of the composition. Each possibility represents a separate embodiment of the invention.

In some embodiments, cis-catechin is present in the composition in an amount of 7-16% (w/w), 8-15% (w/w), 9-13% (w/w), 10-15% (w/w), or 6-14% (w/w) of the composition. Each possibility represents a separate embodiment of the invention.

In some embodiments, epigallocatechin, mannofuranose, α-D-xylopyranose, gallic acid, palmitic acid, stearic acid, trans-catechin, cis-catechin, or any combination thereof, is derived from a polar extract of *Erodium* plant tuber.

In some embodiments, the composition comprises a polar extract of *Erodium* plant tuber or a fraction thereof.

In some embodiments, the composition consists essentially of a polar extract of *Erodium* plant tuber. In some embodiments, the composition consists of a polar extract of *Erodium* plant tuber.

In some embodiments, polar solvent is or comprises ethanol.

In some embodiments, the polar solvent comprises 50-70% (v/v) ethanol, 50-80% (v/v) ethanol, 50-90% (v/v) ethanol, 60-80% (v/v) ethanol, or 65-80% (v/v) ethanol. Each possibility represents a separate embodiment of the invention.

In some embodiments, the *Erodium* plant is *Erodium crassifolium* L'Her, as described herein.

In some embodiments, the composition is a pharmaceutical composition. In some embodiments, the composition is a nutraceutical composition.

In some embodiments, the composition further comprises an acceptable carrier.

In some embodiments, the carrier is or comprises a pharmaceutical carrier or a pharmaceutically acceptable. In some embodiments, the carrier is or comprises a nutraceutical carrier or a nutraceutically acceptable.

In some embodiments, the composition is suitable for topical administration or oral administration. In some embodiments, the composition is a topical composition. In some embodiments, the composition is an oral composition.

According to some embodiments, there is provided a method for preventing or treating a subject afflicted with an inflammatory or a condition associated therewith, comprising administering to the subject a therapeutically effective amount of the composition of the invention.

In some embodiments, an inflammatory disease is as described herein.

In some embodiments, an inflammatory disease comprises a skin disease. In some embodiments, an inflammatory disease comprises an inflammatory skin disease.

In some embodiments, a skin disease or an inflammatory skin disease is selected from: a cutaneous disease, a dermal disease, a bullous skin disease, *pemphigus vulgaris*, bullous pemphigoid, *pemphigus foliaceus*, or any combination thereof.

In some embodiments, an inflammatory disease is induced by irradiation, oxidative stress, or both, as described herein.

In some embodiments, treating comprises reducing the expression level, the activity, or both, of interleukin 8 (IL-8), matrix metalloprotease 3 (MMP3), MMP9, or any combination thereof, in the subject.

In some embodiments, expression level encompasses transcript level, protein level, or both.

In some embodiments, IL-8 activity comprises recruitment of neutrophils (e.g., chemotaxis). In some embodiments, the recruitment of neutrophils comprises a recruitment to a site of damage or infection.

In some embodiments, MMP3 and/or MMP9 activity comprises breakdown of extracellular matrix during tissue remodeling. In some embodiments, MMP3 and/or MMP9 activity comprises breakdown of extracellular matrix proteins during tissue remodeling.

In some embodiments, administering comprises topically administering, orally administering, or both.

The present invention, in some embodiments thereof, relates to extracts of *Erodium* plants and, more particularly, but not exclusively, to polar extracts of tubers of *Erodium* plants.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The *Erodium crassifolium* plant has a Saharo-Arabian phytogeographic distribution. It is a perennial hemicryptophyte, the canopy of which is renewed from buds situated close to the soil surface. The storage organs are tubers, from one small (0.5 cm) spherical tuber in a young plant to between 3-6 larger elongated tubers (1-3 cm) that appear near the end of the roots.

Whilst investigating the medicinal properties of this plant, the present inventors noted that polar extracts of both the tubers and leaves comprised anti-inflammatory activity (FIGS. 2A-B, 3A-B, 9, 10A-B, 11A-B). The present inventors therefore propose that the extracts may be used in the treatment of inflammatory diseases.

The present inventors further found that the polar extracts showed antioxidant activity (FIGS. 14A-D) and anti-pollutant activity (FIGS. 15A-B), prompting their use for treating oxidative stress related disorders. Furthermore, the polar extracts may be used as cosmetics, especially in skin care related compositions.

Thus, according to a first aspect of the present invention, there is provided a method of generating a polar extract of an *Erodium* plant tissue comprising:

(a) contacting the *Erodium* plant tissue with a polar solvent under conditions to allow extraction of soluble agents from said *Erodium* plant tissue into said solvent to generate an extract; and (b) isolating the extract from said *Erodium* plant tissue, thereby generating the polar extract.

*Erodium* is a genus of flowering plants in the botanical family Geraniaceae. The genus includes about 60 species, native to North Africa, Indomalaya, The Middle East and Australia. They are perennials, annuals or subshrubs, with five-petalled flowers in shades of white, pink and purple, that strongly resemble the better-known *Geranium* (cranesbill). American species are known as filarees or heron's bill, whereas Eurasian ones are usually called storksbills in English.

Examples of *Erodium* species contemplated by the present inventors are set forth in Table 1, herein below.

TABLE 1

| | |
|---|---|
| *Erodium acaule* (L.) Bech. & Thell. | *Erodium glandulosum* (Cav.) Willd. |
| *Erodium aethiopicum* (Lam.) Brumh. & Thell. | *Erodium gruinum* (L.) L'Hér. |
| | *Erodium hoefftianum* C. A. Meyer |
| *Erodium aureum* | *Erodium laciniatum* (Cav.) Willd. |
| *Erodium botrys* (Cav.) Bertol. | *Erodium lebelii* Jord. |
| *Erodium brachycarpum* (Godr.) Thell. | *Erodium macrophyllum* Hook. & Arn. |
| *Erodium carolinianum* | |
| *Erodium chium* (L.) Willd. | *Erodium malacoides* (L.) L'Hér. |
| *Erodium chrysantum* L'Hér. ex DC. | *Erodium manescavii* Coss. |
| *Erodium ciconium* (L.) L'Hér. | *Erodium maritimum* (L.) L'Hér. |
| *Erodium cicutarium* (L.) L'Hér. | *Erodium moschatum* (L.) L'Hér. |
| *Erodium corsicum* Léman | *Erodium mouretii* Pitard. |
| *Erodium crinitum* | *Erodium pelargoniflorum* |
| *Erodium crispum* Lapeyr. | *Erodium reichardii* |
| *Erodium crassifolium* L'Her | *Erodium rodiei* (Braun-Blanq.) Poirion |
| *Erodium cygnorum* Nees | |
| *Erodium foetidum* (L.) L'Hér. | *Erodium salzmannii* Delile |
| | *Erodium texanum* A. Gray |
| | *Erodium trifolium* |

According to a particular embodiment, the *Erodium* plant is *Erodium crassifolium* L'Her.

The extract may be derived from a cultivated *Erodium* plant (i.e. not grown in their natural habitat) or may be derived from *Erodium* plants which grow in the wild.

A method of growing *Erodium crassifolium* L'Her plants is described in the Examples section, herein below.

Thus, the present inventors contemplate planting seeds of *Erodium crassifolium* and harvesting the plant or the tubers prior to generation of the extract.

The tissue of the *Erodium* plant from which the extract is generated may be the leaves or the tubers. In particular, when the *Erodium* plant is *Erodium crassifolium* L'Her, the tissue may be leaves or tubers. When the *Erodium* plant is not *Erodium crassifolium* L'Her, the tissue is typically the tuber. Any size tuber is contemplated. In a particular embodiment, the tuber is between 0.5-4 cm in length, although more preferably between 1-3 cm in length and even more preferably between 2-3 cm in length.

Polar solvents suitable for use with the present invention include, but are not limited to, a C1-C10 compound having at least one heteroatom selected from: N, O, P, S, and combinations thereof. In some embodiments, the polar solvent includes at least one of: water, a C1-C10 alcohol, a C4-C10 ether, C3-C10 aldehyde, a C3-C10 ketone, a C2-C10 carboxylic acid, a C2-C10 ester, a C3-C10amine, a C1-C5 amide, and combinations thereof. In some embodiments, the polar solvent comprises a polar, protic solvent (e.g., methanol). In some embodiments, the polar solvent comprises a polar, aprotic solvent (e.g., acetone). Polar solvents suitable for use with the present invention include, but are not limited to, methanol, ethanol, n-propanol, isopropanol, a butanol, a pentanol, acetone, methylethylketone, ethylacetate, acetonitrile, tetrahydrofuran, dimethylformamide, dimethylsulfoxide, water, and combinations thereof.

In particular embodiments, the extract is an aqueous extract.

In some embodiments, the polar solvent has a dielectric constant of about 5 or greater, about 10 or greater, about 15 or greater, about 20 or greater, about 25 or greater, about 30 or greater, or about 40 or greater.

In some embodiments, the polar solvent has a boiling point of about 200° C. or less, about 175° C. or less, about 150° C. or less, about 125° C. or less, or about 100° C. or less.

The concentration or amount of a polar solvent used to extract materials from the *Erodium* plant tissue can be varied. Generally, the ratio of a polar solvent to *Erodium* plant tissue (weight to weight) is the amount of a polar solvent sufficient to extract about 75% or more, about 85% or more, about 90% or more, about 95% or more, about 97% or more, or about 99% or more of a material having anti-inflammatory or anti-oxidative stress activity. For example, further processing of the *Erodium* plant tissue with an additional polar solvent after an initial extraction would provide about 25% or less, about 15% or less, about 10% or less, about 5% or less, about 3% or less, or about 1% or less of an *Erodium* plant tissue extract having anti-inflammatory/anti-oxidative stress activity in addition to that extracted by an initial extraction with a polar solvent. In some embodiments, the ratio of polar solvent to tuber is about 100:1 to about 1:100, or about 10:1 to about 1:10 by weight.

In some embodiments, the *Erodium* plant tissue is contacted with a polar solvent for about 15 minutes or more, about 30 minutes or more, about 1 hour or more, about 4 hours or more, about 8 hours or more, about 16 hours or more, about 24 hours or more, about 48 hours or more, or about 72 hours or more.

Temperature can also be controlled during the contacting. In some embodiments, the *Erodium* plant tissue is contacted with a polar solvent at a temperature of about −25° C. to about 200° C., about 0° C. to about 150° C., about 25° C. to about 100° C. or about 25° C. to about 35° C.

In some embodiments, the process of the present invention comprises isolating a liquid extract from the mixture comprising the liquid extract and solids. Suitable means for isolating the liquid extract include those known in the art of organic synthesis and include, but are not limited to, gravity filtration, suction and/or vacuum filtration, centrifuging, setting and decanting, and the like. In some embodiments, the isolating comprises filtering a liquid extract through a porous membrane, sponge, zeolite, paper, or the like having a pore size of about 100 μm or less, about 50 μm or less, about 20 μm or less, about 10 μm or less, about 5 μm or less, or about 1 μm or less.

The present inventors contemplate drying (i.e. removal of the polar solvent) and/or freezing the polar extract following generation.

The method for drying the extract (i.e. removing the polar solvent) is not particularly limited and can include solvent evaporation at a reduced pressure (e.g., sub atmospheric pressure) and/or an elevated temperature (e.g., above about 25° C.). The present invention also includes the removal of the polar solvent (and other process steps) being conducted under controlled temperature conditions such as, but not limited to, about 120° C. or less, about 100° C. or less, about 80° C. or less, about 60° C. or less, about 40° C. or less or about 30° C. or less. In some embodiments, it can be difficult to completely remove a polar solvent from a liquid extract by standard solvent removal procedures such as evaporation. In some embodiments, processes such as co-evaporation, lyophilization, and the like can be used to completely remove the polar solvent from a liquid fraction to form a dry powder, dry pellet, dry granulate, paste, and the like.

Following generation of the polar extract, the present inventors further contemplates additional purification steps so as to further purify active agents from the extract.

Thus, for example, the present inventors further propose fractionating the polar extract. Fractionating can be performed by processes such as, but not limited to: column chromatography, preparative high performance liquid chromatography ("HPLC"), reduced pressure distillation, and combinations thereof.

In some embodiments, the fractionating comprises applying the polar extract to an adsorbent and isolating an *Erodium* extract having anti-inflammatory activity or anti-oxidative stress activity by column chromatography. In some embodiments, the polar extract can be further purified using a chromatographic separation system comprising an adsorbent. In some embodiments, a chromatographic separation system further comprises a material in addition to an adsorbent, such as, but not limited to, a porous membrane, an ion exchange resin, a silica gel, a reverse phase silica gel, or any resin, polymer, colloid, and the like suitable for performing a separation based upon a molecular property such as, but not limited to, polarity, size, functional group, and combinations thereof.

In some embodiments, an adsorbent is porous. In some embodiments, a porous adsorbent has a pore size of about 20 nm or less, about 15 nm or less, about 10 nm or less, about 8 nm or less, about 6 nm or less, about 5 nm or less, about 4 nm or less, about 3 nm or less, about 2 nm or less, or about 1 nm or less. In some embodiments, a porous adsorbent has a pore size of about 0.6 nm to about 20 nm, about 0.8 nm to about 15 nm, about 1 nm to about 10 nm, about 1.5 nm to about 8 nm, about 2 nm, about 4 nm, about 6 nm, or about 8 nm.

Exemplary adsorbents suitable for use with the present invention include, but are not limited to, cross-linked styrene-divinylbenzene resins (e.g., DOWEX® OPTIPORE® Resins, The Dow Chemical Co., Midland, Mich. and AMBERLITE® XAD4, XAD16, XAD1180, and XAD1600, Rohm and Haas Co., Philadelphia, Pa.); highly cross-linked, aliphatic, or phenol-formaldehyde condensate polymers (e.g., AMBERLITE® XAD7IIP and XAD761, Rohm and Haas Co.); carbonaceous resins (e.g., AMBERSORB® 563 and 572, Rohm and Haas Co.); granular activated carbon (e.g., FILTRASORB® 300 and 400, Calgon Carbon Corp., Pittsburgh, Pa.); and combinations thereof.

An eluting solvent is applied to an adsorbent loaded with the aqueous extract to elute fractions from the adsorbent. In some embodiments, an eluting solvent is an aqueous eluent comprising water. In some embodiments, an eluting solvent is deionized (e.g., deionized water). Alternatively, the tonicity of an eluting solvent can be increased by including one or more ions, salts, and the like to an eluting solvent.

In some embodiments, an eluting solvent comprises an "organic," which as used herein refers to a liquid, solid, or gas that includes at least one carbon atom in its molecular structure. Organics suitable for use as eluting solvents include, but are not limited to, methanol, ethanol, propanol, acetone, carbon dioxide, methylethyl ketone, acetonitrile, butyronitrile, carbon dioxide, ethyl acetate, tetrahydrofuran, di-iso-propylether, ammonia, triethylamine, N,N-dimethylformamide, N,N-dimethylacetamide, and the like, and combinations thereof. In some embodiments, an eluting solvent comprises an organic and water, e.g., about 95% ethanol and about 5% water.

The polar extracts and/or agents purified therefrom may be tested for anti-inflammatory activity and/or anti oxidative stress activity and/or anti-aging activity.

Exemplary methods for testing the above mentioned activities are described in the Examples section herein below.

Other methods for testing the activity of the extract (or agents isolated therefrom) for anti-oxidant activity are detailed in the article Am J Clin Nutr January 2005 vol. 81 no. 1 261S-267S by Andrew Collins.

For testing the effect of the extract (or agents isolated therefrom) on inflammation, in vitro assays may be used to which analyze the effect on cell derived factors such as IFN-gamma, IL-8, leukotriene B4, nitric oxide, prostaglandins, TNF-alpha and IL-1. Many in vivo assays are known in the art for testing anti-inflammatory activity and are contemplated by the present invention.

The extract of the present invention can also be characterized by analytical methods such as, but not limited to, spectroscopic methods such as, but not limited to, ultraviolet-visible spectroscopy ("UV-Vis"), infrared spectroscopy ("IR"), and the like; mass-spectrometry ("MS") methods such as, but not limited to, time-of-flight MS; quadrupole MS; electrospray MS, Fourier-transform MS, Matrix-Assisted Laser Desorption/Ionization ("MALDI"), and the like; chromatographic methods such as, but not limited to, gas-chromatography ("GC"), liquid chromatograph ("LC"), high-performance liquid chromatography ("HPLC"), and the like; and combinations thereof (e.g., GC/MS, LC/MS, HPLC/UV-Vis, and the like), and other analytical methods known to persons of ordinary skill in the art.

The present invention is also directed to a product prepared by the process of the present invention. In some embodiments, the *Erodium* extract of the present invention is a polar extract (e.g. aqueous extract) and is substantially free of cytotoxic compounds. In some embodiments, the *Erodium* extract of the present invention substantially lacks cytotoxic activity. As used herein, "substantially lacks cytotoxic activity" refers to extracts that are not appreciably cytotoxic under in vitro or in vivo testing and/or administering conditions. In some embodiments, "substantially lacks cytotoxic activity" refers to extracts lacking cytotoxic activity as described in S. B. Ullman et al., Exp. Med. Sur. 3:11 (1945) and S. B. Ullman et al, Exp. Med. Sur./0:287 (1952), both of which are incorporated herein by reference in their entirety.

In one embodiment, the polar extracts derived from *Erodium* plants (e.g. from the tubers and/or leaves), do not comprise plant tissue or other water insoluble components.

In other embodiments, the polar extracts derived from *Erodium* plants (e.g. from the tubers and/or leaves), have not been boiled for more than 20 minutes, more preferably no more than 10 minutes and even more preferably have not been boiled for more than 1 minute.

In still other embodiments, the extract does not comprise material from more than five plants of different species, more than four plants of different species, more than three plants of different species, or even more than two plants of different species.

Since the extracts of the present invention or active agents derived therefrom have anti-inflammatory activity and/or antioxidant activity, they may be used for treating diseases or disorders related thereto.

Thus, according to another aspect of the present invention there is provided a method of treating an inflammatory disease or a disease related to oxidative stress in a subject in need thereof comprising administering to the subject a therapeutically effective amount of a polar extract of tubers of an *Erodium* plant, thereby treating the disease.

As used herein the phrase "oxidative stress" refers to an undesirable imbalance where oxidants outnumber antioxidants. This situation can arise if the rate of ROS production overwhelms existing antioxidant defenses. In such circumstances, a series of cellular responses can occur that can lead to an even greater increase in ROS production. Excessive ROS production and its otherwise ineffective regulation can be detrimental to cells and tissues, inducing cellular damage that ultimately can lead to cell death (apoptosis). Oxidative stress-associated damage also can cause undesirable changes to the structural and functional integrities of cells that can lead to the propagation of cells instead of apoptosis. Additionally, oxidatively-damaged cellular macromolecules can trigger immune responses that can lead to disease. See generally, D. G. Lindsay et al. (2002) Mol. Aspects of Med. 23:1-38, incorporated herein by reference.

It will be appreciated that oxidative stress may be responsible for initiating or otherwise causing disease. Alternatively, or additionally, the progression of the disease can be affected by any resultant oxidative stress.

Hence the phrase "oxidative stress related disease" as used herein, refers to a disease or medical condition (including syndromes) wherein the onset or progression thereof is promoted by oxidative stress. Since oxidative stress is believed to be responsible for the pathogenesis of many neurological, heart, malignant and age-associated diseases, the present invention contemplates all such diseases including for example, atherosclerosis, autoimmune diseases, cancer, cardiovascular disease, cataract, dementia, diabetes and diabetic vasculopathy, and neurodegenerative diseases.

Exemplary neurodegenerative diseases include, but are not limited to Parkinson's disease, Multiple Sclerosis, ALS, multi-system atrophy, Alzheimer's disease, stroke, progressive supranuclear palsy, fronto-temporal dementia with parkinsonism linked to chromosome 17 and Pick's disease.

In some embodiments, inflammatory diseases, include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J. C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, *Pemphigus vulgaris*, bullous pemphigoid and *Pemphigus foliaceus*.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to, rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, *pemphigus vulgaris*, bullous pemphigoid and *pemphigus foliaceus*.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the extracts of the present invention are not used to treat epilepsy.

The extract may be administered to the subject per se or may be provided as part of a pharmaceutical composition.

The purpose of a pharmaceutical composition is to facilitate administration of an active ingredient (herein the *Erodium* extract) to an organism (e.g., a human being).

Pharmaceutical compositions may be manufactured by processes well known in the art, e.g., by means of conventional mixing, dissolving, granulating, dragee-making, levigating, emulsifying, encapsulating, entrapping or lyophilizing processes.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include without limitation, calcium carbonate, calcium phosphate, various sugars and types of starch, cellulose derivatives, gelatin, vegetable oils, polyethylene glycols, sodium stearate, glycerol monostearate, talc, sodium chloride, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Further techniques for formulation and administration of active ingredients may be found in "Remington's Pharmaceutical Sciences," Mack Publishing Co., Easton, PA, latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

Formulations for oral delivery can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should be suitable for the mode of administration.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For transdermal administration, the composition can be formulated in a form of a gel, a cream, an ointment, a paste, a lotion, a milk, a suspension, an aerosol, a spray, a foam, a serum, a swab, a pledget, a pad or a patch. Formulations for transdermal delivery can typically include carriers such as water, liquid alcohols, liquid glycols, liquid polyalkylene glycols, liquid esters, liquid amides, liquid protein hydrolysates, liquid alkylated protein hydrolysates, liquid lanolin, lanolin derivatives, glycerin, mineral oil, silicone, petroleum jelly, lanolin, fatty acids, vegetable oils, parabens, waxes, and like materials commonly employed in topical compositions. Various additives, known to those skilled in the art, may be included in the transdermal formulations of the invention. For example, solvents may be used to solubilize certain active ingredients substances. Other optional additives include skin permeation enhancers, opacifiers, antioxidants, gelling agents, thickening agents, stabilizers, and the like.

For buccal administration, the compositions may take the form of tablets or lozenges formulated in conventional manner.

For injection, the active ingredients of the pharmaceutical composition may be formulated in aqueous solutions, preferably in physiologically compatible buffers such as Hank's solution, Ringer's solution, or physiological salt buffer.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The composition can be formulated as rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Examples of suitable coating materials include, but are not limited to, cellulose polymers such as cellulose acetate phthalate, hydroxypropyl cellulose, hydroxypropyl methylcelhilose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers", are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropyhnethylcellulose, hydroxypropylcellulose, ethylcellulose, and veegum, and synthetic polymers such as acrylic acid and methacrylic acid copolymers, methacrylic acid copolymers, methyl methacrylate copolymers, amino-alkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-β-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The compounds may be complexed with other agents as part of their being pharmaceutically formulated. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g., magnesium stearates, stearic acid, silicone fluid, talc, waxes, oils, and colloidal silica); and disintegrators (e.g., micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human.

The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

Dosage amount and interval may be adjusted individually so that sufficient amount of the active agents present in the extract reach the appropriate cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

The *Erodium* extract of the present invention can be administered to a subject (e.g., a human or animal) in need thereof in a variety of other forms including a nutraceutical composition or a cosmetic composition.

As used herein, a "nutraceutical composition" refers to any substance that may be considered a food or part of a food and provides medical or health benefits, including the prevention and treatment of disease. In some embodiments, a nutraceutical composition is intended to supplement the diet and contains at least one or more of the following ingredients: a vitamin; a mineral; an herb; a botanical; a fruit; a vegetable; an amino acid; or a concentrate, metabolite, constituent, or extract of any of the previously mentioned ingredients; and combinations thereof.

In some embodiments, a nutraceutical composition of the present invention can be administered as a "dietary supplement," as defined by the U.S. Food and Drug Administration, which is a product taken by mouth that contains a "dietary ingredient" such as, but not limited to, a vitamin, a mineral, an herb or other botanical, an amino acid, and substances such as an enzyme, an organ tissue, a glandular, a metabolite, or an extract or concentrate thereof.

Non-limiting forms of nutraceutical compositions of the present invention include: a tablet, a capsule, a softgel, a gelcap, a liquid, a powder, a solution, a tincture, a suspension, a syrup, or other forms known to persons of skill in the art. A nutraceutical composition can also be in the form of a food, such as, but not limited to, a food bar, a beverage, a food gel, a food additive/supplement, a powder, a syrup, and combinations thereof.

In one embodiment, the nutraceutical composition is not formulated in a honey. Since the extracts of the present invention comprise anti-oxidant activity and anti-inflammatory activity as well as protecting against UV radiation, the present inventors contemplate that another use thereof is in cosmetic compositions for treating the skin. Thus, the agents of the present invention may be formulated for cosmetics.

Suitable cosmetic formulations contemplated by the present invention include, but are not limited to a cream, a face mask, a scrub, a soap, a wash or a gel.

Thus, according to another aspect of the present invention there is provided a cosmetic care method comprising applying to at least one body zone (e.g. face) in need thereof of an efficient amount of a composition comprising an *Erodium* extract as defined herein. According to a particular embodiment, the method is for moisturizing the skin, and/or for protecting it against any type of stress, and/or alternatively for producing an antiaging effect.

Such compositions typically comprise dermatologically acceptable carriers suitable for external topical application.

The cosmetic composition according to the present invention may further comprise at least one pharmaceutical adjuvant known to the person skilled in the art, selected from thickeners, preservatives, fragrances, colorants, chemical or mineral filters, moisturizing agents, thermal spring water, etc.

The composition may comprise at least one agent selected from a sebum-regulating agent, an antibacterial agent, an antifungal agent, a keratolytic agent, a keratoregulating agent, an astringent, an anti-inflammatory/anti-irritant, an antioxidant/free-radical scavenger, a cicatrizing agent, an anti-aging agent and/or a moisturizing agent.

The term "sebum-regulating agent" refers, for example, to 5-α-reductase inhibitors, notably the active agent 5-α-Avocuta® sold by Laboratoires Expanscience. Zinc and gluconate salts thereof, salicylate and pyroglutamic acid, also have sebum-suppressing activity. Mention may also be made of spironolactone, an anti-androgen and aldosterone antagonist, which significantly reduces the sebum secretion rate after 12 weeks of application. Other extracted molecules, for example from seeds of the pumpkin *Cucurbita pepo*, and squash seed oil, as well as palm cabbage, limit sebum production by inhibiting 5-α-reductase transcription and activity. Other sebum-regulating agents of lipid origin that act on sebum quality, such as linoleic acid, are of interest.

The terms "anti-bacterial agent" and "antifungal agent" refer to molecules that limit the growth of or destroy pathogenic microorganisms such as certain bacteria like *P. acnes* or certain fungi (*Malassezia furfur*). The most traditional are preservatives generally used in cosmetics or nutraceuticals, molecules with anti-bacterial activity (pseudo-preservatives) such as caprylic derivatives (caproyl glycine, glyceryl caprylate, etc.), such as hexanediol and sodium levulinate, zinc and copper derivatives (gluconate and PCA), phytosphingosine and derivatives thereof, benzoyl peroxide, piroctone olamine, zinc pyrithione, selenium sulfide, econazole, ketoconazole, or local antibiotics such as erythromycin and clindamycin, etc.

The terms "keratoregulating agent" and "keratolytic agent" refer to an agent that regulates or helps the elimination of dead cells of the stratum corneum of the epidermis. The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), willow bark (*Salix alba* bark extract), azelaic acid and salts and esters thereof, salicylic acid and derivatives thereof such as capryloyl salicylic acid or in combination with other molecules such as the combination of salicylic acid and polysaccharide (beta-hydroxy acid, or BHA), tazarotene, adapalene, as well as molecules of the retinoid family such as tretinoin, retinaldehyde, isotretinoin and retinol.

The term "astringent" refers to an agent that helps constrict pores, the most commonly used being polyphenols, zinc derivatives and witch hazel.

Exemplary anti-inflammatory/anti-irritant agents that may be included in the cosmetic compositions include glycyrrhetinic acid (licorice derivative) and salts and esters thereof, alpha-bisabolol, *Ginkgo biloba*, Calendula, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide'® (oxazoline derivative), anti-glycation agents such as carnosine, N-acetyl-cysteine, isoflavones such as, for example, genistein/genistin, daidzein/daidzin, spring water or thermal spring water (eau d'Avene, eau de la Roche Posay, eau de Saint Gervais, eau d'Uriage, eau de Gamarde), goji extracts (*Lycium barbarum*), plant amino acid peptides or complexes, topical dapsone, or anti-inflammatory drugs.

Exemplary antioxidants/free-radical scavengers that may be used in combination are advantageously selected from the group comprised of thiols and phenols, licorice derivatives such as glycyrrhetinic acid and salts and esters thereof, alpha-bisabolol, *Ginkgo biloba* extract, Calendula extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the family of polyphenols such as tannins, phenolic acids, anthocyanins, flavonoids such as, for example, extracts of green tea, of red berries, of cocoa, of grapes, of *Passiflora incarnata* or of Citrus, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function which may be used in combination are advantageously vitamin A, panthenol (vitamin B5), Avocadofurane®, avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (*Acacia catechu*). The trace elements that may be used are advantageously selected from the group comprised of copper, magnesium, manganese, chromium, selenium, silicon, zinc and mixtures thereof.

The anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The most commonly used moisturizers/emollients are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, monounsaturated and polyunsaturated omega-3, -6, -7 and -9 fatty acids (linoleic acid, palmitoleic acid, etc.), sunflower oleodistillate, avocado peptides and cupuacu butter.

General

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "about" when combined with a value refers to plus and minus 10% of the reference value. For example, a length of about 1,000 nanometers (nm) refers to a length of 1,000 nm±100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological, and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Growth Protocol of *Erodium crassifolium* Plants

Seeding was done in 1.5 meter planting beds (from center to center) in two strips 40 cm away from each other and irrigated with a drip irrigation system in which droppers were places every 20 cm. Total number of plants in one meter—10. Seeding was carried out in December.

Fertilization with a 6:6:6 fertilizer containing 3% microelements and 50-60 ppm concentration of nitrogen (about 750 ml per cubic meter) started immediately after germination. Irrigation regime was 2 cubic meters per hectare per day once every two days. After beginning of flowering, fertilization with a 4:2:6 fertilizer was performed with a dose of 100 ppm nitrogen, i.e. two liters per cubic meter. Water quantities rise to 3 cubic meters per day in March, and up to five cubic meters per day in April.

Harvesting of tubers begins in late April early May and ends in mid-May. Harvesting is done by manual excavation and removal of tubers. A seed collection step (April) to be used for next season (December) is performed prior to tuber harvesting. Total growing protocol takes approximately 5 months.

*Erodium crassifolium* and *Cucurbita pepo* Extracts
Ethyl Acetate Extraction

Bulbs collected from Ramat Negev and stored in dark room, at room temperature after collection in the field, were frozen at −80° C. Twenty five grams of frozen bulbs were blended in a blender at top speed for 1 min in acetone (1:5 w/v), extracted in ethyl acetate and washed with potassium phosphate buffer (0.2 M, pH 8.3). Extracts were dried over anhydrous $Na_2SO_4$ and concentrated in vacuo and stored at −20° C. for further analysis.

Extraction in Solvents with Different Polarity Traits

Four different solvents with different polarity traits were used for extractions: $H_2O$—the most hydrophilic solvent, 70% ETOH or Acetonitrile:Methanol (1:1) for medium polar solvents and Hexane:Ethyl:Acetate (1:1) for hydrophobic solvents. *Erodium crassifolium* bulbs were crushed using a mortar and pestle. For extractions using water, two grams of the crushed material were transferred to a 15 ml falcon tube and 4 ml of water were added. For the other solvents, two grams of the crushed material were transferred to 50 ml falcon tubes and 20 ml of the corresponding solvent were added. All tubes were incubated overnight at 28° C. with shaking at 180 rpm. Tubes for water extraction were stored at 4° C. prior to drying. The dried material was stored for further analysis. Tubes containing the other solvents were centrifuged for 5 minutes at 2500 rpm. Equal volumes of the supernatant was transferred to two 15 ml falcon tubes that were then dried and concentrated in vacuo overnight and stored at −20° C. for further analysis.

For extracts which were prepared with either 70% ETOH, Acetonitrile:Methanol (1:1) or Hexane:Ethyl:Acetate (1:1), the dried material was dissolved in 100 μl of the solvent used for extraction followed by addition of 900 μl of culture media (McCoy's 5a Medium Modified or DMEM). The obtained solution was then spun for 1 min at 14,000 rpm followed by filtration through a 0.45 μm. For water extracts, 1 ml double distilled water was added to the dried extracts which were then filtered using a 0.45 μm filter. *Curcubita pepo* extractions in water were carried out similarly. Unless stated differently, cells were treated with a 1:10 dilution of plant extracts.

Determination of Dry Weight

One (1) gr of crushed material was wrapped in aluminum foil and the total weight was recorded. After overnight incubation at 60° C., the material was reweighed.

Preparation of *Curcuma longa* Solutions

A 400 mg commercial pill of *Curcuma longa* extract was dissolved in 1 ml of Dimethyl sulfoxide (DMSO). 100 μl of this solution were mixed with 900 μl of Acetonitrile:Methanol (1:1) and used as a positive control.

Cell Culture Growth

HCT-116 (ATCC CCL-247) or HT-29 (ATCC HT-B38) colon cells, BJ-hTERT fibroblast (ATCC, CRL-4001), HaCaT (keratinocytes) skin cells or MDA-MB-231 breast cancer cells were grown at 37° C. in a humidified 5% $CO_2$, 95% air atmosphere. HCT-116 and HT-29 cells were maintained in McCoy's 5a Medium Modified while BJ-hTERT, HaCaT and MDA-MB-231 cells were cultured in DMEM supplemented with 10% fetal bovine serum (FBS).

Determination of Anti-Inflammatory Activity
Excitation and Treatment of Cells

Cells were seeded in 24-well plates at 50,000 cells per well in triplicate in 500 μl of the appropriate culture medium. The cells were incubated for 24 h at 37° C. in a humidified 5% $CO_2$-95% air atmosphere. Unless stated differently, cells were treated with a 1:10 dilution of plant extracts.

For analyzing the formulated creams prepared for *Erodium* water extracts, 250 mg of each cream were diluted in 750 μl water. 50 μl of the prepared solution (~1:12 dilution) was added per well in order to test for anti-inflammatory activity.

For analyzing the anti-pollutant effect of *Erodium* water extracts, UVC or $H_2O_2$ treated cells were prepared.

TNF-α Activation (TNF-α)

cultures in each well were treated with 50 ng/ml recombinant human TNF-α (Peprotech, Cat. #300-01A) and 50 μl (1:10 dilution) of plant extract as described above. Since the culture cells used are known to produce baseline level of interleukin 8 (IL-8) in the absence of TNF-α, three different controls were included in all experiments: (a) wells without TNF-α and without plant extracts, (b) wells in which only TNF-α was added, (c) wells with both TNF-α and the relevant solvent. In addition, extracts of *Curcuma longa* and *Curcubita pepo* (Pumpkin) were added to wells containing TNF-α to serve as positive and negative controls, respectively. Cultures were then incubated again at the same conditions for 16 h before IL-8 level were determined.

Lipopolysaccharide (LPS) Excitation

LPS powder (Sigma, Cat. #L8274) was dissolved in water at a concentration of 1 mg/ml. Then, 75 μl of this working solution were added to each well resulting in a final concentration of 150 ng/ml. Volume adjustment was performed for all wells.

UVC Treatment

Twenty-four (24)-well plates were placed open on an elevated stage (19.5 cm elevation) inside the laminar hood. Cells (both treated or not treated with *Erodium* water extract) were exposed to UVC for 60 or 120 minutes.

$H_2O_2$ Treatment $H_2O_2$ was added to treated or untreated *Erodium* water extract. The final concentration of was 3.2 mM.

Determination of IL Levels Produced by Cells

IL-8 levels was determined by the DuoSet® ELISA kit (Human CXCL8/IL-8, Cat #DY208-05) according to manufacturer's protocol (R&D Systems). Using a seven point standard curve, the levels of IL-8 (pg/ml) in each well were calculated. For specific activity calculations, the values obtained in wells with plant extracts were subtracted from the values received in the wells containing the control solvent. The net values were then divided by the relevant dry weight of each sample in order to obtain specific activity. Means of replicates were subjected to statistical analysis by multiple comparison Tukey-Kramer test ($P \leq 0.05$). Levels of TNF-α (Cat. #DY210-05), IL-6 (Cat. #DY206-05), IL-12 (Cat. #DY1270-05) and IL-27 (Cat. #DY2526-05) were evaluated using similar kits manufactured by R&D Systems.

XTT Viability Assay

Cells were seeded in 96-well plates at 10,000 cells per well in triplicate in the appropriate cell culture media and incubated for 24 h at 37° C. in a humidified 5% $CO_2$—95% air atmosphere. The following day, the extracts were added to each well. Wells with media but no cells served as controls. Cells were incubated for 16 hours. XTT (2,3,-bis (2-methoxy-4-nitro-5-sulfophenyl)-5-[(phenylamino)-carbonyl]-2H-tetrazolium inner salt) reduction was used to quantify viability according to manufacturer's instruction (BI, Kibbutz Beit-Haemek, Israel). Cells were incubated with XTT reagent for 2 hours at 37° C. in a humidified 5% $CO_2$-95% air atmosphere. Absorbance was recorded by a photometer SPEKTRAFluor Plus (Tecan, Salzburg, Austria) at 490 nm with 650 nm of reference wavelength. Cell survival was estimated from the equation: % cell survival=100×(At−Ac), where At and Ac are the absorbencies (490 nm) of the XTT colorimetric reaction (BI, Kibbutz Beit-Haemek, Israel) in treated and control cultures, respectively, minus non-specific absorption measured at 650 nm. Absorbance of medium alone was also deducted from specific readings.

Preparation of Drug Solutions for ELISA Assays

Prednisolone (Sigma, P6004-1G) and Indomethacin were used in order to evaluate the anti-inflammatory activity of *Erodium crassifolium* extracts. Prednisolone solution was prepared by dissolving 7.2 mg in 1 ml ETOH (20 mM). 50 µl of this solution were added to each tested well. Due to the instability of this solution, this drug was replaced with 6α-Methylprednisolone, a stable sodium salt of prednisolone. Working solution for this salt was prepared by dissolving 9.93 mg in 1 ml water (20 mM). 50 µl of this solution were added to each tested well. For Indomethacin, a 25 mg pill was dissolved in 1 ml DMSO. Fifty µl of this solution were added to each tested well.

Antioxidants Activity Assays

1. OxiSelect™ Oxygen Radical Antioxidant Capacity (ORAC) Activity Assay (Cat #STA-345-T) was used for in vitro testing. This assay is based on the oxidation of a fluorescent probe by peroxyl radicals by way of a hydrogen atom transfer (HAT) process. Peroxyl radicals are produced by a free radical initiator, which quenches the fluorescent probe over time. Antioxidants present in the assay block the peroxyl radical oxidation of the fluorescent probe until the antioxidant activity in the sample is depleted. The remaining peroxyl radicals destroy the fluorescence of the fluorescent probe. In this assay, both the antioxidant's inhibition time and inhibition percentage of free radical damage is a single value. The sample antioxidant capacity correlates to the fluorescence decay curve, which is represented as the area under the curve (AUC). The AUC is used to quantify the total peroxyl radical antioxidant activity in a sample and is compared to an antioxidant standard curve of the water soluble vitamin E analog Trolox™. The assay was performed according to manufacturer instructions (Cell Biolabs Inc.).

2. Antioxidant activity was also measured using the OxiSelect™ Cellular Antioxidant Assay (Cat #STA-349) manufactured by Cell Biolabs. 60,000 cells per well were cultured in a 96-well black fluorescence cell culture plate until confluent. Then the cells were pre-incubated with a cell-permeable DCFH-DA fluorescence probe dye and the bioflavonoid Quercetin, or the antioxidant sample being tested. After a brief incubation, the cells were washed, and the reaction started by adding the free radical initiator. This reagent creates free radicals that convert the probe to highly fluorescent DCF. Quercetin or the antioxidant sample inhibits the formation of free radicals, and thus DCF formation, in a concentration dependent manner. Fluorescence was measured over time in a standard microplate fluorometer. This fluorescence correlates to the Quercetin's ability to quench free radicals. Test antioxidant values can be compared to Quercetin to determine antioxidant activity within the cell. The assay was performed according to manufacturer instructions.

Quantitative Real-Time Polymerase Chain Reaction (qRT-PCR)

Cells were seeded in 6-well plates at a concentration 1,500,000 cells per well. After a 24 h incubation at 37° C. in a humidified 5% $CO_2$-95% air atmosphere, cells were treated with TNF-α (final concentration of 1 ng/ml) followed by treatment with *Erodium* water extract (Erod15 and Erod30 are 15× and 30× dilutions respectively). Non-treated cells or cells treated only with TNF-α served as negative and positive controls. Cells were then re-incubated for 24 h at 37° C. in a humidified 5% $CO_2$—95% air atmosphere. The next day, cells were harvested, and total RNA was extracted using Trizol (Invitrogen, Carlsbad, CA, USA) according to the manufacturer's protocol. Two micrograms of RNA was reverse-transcribed in a total volume of 20 µl using the High Capacity cDNA kit (Invitrogen). MMP-9 Primers were designed using Primer3Plus software. PCR was performed in triplicate using a Rotor-Gene 6000 (Corbett Life Sciences) and SYBR Green (Invitrogen, Foster City, CA) according to the manufacturer's protocol. The expression of each target gene was normalized to the expression of GAPDH mRNA and is presented as the ratio of the target gene to GAPDH RNA, expressed as 2-ΔCt, where Ct is the threshold cycle and ΔCt=Ct Target−Ct GAPDH. Experiments were repeated three times.

Fractionation of *Erodium* Water Extract Through High Performance Liquid Chromatography (HPLC)

Sample Preparation

The concentrated *Erodium* extract was dissolved in deionized water and filtered through 0.45 um syringe filter. The filtered extract was loaded in HPLC for separation. The concentrated *Erodium* extract was dissolved in deionized water and filtered through 0.45 µm syringe filter. The filtered extract was loaded in HPLC for separation. The hydrolyzed extract was treated with 2 N HCL in 1:1 proportion and incubated at 80° C. for one hour prior to HPLC run.

HPLC Separation

The separation of the sample was carried out with Ultimate 3000 HPLC system coupled with WPS-3000(T) Autosampler, HPG-3400 pump, DAD-300 detector. The separation was performed on a Purospher RP-18 endcapped column (250 mm×4.6 mm I.D.; Merck KGaA, Darmstadt, Germany) with a guard column (4 mm×4 mm ID.). Solvent gradients were formed by varying the proportion of solvent A [water (0.1% acetic acid)] to solvent B (methanol) with the flow rate of 1.0 ml/min. Initially Solvent B was maintained at 10% for 10 min and then subsequently increased to 45% in 25 min. The 45% of Solvent B was maintained for 5 min and then decreased to 10% in 10 minutes and equilibrated for 5 min. The compounds peaks were detected with three different wavelengths—220 nm, 240 nm and 280 nm.

Statistical Analyses

Results are presented as mean and S.E. of replicate analyses and are either representative of, or inclusive of at least 2 independent experiments. Means of replicates were subjected to statistical analysis by Tukey-Kramer test (P≤0.05) using the JMP statistical package and regarded as being significant when P≤0.05 (*). GraphPad Prism (version 6 for windows, GraphPad software Inc. San Diego, USA) was employed to produce dose-response curve and $IC_{50}$ doses for *Erodium* extracts by performing nonlinear regression analysis.

Human Cell Culture

HaCaT (ATCC-HB-241) normal skin cells were grown at 37° C. in a humidified 5% $CO_2$-95% air atmosphere. Cells were maintained in Dulbecco's Modified Eagle Medium (DMEM, Biological Industries, 01-055-1A, Israel) with 10% fetal bovine serum (FBS, Biological Industries, 04-007-1A, Israel) and Penicillin (100 units/mL)—Streptomycin (100 μg/mL) solution (Biological Industries, 03-031-1B, Israel).

Chemical Standards (−)-Epigallocatechin (Sigma-Aldrich, 08108, Switzerland), catechin (Sigma-Aldrich, U-49040, USA) and gallic acid (Sigma-Aldrich, 91215, Switzerland) were purchased from Sigma-Aldrich.

*Erodium crassifolium* Growth Conditions

The seeds were planted in 1.2 meter plowed sandy soil beds, in an open field in late November 2016 in Ramat Negev, Israel (30° 58'N 34° 42'E). The plant growth period is from November to May, with maximum average temperatures of 25.3 to 32.9° C. Each bed had two lines of drip irrigation with drippers spaced every 20 cm and a flow rate of 1.6 L/h. Two seeds were planted on either side of each dripper. Prior to germination the field was irrigated with 60 $m^3$ of non-fertilized water (EC: 0.7 ms/cm)/d/hec. Germination occurred about 2 weeks after planting. After germination, the irrigation was lowered to 40 $m^3$/d/hec and continuous fertilization was applied for 3 weeks as 1 L/$m^3$ water with liquid fertilizer Shefer 6:6:6 (Israel Chemicals LTD), which was added via the irrigation system. After an additional month the fertilizer was changed to Shefer 4:2:6 (35% ammonium and 65% nitrate) (Israel Chemicals LTD) at a concentration of 1.5 L/$m^3$ water. Flowering began in April and continued until June. The tubers formed underground from the early stages of plant growth and were harvested after 7 months when most of the flowers in the field had turned into seeds. Tubers were placed in cold storage (−20° C.). One gram of crushed material was wrapped in aluminum foil and the total weight was recorded. After overnight incubation at 60° C., the dried material was weighed together with the foil to calculate dry weight.

*Erodium crassifolium* Extraction with 70% Ethanol

*E. crassifolium* tubers were removed from cold storage (−20° C.) and frozen in liquid nitrogen. The frozen tubers were crushed using an electrical blender and weighed. For each 1 g of fresh material, 4 mL of 70% ethanol were added immediately to the crushed tubers and incubated overnight at 28° C. with shaking at 180 rpm, after which the samples were centrifuged for 5 min at 5,000 rpm. The supernatant was transferred to new tubes. The solvent was evaporated in vacuo overnight. The remaining water content was lyophilized to powder and stored at −20° C. From each gram of tuber approx. 60 mg of lyophilized extract was obtained. To conduct further analysis the lyophilized material was weighted and dissolved in 100 μL of 70% ethanol and then 900 μL of double distilled water (DDW) to obtain 60 mg/mL. This preparation was made just before the analysis and filtered through a 0.45 μm membrane. The filtrate was diluted or not for further testing as described below.

Determination of Interleukin 8 (IL-8) Levels in HaCaT Cells

HaCaT Cells were seeded into 24-well plates at 50,000 cells per well in triplicate in 500 μL of media and then incubated for 24 h at 37° C. in a humidified 5% $CO_2$-95% air atmosphere. After incubation, cell excitation was performed with recombinant human tumor necrosis factor-α (TNF-α, PeproTech, 300-01A, USA). Cultures in each well were treated with a final concentration of 50 ng/mL of TNFα and 50 μL plant extract. Three different controls were included in all experiments: (a) non-treated cells, with neither TNF-α nor plant extracts, (b) cells treated with TNF-α alone, (c) cells treated with TNF-α and the solvent (7% ethanol). The supernatant was collected, and the level of IL-8 was measured 16 h post-treatment using the commercial Human CXCL8/IL-8 DuoSet ELISA kit (R&D Systems, DY208-05, USA) according to the manufacturer's protocol. IL-8 is a common biomarker for inflammatory skin diseases. 16 h of TNF-α exposure induce IL-8 levels. Dexamethasone (Sigma-Aldrich, D4902, USA) was used as a positive control.

Measurement of Cytotoxicity and Determination of $IC_{50}$

Resazurin (R&D Systems, AR002, USA) was used to calculate the number and percentage of live cells in each treatment. For this, 10% Resazurin was added to each well 16 h post-treatment. The plate was then incubated for 4 h at 37° C. in a humidified 5% $CO_2$—95% air atmosphere. The supernatant (100 μL) from each well was subsequently transferred to a 96-well plate and the relative fluorescence at the excitation/emission of 544/590 nm was measured. The number of live cells was calculated with a linear standard curve built by seeding different concentrations of cells in 24-well plates treated with Resazurin. GraphPad Prism software was used to calculate the $IC_{50}$ value using nonlinear regression analysis.

Determination of In Vitro Anti-Oxidant Activity

Anti-oxidant activity was determined using the OxiSelect™ Oxygen Radical Antioxidant Capacity (ORAC) Activity Assay (Cell Biolabs, Inc., STA-345, USA) according to the manufacturer's instruction. A decoction of green tea was used as a positive control and compared with the crude extract. Half a gram (0.5 g) of green tea powder was taken in 20 mL of distilled water and incubated in a boiling water bath for 5 min and this extract was further diluted 1,000 times before the analysis. The results were expressed in mmol Trolox equivalence.

Treatment of Cells with UVB Irradiation

HaCaT cells were plated at a concentration of 1×$10^4$ cells/0.1 mL in a 96-microwell plate for 24 h. To prevent light absorption by the tissue culture medium, the medium was removed, and the treatments were added with fresh PBS to each well in different concentrations. The cells were then exposed to UVB irradiation (6 J/$m^2$/min) from lamps (wavelength=253.7 nm) placed 20.5 cm above the plate. The medium was immediately replaced with fresh complete DMEM either with or without extract and cells were cultured for a further 16 h at 37° C. in an incubator with 5% $CO_2$ to determine the level of IL-8 at 3 time points (0, 2, and 3 min) of UVB exposure at the above specified intensity. The results were normalized based on the number of viable cells due to the cytotoxic effect of UVB, which was measured simultaneously (as described above using the Resazurin assay). Thus the values expressed as level of IL-8 per cell.

Quantitative Real-Time Polymerase Chain Reaction (qRT-PCR)

Cells were seeded into a 6-well plate at a concentration $1.5 \times 10^6$ cells per mL per well. After 24 h incubation at 37° C. in a humidified 5% $CO_2$—95% air atmosphere, cells were treated with TNF-α (final concentration of 400 ng/mL) followed by treatment with F4 with an $IC_{50}$ concentration. Non-treated cells or cells treated only with TNF-α served as negative and positive controls respectively. Cells were then re-incubated for 24 h at 37° C. in a humidified 5% $CO_2$—95% air atmosphere. Cells were harvested the next day and total RNA was extracted using a TRI reagent (Sigma-Aldrich, T9424, USA) according to the manufacturer's protocol. RNA was reverse-transcribed (2.5 μg) in a total volume of 20 μL using Maxima reverse transcriptase (TAMAR OEM, Israel) according to the manufacturer's protocol. All primers were designed using Primer 3 Plus software. PCR was performed in triplicate using a Rotor-Gene 6000 instrument (QIAGEN, Zurich, Switzerland) and Maxima SyGreen Mix (Thermo Scientific, USA) according to the manufacturer's protocol. The expression of each target gene was normalized to the expression of GAPDH mRNA in the $2^{-\Delta\Delta Ct}$ method and is presented as the ratio of the target gene to GAPDH mRNA, where Ct is the threshold cycle and ΔCt=(Ct Target gene—Ct GAPDH). Experiments were independently repeated three times. The primers were: For MMP9 (forward) 5'-TTGACAGCGACAAGAAGTGG-3' (SEQ ID NO: 1) and (reverse) 5'-TCACGTCGTCCT-TATGCAAG-3' (SEQ ID NO: 2) and for MMP3 (forward) 5'-GCAGTTTGCTCAGCCTATC-3' (SEQ ID NO: 3) and (reverse) 5'-TCACCTCCAATCCAAGGAAC-3' (SEQ ID NO: 4), and for GAPDH (forward) 5'-CAGCCTCAAGAT-CATCAGCA-3' (SEQ ID NO: 5) and (reverse) 5'-TGTGGT-CATGAGTCCTTCCA-3'(SEQ ID NO: 6).

High-Performance Liquid Chromatography (HPLC) Analysis

The lyophilized EE was dissolved as described above and filtered through a 0.45 μm syringe filter. The filtered extract was loaded into the HPLC for separation. The separation of the sample was carried out with an Ultimate 3000 HPLC system coupled with a WPS-3000(T) Autosampler, HPG-3400 pump, and DAD-300 detector. The separation was performed using a Purospher RP-18 endcapped column (250 mm×4.6 mm I.D.; Merck KGaA, Darmstadt, Germany) with a guard column (4 mm×4 mm ID.). Solvent gradients were formed by varying the proportion of solvent A [water with 0.1% acetic acid (v/v)] to solvent B (methanol) with the flow rate of 1.0 mL/min. Solvent B was maintained initially at 10% for 5 min and then increased to 100% in 25 min. This 100% of Solvent B was maintained for 10 min, then decreased to 10% in 10 minutes and equilibrated for 5 min (total run time 55 min). The compound peaks were detected at three different wavelengths: 220, 240 and 280 nm. The same program was used to obtain fractions in bulk using preparative HPLC (11250 Infinity, Agilent Technologies) using reversed-phase C18 column (Kinetex 5u EVO C18-100A–250×21.2 mm). After collection, the fractions were dried to powder by lyophilization. These lyophilized fractions were re-suspended in 7% ethanol as described above and checked for their effect on IL-8 levels as described above. Further analyses were carried out to correlate the activity and peak profile for detecting the active compound peak(s).

Gas Chromatography Mass Spectrometry (GC/MS) Analysis

GC/MS analyses were carried out using a HP7890 gas chromatograph coupled to a HP6973 mass spectrometer (electron multiplier potential 2 KV, filament current 0.35 mA, electron energy 70 eV, and the spectra were recorded over the range m/z 45 to 1,000).

An Agilent 7683 autosampler was used for sample introduction. Helium was used as a carrier gas at a constant flow of 1.1 ml s$^{-1}$. One (1) μl of each sample was injected into the GC/MS using a 1:10 split ratio injection mode. An isothermal hold at 50° C. was kept for 2 min, followed by a heating gradient of 6° C. min$^{-1}$ to 300° C., with the final temperature held for 4 minutes. A 30 m, 0.25 mm ID 5% cross-linked phenylmethyl siloxane capillary column (HP-5MS) with a 0.25 m film thickness was used for separation and the injection port temperature was 220° C. The MS interface temperature was 280° C. Peak assignments were carried out with the aid of library spectra (NIST 14.0) and compared with published data and MS data obtained from the injection of standards purchased from Sigma-Aldrich.

Derivatization Procedure

Prior to GC/MS analysis, 200 μL of N,O-bis(trimethylsi-lyl)trifluoroacetamide (BSTFA, Sigma-Aldrich, T-6381, USA) containing 1% of trimethylchlorosilane (TMCS) was added to each completely dried extract and heated to 70° C. for 20 minutes. One (1) L of each sample was injected into the GC/MS using a 1:10 split ratio injection mode, as described above.

Example 1

*Erodium crassifolium* Extracts have Anti-Inflammatory Activity

Figure 2A:
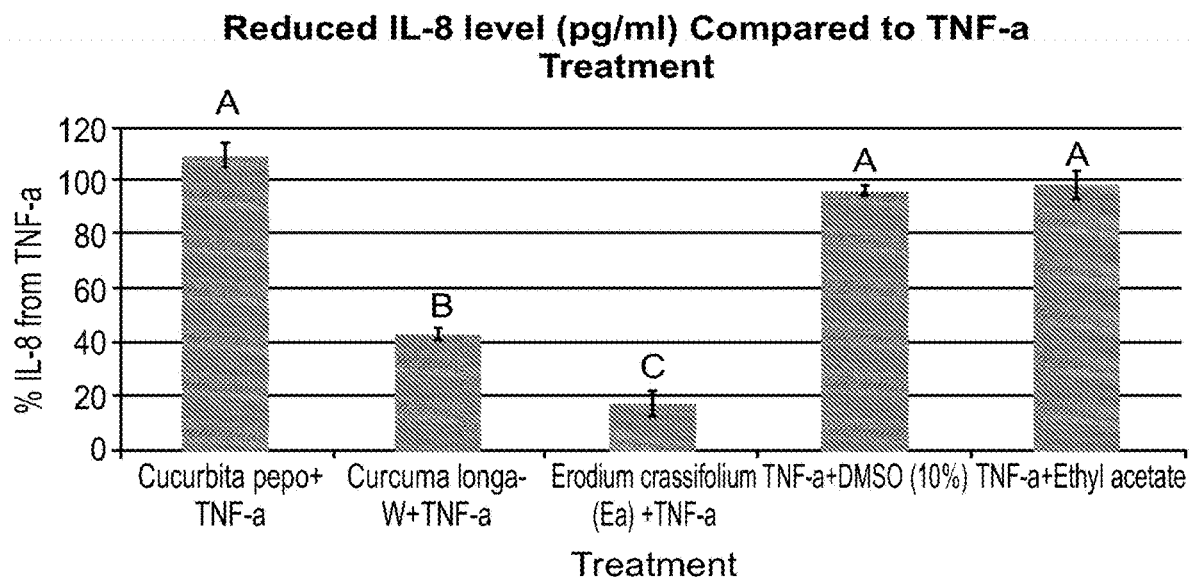
FIGS. 2A-2B include graphs showing that *Erodium crassifolium* extracts comprise anti-inflammatory activity. (2A) Reduced IL-8 level compared to TNF-α treatment. The level of IL-8 for each sample was calculated based on the obtained standard curve. The percentage of IL-8 level in relation to the control treatment (TNF-α) was calculated. (2B) Anti-inflammatory specific activity (pg/ml per 1 gr dry weight). Calculation was performed by dividing the activity obtained in (2A) by the dried weight. Means of replicates were subjected to statistical analysis by multiple comparison Tukey-Kramer test ($P \leq 0.05$). Levels not connected by same letter are significantly different. Ea=Ethyl acetate; W=Water (10% DMSO); *Cucurbita pepo*—extraction in Ea.
Figure 2B:
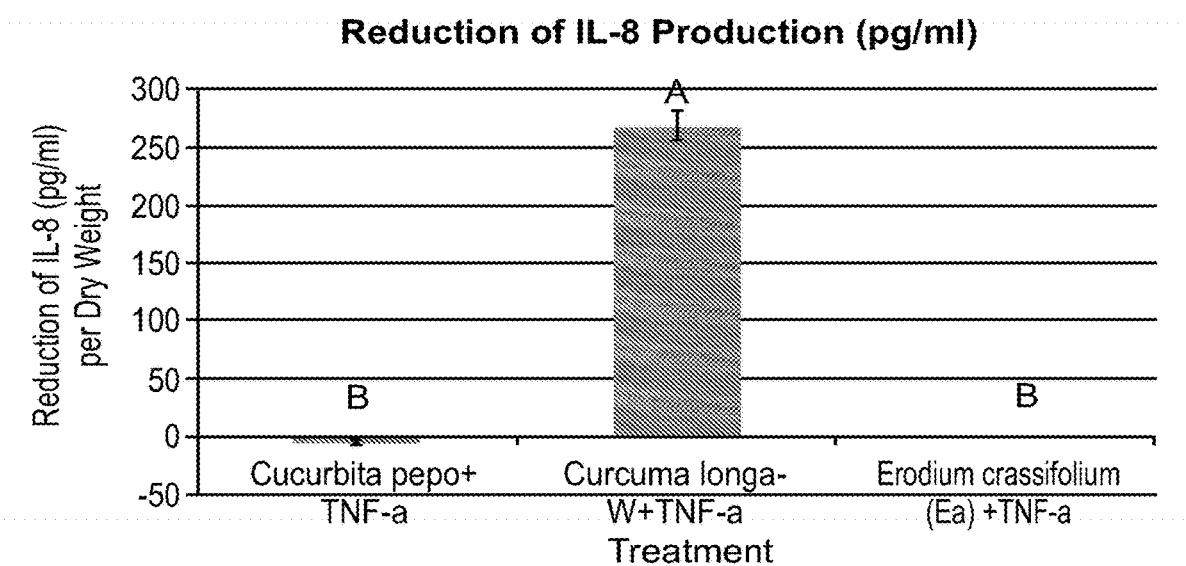

In order to test whether bulbs of *E. crassifolium* comprise anti-inflammatory activity, the effect of tuber extracts on HCT-116 human colon cells which were stimulated with TNF-α were compared to the effect of commercial pills of *Curcuma longa* (positive control) or extracts from *Curcubita pepo* (negative control). As seen in FIGS. 2A-2B extracts of *E. crassifolium* reduced the amount of IL-8 secreted by the TNF-α stimulated cells.

In order to identify the *E. crassifolium* extract with the highest activity. HCT-116 human colon cells (FIG. 3A) or BJ-hTERT skin cells (FIG. 3B) were stimulated with TNF-α followed by treatment with *Erodium* extracts. *Curcuma longa* extract from commercial pills served as positive control. Curcubitapepo water extract was used as negative control.

As illustrated in FIGS. 3A-3B, the highest activity was obtained when extraction was carried out in water as exemplified in both colon and skin cells.

Example 2

Determination of $IC_{50}$ for *Erodium crassifolium* Extracts

In order to determine $IC_{50}$ for *E. crassifolium* extracts, XTT assays using different dilutions of the extract were performed in MDA-MB-231, HCT-116 and HaCaT cell lines (FIGS. 4A-4C).

In all three types of cells when the non-diluted extract was used, the majority of cells did not survive. However, in all three types a higher dilutions results in higher than 50% survival. According to $IC_{50}$ calculations, $IC_{50}$ values for the different types of cells are as follow: $IC_{50}$ MDA-MB-231=7.428; $IC_{50}$ HCT-116=13.55; $IC_{50}$ HaCaT (KER) =6.132. These calculations imply that each cell type reacts different to treatment with *Erodium* water extract. Also, it was noted that normal cells (HaCaT) are less sensitive than cancerous ones (HCT-116 and MDA-MB231). In all three cases the $IC_{50}$ obtained is higher or similar to than that used for inflammation assays. Since anti-inflammatory assays are performed using an approximately 11.5-fold dilution (50 µl extract in a total volume of 575 µl) the reported anti-inflammatory activity is obtained with extract concentrations below or similar to the $IC_{50}$. Thus, the *E. crassifolium* extracts are safe for use as nutraceuticals or for dermacosmetic products.

Example 3

Stability of *Erodium* Water Extracts at in Different Conditions and in Different Tuber Stages

*Erodium* extracts were prepared without drying and stored at either 4° C. or −20° C. Activity using the IL-8 reduction assay in colon HCT-116 cells was tested for different dilutions (1:20; 1:40; 1:80 and 1:160) prepared for the samples stored at either temperature (FIG. 5). Extracts of *Curcuma longa* (in ACN:MT) and *Cucurbita pepo* (in water) served as positive and negative controls respectively.

The experiment results show that the active compound/s are still active after diluting the extract 1:40 but the activity obtained for additional dilutions (1:80 and 1:160) is lower but not necessarily significantly different.

In another experiment, water *Erodium* extracts were treated as follows: the liquid *Erodium* water extract was divided into 4 equal portions. A sublimation step was carried out in order to dry the sample. After sublimation each portion was stored for 5 days at a different temperature—(−20° C.), 4° C., 20° C. and 37° C. and the activity of each portion was tested by the IL-8 ELISA test on HaCaT skin cells.

Figure 6:
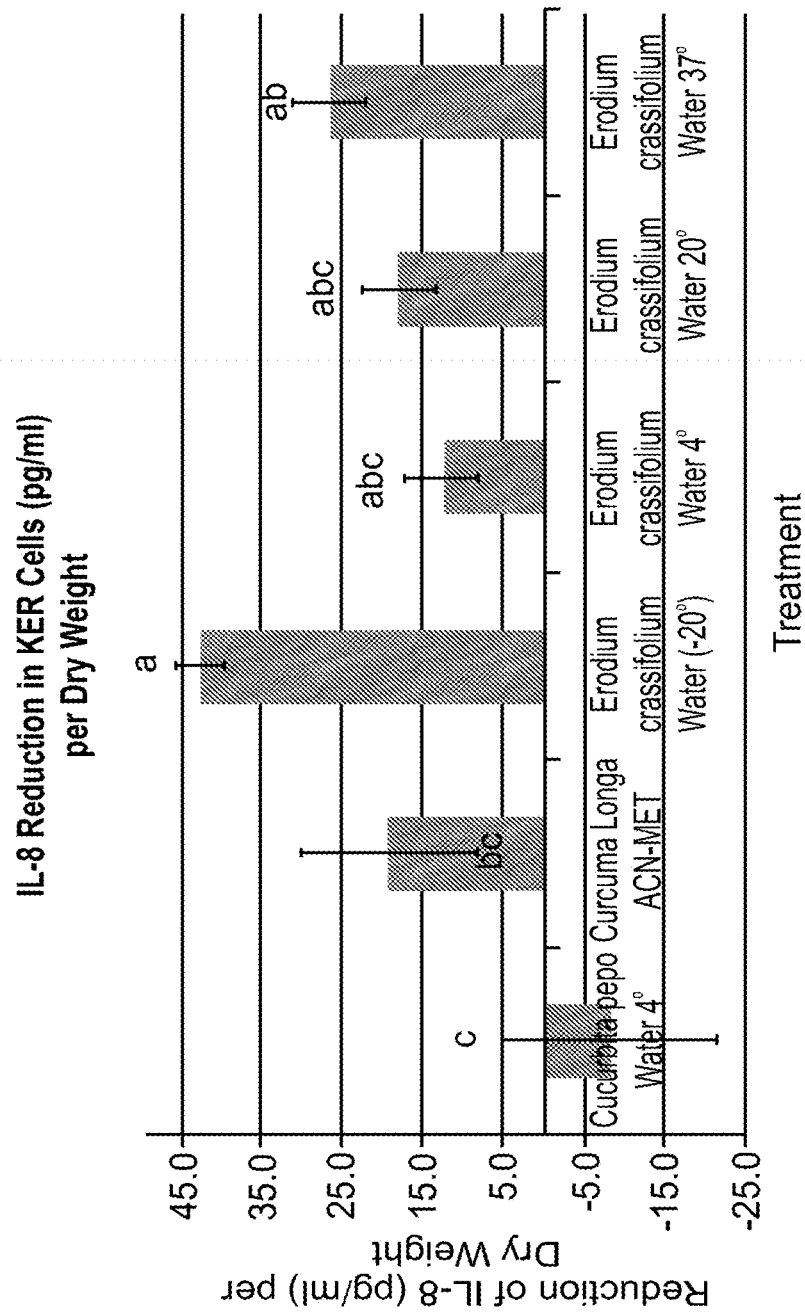
FIG. 6 is a graph illustrating the stability of *Erodium* extracts at different temperatures. Extracts were stored at (−20° C.), 4° C., 20° C. and 37° C. for a period 5 days before using for anti-inflammation assay in HaCaT skin cells. Levels not connected by same letter are significantly different. ACN-MET=Acetonitrile-Methanol (1:1).
Figure 7A:
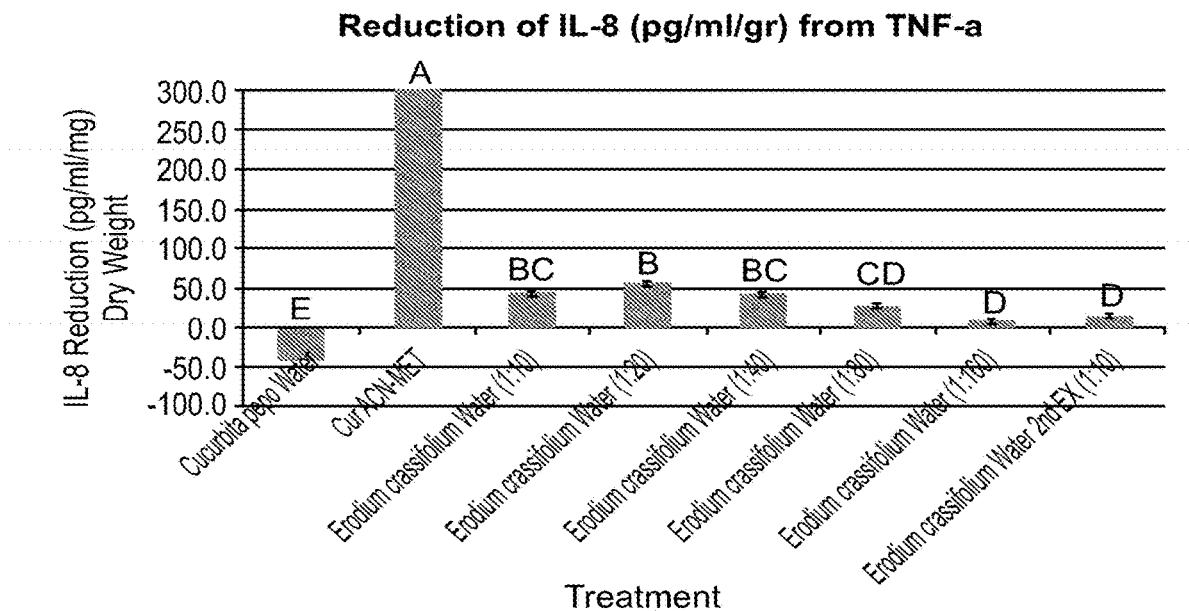
FIGS. 7A-7B include graphs illustrating the anti-inflammatory activity of diluted *Erodium* extracts. (7A) IL-8 ELISA assay in HCT-116 colon cells. (7B) IL-8 ELISA assay using BJ-hTERT skin cells. The ratios 1:10, 1:20, 1:40, 1:80 and 1:160 represent *Erodium* dilutions with water. Water 2nd EX (1:10) represents the second extraction cycle performed with the re-used *Erodium* mush. Levels not connected by same letter are significantly different. ACN-MET=Acetonitrile-Methanol (1:1). IL-8 reduction was calculated relatively to that obtained with cells stimulated only by TNF-α treatment.
Figure 7B:
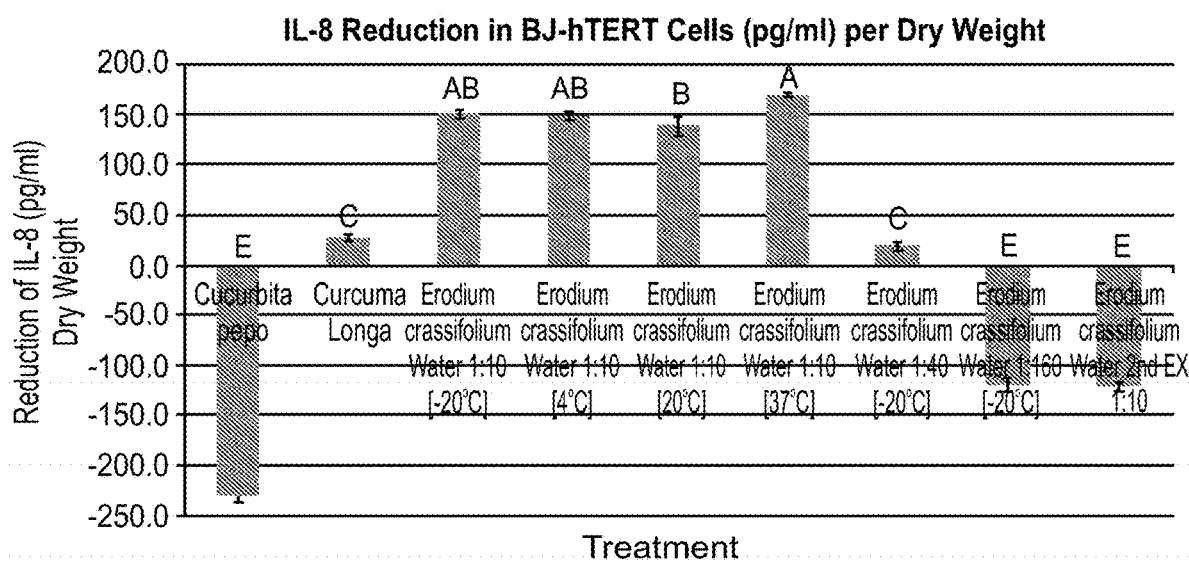

As illustrated in FIG. 6, the active compound/s are most stable when stored at (−20° C.). Higher temperatures resulted in less activity. Interestingly, increasing temperatures from 4° C. to 37° C. resulted in higher activity implying that this change in temperature might release or activate the active compound due to some process occurring in the extract. In a second experiment, the same dilutions previously used were prepared and re-tested using the dried extracts stored at (−20° C.) in both HCT-116 (FIG. 7A) and BJ-hTERT (FIG. 7B). In addition, a second extraction cycle, re-using the *Erodium* mush was tested.

Figure 8A:
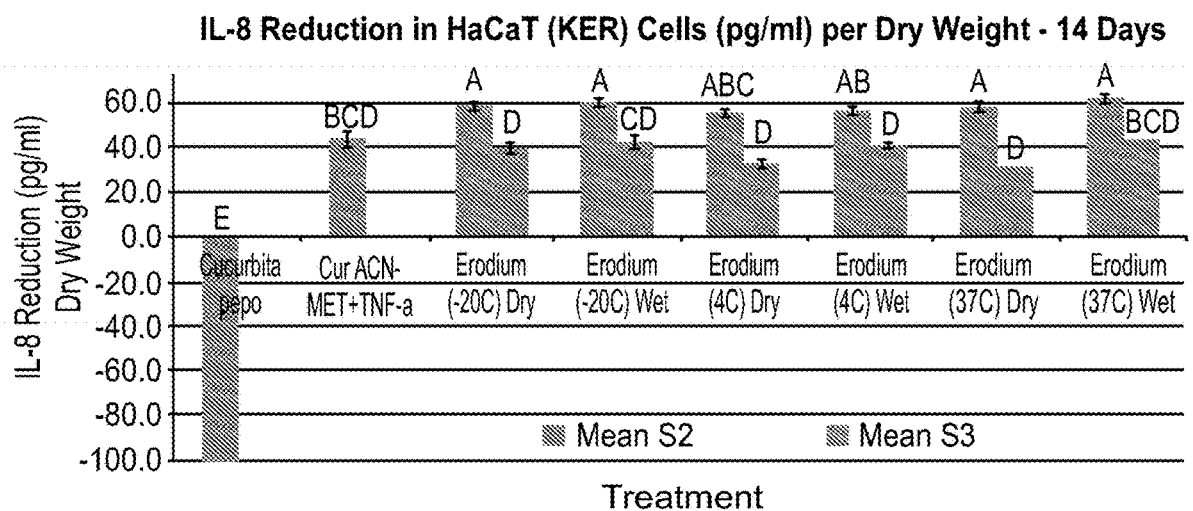
FIGS. 8A-8B include graphs illustrating the anti-inflammatory activity and stability in *Erodium* water extracts prepared from S2 and S3 tubers. IL-8 ELISA assay was performed on HaCaT (KER) skin cells. Following extraction, samples were stored either dry or wet (re-suspended in water after sublimation) at (−20° C.), 4° C. and 37° C. for a period for either 2 or 5 weeks. (8A) Activity and stability after 14 days. (8B) Activity and stability after 35 days. Levels not connected by same letter are significantly different. ACN-MET=Acetonitrile-Methanol (1:1).
Figure 8B:
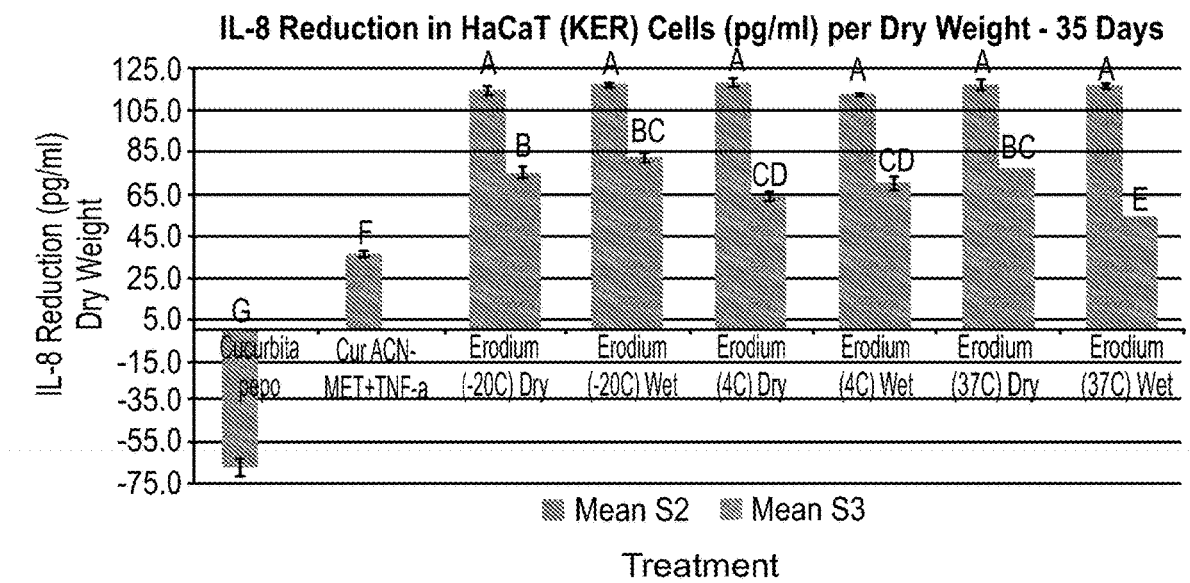

The production of anti-inflammatory compounds and their stability was also evaluated in two different tuber stages, S2 and S3. The classification to four different tuber stages depends on the size and color of tubers. The majority of tubers that were isolated from the soil belonged to stages S2 and S3. Since tubers are a storage organ, it is reasonable that the anti-inflammatory substances will be more abundant in these stages rather than in young tuber (S1) or mature ones (S4). Therefore, sublimated *Erodium* water extracts produced from S2 and S3 separately were stored dry or wet (re-suspended in water after sublimation) at (−20° C.), 4° C. and 37° C. for a period for either 2 or 5 weeks. At the end of each time period, stability and activity was tested by the IL-8 ELISA assay carried out on HaCaT (KER) skin cells (FIGS. 8A-8B).

As illustrated in FIGS. 7A-7B and 8A-8B modifying the extraction process by adding a sublimation step resulted in higher stability of the extracts regardless of whether samples were stored dry or wet. Furthermore, after sublimation, extracts were stable at all temperatures tested regardless to whether storage was in dry or wet conditions.

Example 4

Anti-Inflammatory Activity is Found in Both Peel and Flesh of *Erodium* Tubers

In order to determine whether the anti-inflammatory substances are synthesized in the tuber's peel or flesh, water extractions were prepared from both tissues. Anti-inflammatory activity was evaluated by the IL-8 ELISA assay in HaCaT (KER) skin cells.

Figure 9:
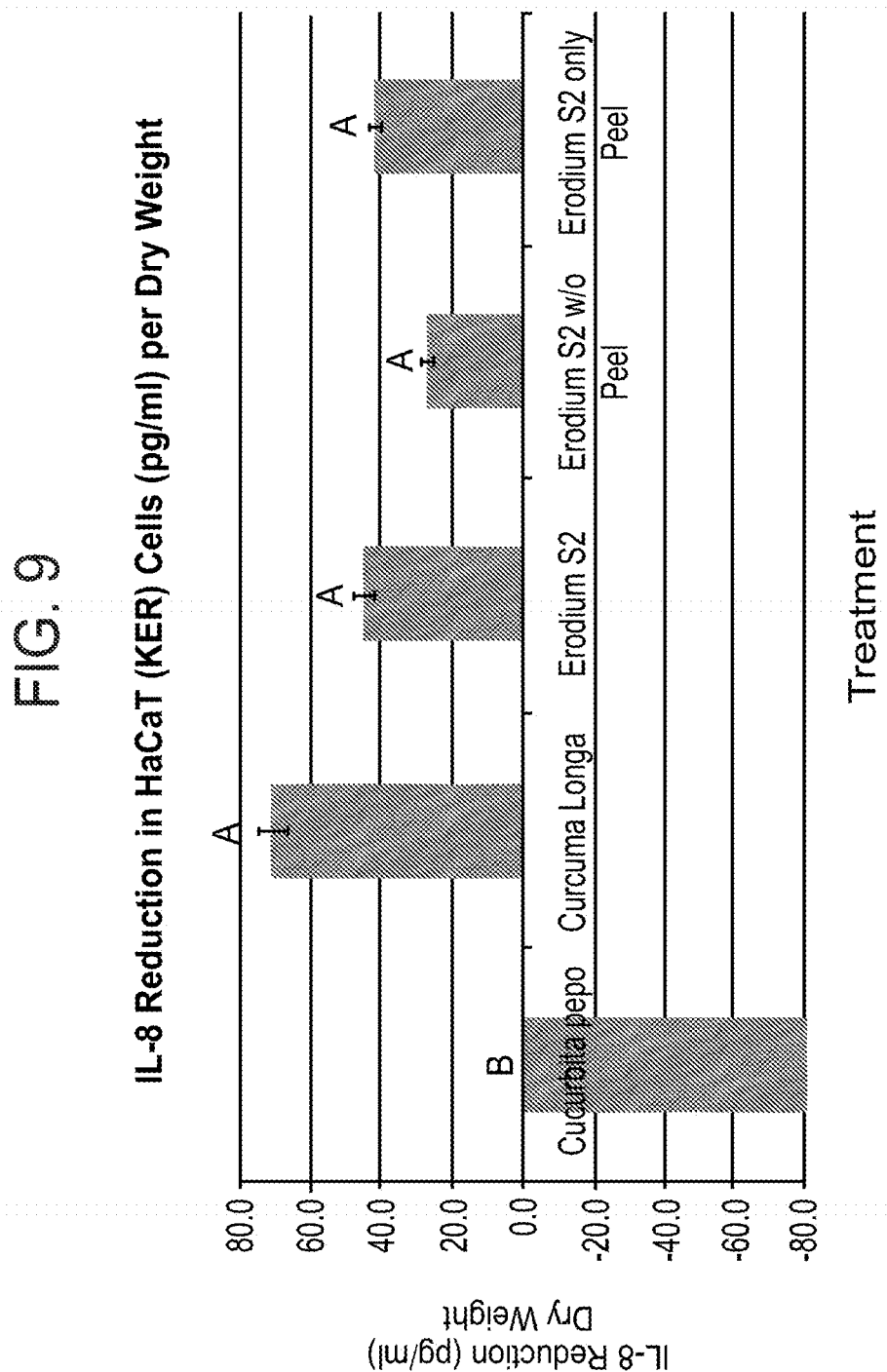
FIG. 9 includes a graph illustrating the presence of anti-inflammatory activity in both peel and flesh of *Erodium* tubers. Activity was evaluated by IL-8 ELISA assay performed on HaCaT (KER) skin cells. Levels not connected by same letter are significantly different. ACN-MET=Acetonitrile-Methanol (1:1).

As illustrated in FIG. 9, anti-inflammatory activity was found in both tuber's peel and flesh.

Example 5

Anti-Inflammatory Activity was Found in *Erodium* Leaves and Wildtype Strain

Extracts were prepared from WT *Erodium* tubers (FIG. 10A) of from leaves of cultivates plants (FIG. 10B). Activity was evaluated by the reduction levels of IL-8 in HaCaT (KER) skin cells. As illustrated in FIGS. 10A-10B, both leaves of cultivated *Erodium* and WT *Erodium* tubers possessed anti-inflammatory activity.

Example 6

Comparison of *Erodium* Water Extracts with Prednisolone and NSAID Indomethacin

As illustrated in FIGS. 11A-11B, the highest reduction in IL-8 levels when tested skin cells were obtained with *Erodium* extract. Furthermore, these levels were significantly different from those obtained with either prednisolone, indomethacin or the *Curcuma longa*, the positive control.

Example 7

*Erodium* Water Extracts Alleviates Inflammation Caused by Lipopolysaccharides

Many case of inflammation are triggered by the presence of microorganisms found in the inflamed tissue. These microorganisms either secret different compounds or contains molecules such as lipopolysaccharides that elicit the inflammation process. The cytokine IL-8 is known to be part of the body response to such microorganism invasion. Its expression is induced after a cascade of reactions occurring upon identification of lipopolysaccharides (LPS) by the body. Several other important molecules, including TNF-α and NF-κB are part of this cascade event. Since TNF-α and IL-8 expression occurs at different time points along the inflammation process it was important to identify their expression peaks in the present system. Therefore, experiment analyzing the timing of expression for both TNF-α and IL-8 and further analyzing whether *Erodium* extracts can alleviate inflammation triggered by LPS were carried out.

Figure 12A:
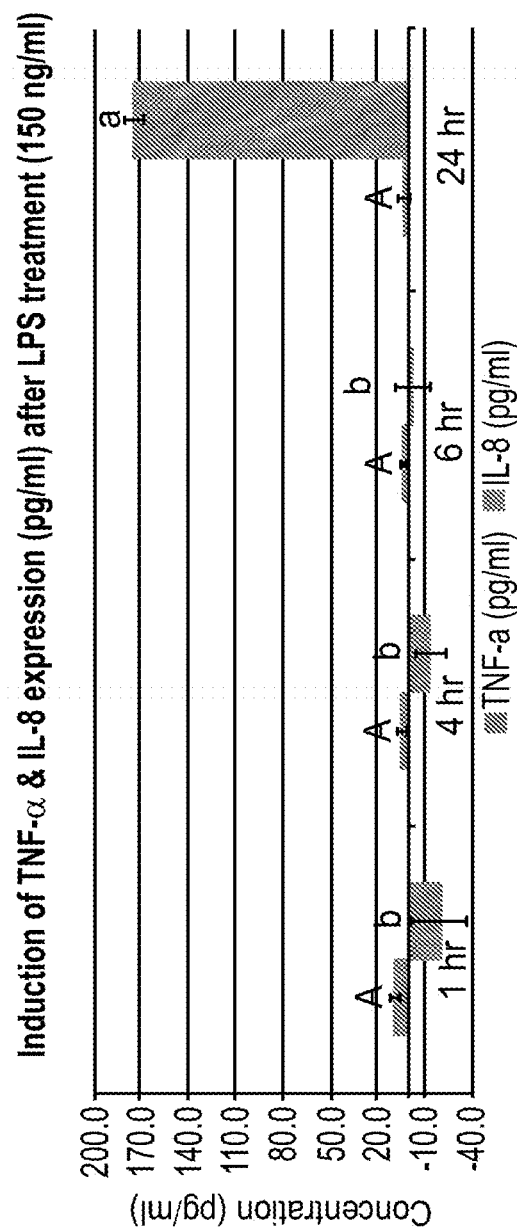
FIGS. 12A-12B include graphs showing that *Erodium* water extracts alleviate inflammation caused by LPS on HCT-116 colon cells. (12A) Expression of TNF-α and IL-8 during inflammation was evaluated at different time points (1, 4, 6 and 24 hr) after LPS treatment using the matching ELISA kit. (12B) Cells were excited using 150 ng/ml LPS and treated with *Erodium* water extract. Levels not connected by same letter are significantly different.
Figure 12B:
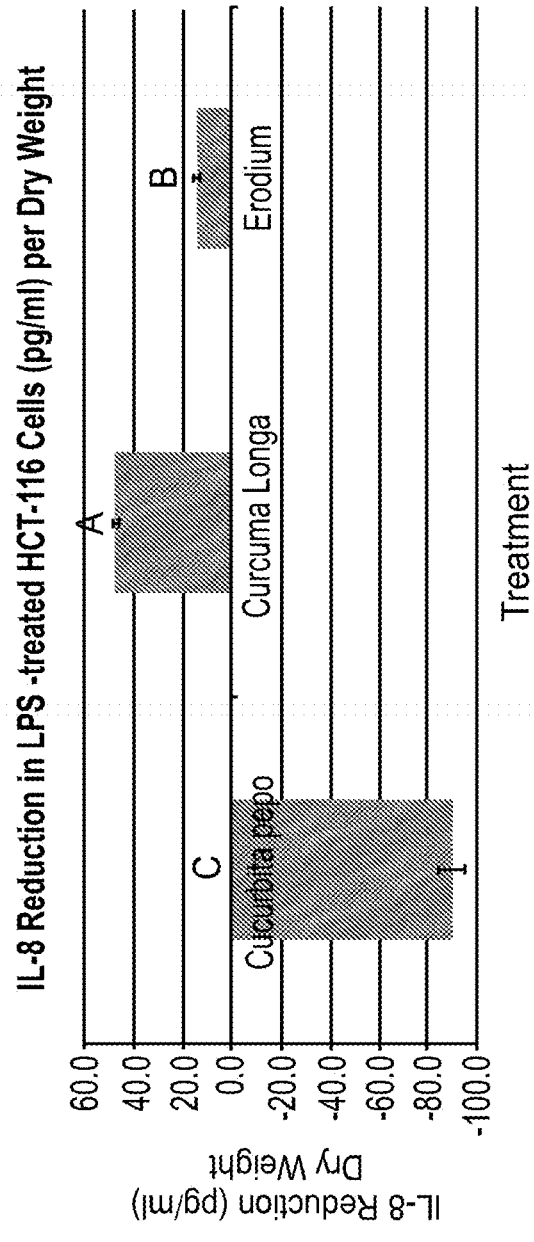
Figure 13A:
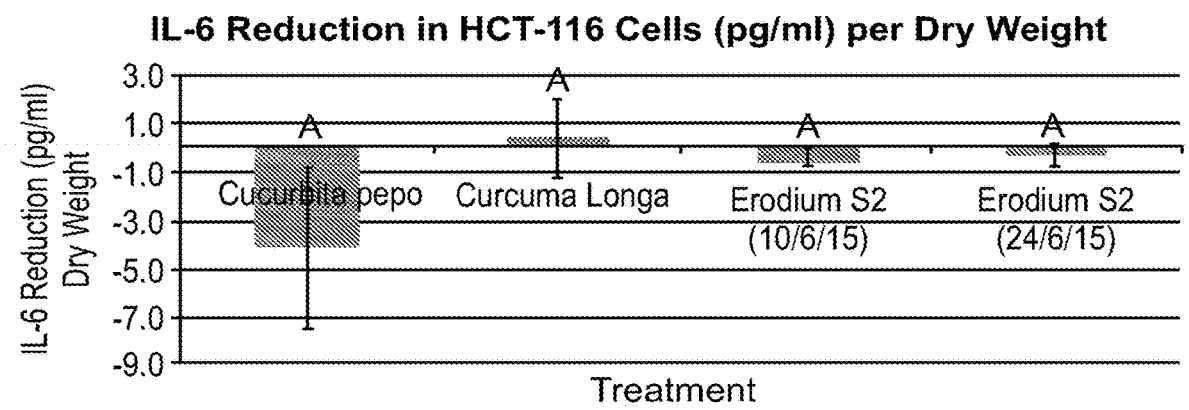
FIGS. 13A-13D include graphs showing the effect of *Erodium* water extracts on expression of IL-6, Il-12 and IL-27 in TNF-α stimulated HCT-116 cultured colon cells.
Figure 13B:
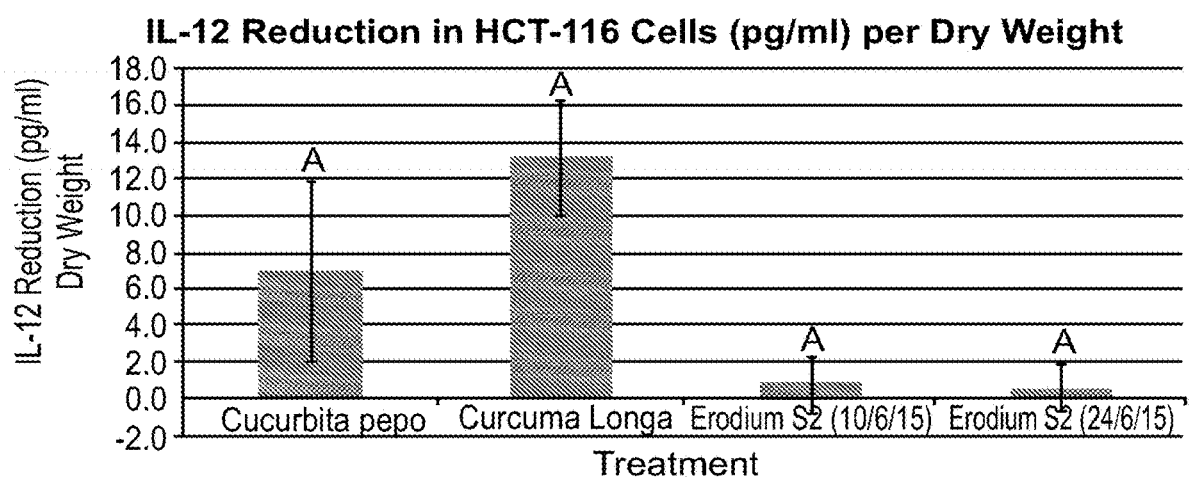
Figure 13C:
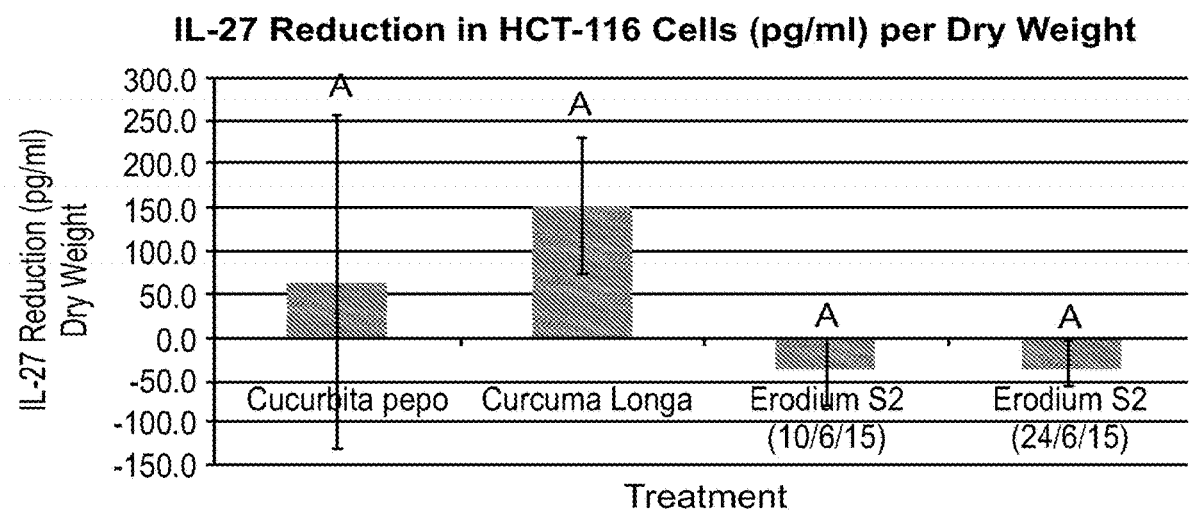
Figure 13D:
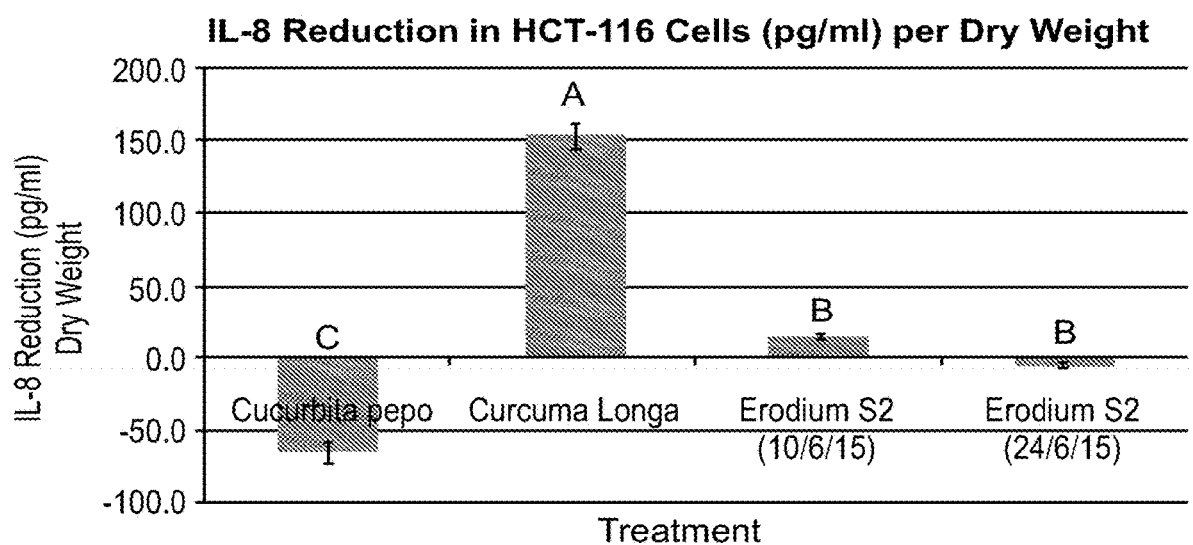
Figure 14A:
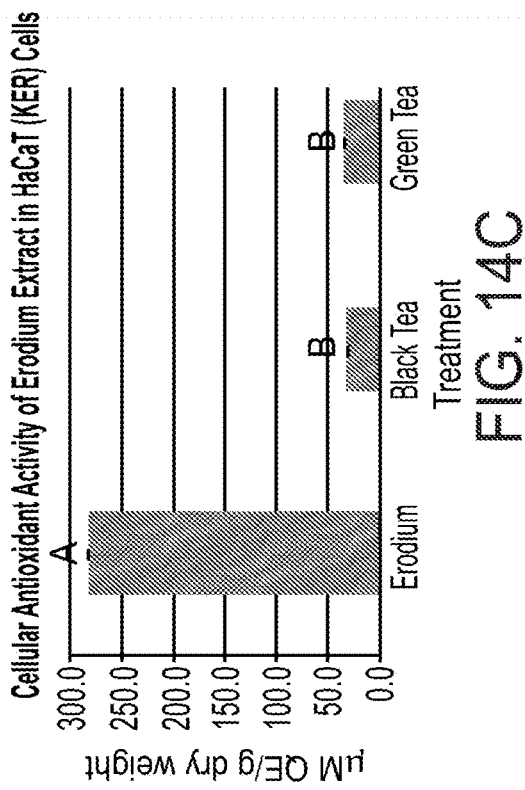
Figure 14B:
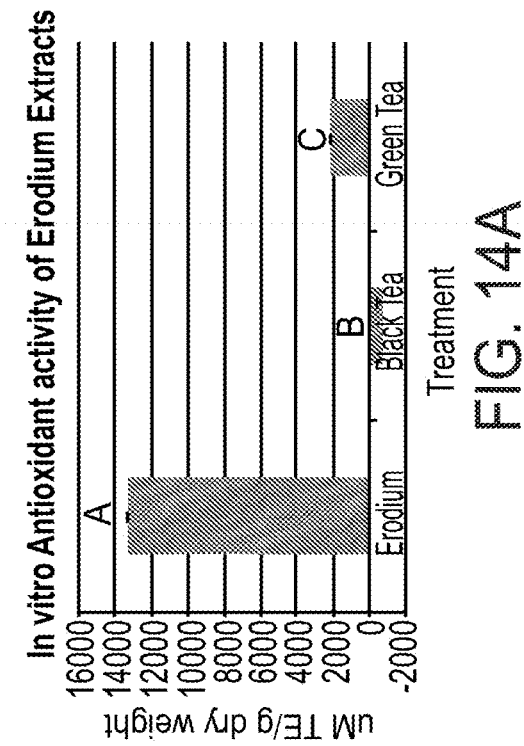
Figure 14C:
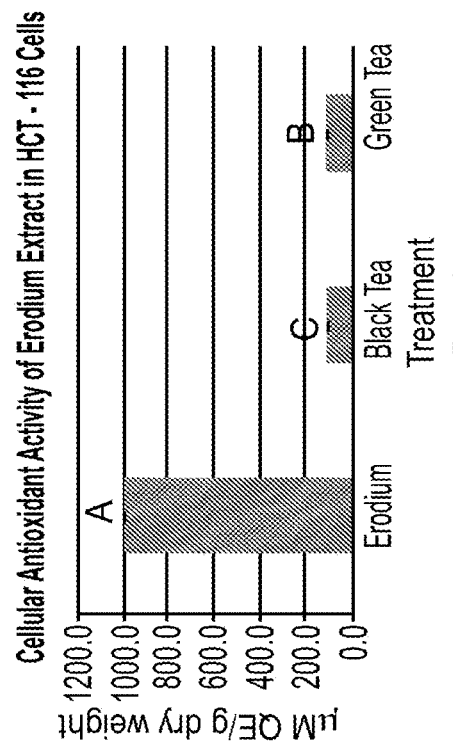
Figure 14D:
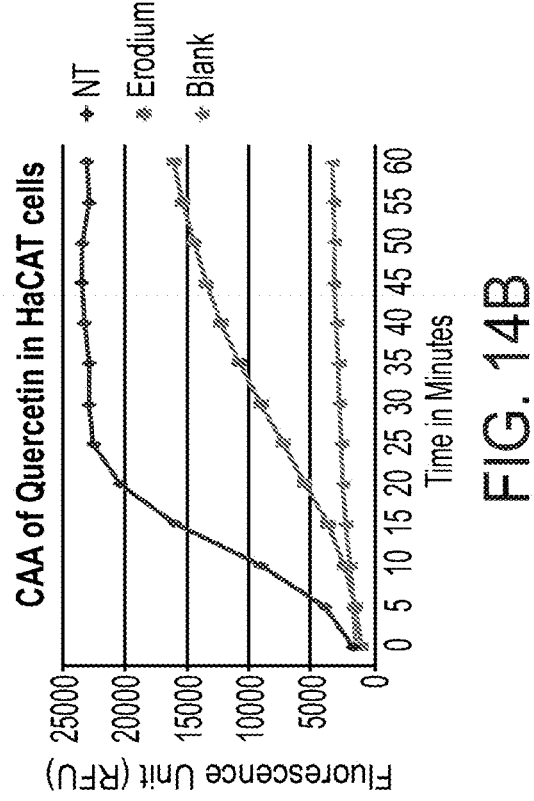

TNF-α is located upstream the cascade event and is known to initiate IL-8 expression. TNF-α expression is reported to be short and transient. Although the values obtain for TNF-α are not significantly different the highest expression is observed after a short period (1 hr). On the other hand, IL-8 that is located downstream the cascade, reached the highest values after 24 hr (FIG. 12A). Therefore, the influence of *Erodium* water extract on LPS-triggered inflammation was evaluated 24 hours after LPS-excitation. The results clearly show that this extract alleviates inflammation by reducing IL-8 levels (FIG. 12B).

Example 8

The Effect of *Erodium* Water Extract on Additional ILs Tested

The purpose of this set of experiments was to test whether the levels of other inflammation-related cytokines, IL-6, IL-12 and IL-27, are affected when treating the cells with *Erodium* extract (FIGS. 13A-13D). The procedures were similar to those applied for IL-8 and similar ELISA kits from the manufacturer were used to detect these ILs. IL-8 assay was used as a control to verify the system was working.

A standard curve (not shown) was obtained for all the ILs tested. IL-6, IL-12, and IL-27 all showed basal OD reads implying that these cytokines were not induced upon TNF-α treatment.

Example 9

Antioxidant Activity of *Erodium crassifolium* Extracts

Oxidative stress is a result of an imbalance between reactive oxygen metabolites (ROM) production and neutralizing capacity of antioxidant mechanisms. Oxidative damage of lipids and other macromolecules such as DNA and RNA results in alteration of cell membranes and other cellular components. Evidence is accumulating that oxidative stress is involved in many pathological processes, including: rheumatoid arthritis, asthma, cancer, macular degeneration, inflammatory Bowel Disease (IBD), neurodegenerative diseases such as Parkinson's and Alzheimer diseases, arthritis, diabetes mellitus, atherosclerosis and chronic fatigue syndrome.

The antioxidant assays reveal a high antioxidant activity derived from *Erodium* water extracts (FIGS. 14A-14D). Furthermore, this activity was shown to be higher than that found in green and black teas that are known for their antioxidant activity. The combination of both anti-inflammation and antioxidant activities in the same *Erodium* extract is of great importance for development of future products based on this plant extracts.

Example 10

Anti-UV and Hydrogen Peroxide Induced Inflammation Activity of *Erodium crassifolium* Extracts In the last two decades the effect of polluted air or water on human diseases is of high interest. The skin, as the body's main barrier is a target organ for pollution and also the site of significant absorption of environmental pollutants. Some diseases such as allergies and cancer are affected by pollutants such as UV radiation, hydrogen peroxide (or other ROS generators) and arsenic molecules in water and crops.

The anti-pollutant activity of *Erodium* water extracts was tested in HaCaT (KER) skin cells. These cells were UVC-treated or exposed to $H_2O_2$ in the presence or absence of *Erodium* water extracts. The anti-pollutant activity was determined by the IL-8 ELISA assay described previously.

As shown in FIGS. 15A-15B, HaCaT (KER) skin cells exposed to either UVC or hydrogen peroxide ($H_2O_2$) in the presence of *Erodium* water extracts revealed lower level of IL-8 compared to the untreated control cells. These results suggest that *Erodium* water extracts protect the cells also from pollutants as UVC and $H_2O_2$. The combination of anti-inflammation, antioxidant and anti-pollutant activities in the same *Erodium* extract is of great importance and makes this extract a powerful candidate for development of future products food supplements, cosmetic, derma-cosmetic and skin beauty products based on this plant.

Example 11

Treatment with *Erodium* Water Extracts Reduces Expression of Matrix Metalloproteinase-9

Matrix metalloproteinase-9 (MMP-9), a member of the matrix metalloproteinase family that degrades collagen IV and processes chemokines and cytokines, participates in epidermal remodeling in response to stress and injury. Limited activity of MMP-9 is essential while excessive activity is deleterious to the healing process. Tumor necrosis factor (TNF-α,), a key mediator of cutaneous inflammation, is a powerful inducer of MMP-9. In order to evaluate whether *Erodium* water extracts effected expression of MMP-9, mRNA was purified from TNF-α-stimulated HaCaT cells in the presence and absence of *Erodium* water extracts. The expression of MMP-9 was normalized to the expression of GAPDH mRNA and measured by q-RT-PCR.

As illustrated in FIG. 16, treatment of HaCaT (KER) skin cells with *Erodium* water extract at both concentrations used, reduced the expression levels of MMP-9 mRNA.

Example 12

Chemical Characterization of *Erodium crassifolium* Extract

*Erodium crassifolium* water extract was subjected to HPLC fractionation as described in material and methods.

Retention time and area of the peaks detected from HPLC chromatogram illustrated in FIG. 17 of *Erodium* water extract are summarized in Table 2 below. Asterisk indicates the major peaks showing biological activity (anti-inflammatory activity) as detected by IL-8 ELISA assay.

TABLE 2

| Sample No. | Ret. Time Min | Area mAU*min (220 nm) | Area mAU*min (240 nm) | Area mAU*min (280 nm) | Fractions |
|---|---|---|---|---|---|
| 1 | 2.74 | 103.742 | 16.722 | 4.511 | Fraction 1 |
| 2 | 3.45 | 122.537 | 23.163 | 1.071 | Fraction 2 |
| 3 | 3.75 | — | 0.224 | 1.185 | |
| 4 | 4.19 | 30.589 | 0.92 | 0.989 | |
| 5 | 4.85 | 15.445 | 0.585 | 3.752 | |
| 6 | 5.12 | 2.454 | 0.407 | — | |
| 7 | 5.79 | 5.283 | 1.024 | 1.49 | |
| 8 | 6.23 | 2.546 | 0.692 | — | Fraction 3 |
| 9 | 6.61 | 18.282 | 2.138 | 6.061 | |
| 10 | 8.45 | 1.85 | 3.413 | 0.183 | |
| 11* | 10.11 | 60.664 | 18.669 | 2.522 | Fraction 4 |
| 12* | 13.66 | 56.35 | 2.864 | 9.961 | Fraction 5 |
| 13 | 16.71 | 16.643 | 5.014 | — | Fraction 6 |
| 14 | 18.2 | 5.27 | 1.389 | 0.605 | Fraction 7 |
| 15 | 19.02 | 2.682 | 0.874 | 0.197 | |
| 16 | 20.4 | 5.276 | 1.768 | — | |
| 17* | 20.84 | 33.37 | 9.047 | 6.955 | Fraction 8 |

TABLE 2-continued

| Sample No. | Ret. Time Min | Area mAU*min (220 nm) | Area mAU*min (240 nm) | Area mAU*min (280 nm) | Fractions |
|---|---|---|---|---|---|
| 18 | 22.39 | 2.5 | 0.547 | 1.696 | |
| 19 | 23.05 | 8.683 | 2.192 | 1.22 | |
| 20 | 25.47 | 3.274 | 0.858 | 0.321 | Fraction 9 |
| 21* | 26.52 | 40.509 | 9.635 | 8.86 | |
| 22 | 36.05 | — | 1.61 | 0.74 | Fraction 13 |

As shown in Table 2, 13 fractions were obtained that revealed 23 peaks. The amount of IL-8 was analyzed in each peak by ELISA (FIG. 17).

The retention time and area of the peaks detected from HPLC chromatogram of non-hydrolyzed *Erodium* water extract vs. the hydrolyzed one at 240 nm is summarized in Table 3, herein below.

TABLE 3

| Sample No. | Ret. Time Min | Erodium (normal) Area mAU*min (240 nm) | Erodium (hydrolyzed) Area mAU*min (240 nm) |
|---|---|---|---|
| 1 | 2.74 | 16.722 | 175.85 |
| 2 | 3.45 | 23.163 | 29.318 |
| 3 | 3.75 | 0.224 | 18.602 |
| 4 | 4.19 | 0.92 | — |
| 5 | 4.85 | 0.585 | 5.37 |
| 6 | 5.12 | 0.407 | — |
| 7 | 5.79 | 1.024 | 1.73 |
| 8 | 6.23 | 0.692 | 5.24 |
| 9 | 6.61 | 2.138 | 6.62 |
| 10 | 7.79 | — | 0.654 |
| 11 | 8.45 | 3.413 | 4.484 |
| 12* | 10.11 | 18.669 | 106.856 |
| 13 | 13.66 | 2.864 | 0.4 |
| 14 | 16.71 | 5.014 | 14.108 |
| 15 | 18.2 | 1.389 | 1.286 |
| 16 | 19.02 | 0.874 | — |
| 17 | 20.4 | 1.768 | — |
| 18 | 20.84 | 9.047 | — |
| 19 | 22.39 | 0.547 | — |
| 20 | 23.05 | 2.192 | — |
| 21 | 25.47 | 0.858 | — |
| 22 | 26.52 | 9.635 | — |
| 23 | 36.05 | 1.61 | — |
| 24 | 38.43 | 0.393 | — |

As illustrated in FIG. 17, at least 4 fractions (Fractions 4, 5, 8, and 9) harbor biological activity.

Example 13

Ethanol Extract of *E. crassifolium* Tubers Reduce IL-8 Levels

A 70% ethanol extract of *E. crassifolium* tubers (EE) was analyzed for its effect on IL-8 levels in a HaCaT human skin cell line. HPLC chromatogram of the extract was obtained and fractionated to 11 fractions (F1-F 11; FIG. 18A).

IL-8 was used as a marker for inflammation in TNF-α treated cells; TNF-α treatment was used to increase the IL-8 levels in the skin cells. The EE at a concentration of 600 µg/mL significantly reduced the level of IL-8 (61.2±7 µg/ml IL-8; 34.9% of TNF-α activated cells; FIG. 18B), in comparison to TNF-α activated and non-treated cells.

Dexamethasone, an anti-inflammatory glucocorticoid used to treat skin inflammation was used as a positive control. The activity of the extract was greater than that of 100 µM dexamethasone (104.0±3.0 pg/mL IL-8; 59.4% of TNF-α activated cells; FIG. 18B).

Among the fractions (F1-F11) derived from the EE (600 µg/mL), F4 and F3 were the most active fractions (62.3±4.4 and 72.0±1.1 pg/mL IL-8; 35.6% and 41.2% of TNFα activated cells, respectively), and retained the level of reduction of IL-8 level of the EE and the fraction pool (PF; all fractions pooled together; 58.7±5.7 pg/ml IL-8; 33.3% of TNF-α activated cells; FIG. 1B).

Example 14

Fractions 3 and 4 of Ethanol Extracted *E. crassifolium* Tubers Show Antioxidant Activity The EE at a concentration of 60 mg/mL was found to have significant anti-oxidant activity (64.0±6.1 TE mM/g dry weight) in the ORAC assay (FIG. 19). This activity was 53% of the green tea infusion at the concentration of 25 mg/mL, which had 119.7±5.2 TE mM/g dry weight. The dose-dependent effect of the EE at descending concentrations was bell-shaped, reaching the maximum activity at a concentration of 6 mg/mL (75.2±0.7 TE mM/g dry weight; FIG. 19). Both fractions F3 and F4 were active at their highest concentration (62.2±4.8 and 66.5±7.9 TE mM/g dry weight, respectively) similarly to the EE, however with a dose-dependent, linear trend (FIG. 19).

Example 15

Ethanol Extract of *E. crassifolium* Tubers and Fractions 3 and 4 Reduce IL-8 Levels in Cells Exposed to UVB Light The ability of the EE and fractions to reduce UVB-induced IL-8 levels in HaCaT was examined following UVB exposure for 2 and 3 min. UVB exposure led to increased IL-8 levels in the cells (up to 19.2 pg/mL IL-8 following 3 min of exposure). Treatment with the EE at a concentration of 600 µg/mL significantly reduced IL-8 levels induced by UVB following both 2 and 3 min of exposure (1.7 pg/mL IL-8 and 1.8 pg/mL IL-8, respectively; FIG. 20). F4 was less effective than the EE, with significant reduction of IL-8 levels only following 3 min of exposure (9.6 pg/mL IL-8), whereas treatment with F3 did not reduce the UVB-induced IL-8 level (FIG. 20).

Example 16

(−)-Epigallocatechin is the Main Compound in Fraction 4 of the Ethanol Extract of *E. crassifolium* Tubers Identification of the active compounds in F4 was performed by using GC/MS following derivatization with BSTFA and 1% TMCS (Table 3 and FIG. 21A). (−)-Epigallocatechin (EGC) formed 41.5% of the extract. Mannofuranose constituted 17.2% of the extract. while cis- and trans-catechin were each around 12%. and gallic acid was present at an amount of 5.7%. Several other compounds were present in minor concentrations (Table 4 and FIG. 21A).

TABLE 4

Compounds identified by GC/MS from fraction 4 of 70% ethanol extract of E. crassifolium tubers. RT, retention time.

| Compound | Retention time (min) | Percentage (%) from total amount |
|---|---|---|
| mannofuranose | 28.024 | 17.2 |
| α-D-xylopyranose | 29.047 | 2.7 |
| gallic acid | 29.766 | 5.7 |
| palmitic acid | 30.853 | 6.4 |
| stearic acid | 33.831 | 2.0 |
| trans-catechin | 42.166 | 11.7 |
| cis-catechin | 42.435 | 12.8 |
| epigallocatechin | 43.007 | 41.5 |

Example 17

Fraction 4 of the Ethanol Extract of E. crassifolium Tubers is Highly Potent if Reducing IL-8 Levels in Cells To further examine whether EGC is one of the compounds that causes F4's in vitro anti-inflammatory activity, the inventors further fractioned F4 to sub-fractions using preparative HPLC to purify the F4 sub-fraction that contains mainly EGC (F4-6; FIG. 24). GC/MS analysis showed that F4-6 contained mostly EGC (87.2%) with relative low concentrations of gallic acid (1.5%) and other residual compounds (Table 5 and FIG. 21B).

TABLE 5

Compounds identified by GC/MS from fraction 4-6, which is sub-fraction of fraction 4 of 70% ethanol extract of E. crassifolium tubers. RT, retention time.

| Compound | RT (min) | Percentage % from total amount |
|---|---|---|
| mannofuranose | 28.024 | 3.6 |
| α-D-xylopyranose | 29.047 | 1.4 |
| gallic acid | 29.766 | 1.5 |
| palmitic acid | 30.853 | 5.1 |
| stearic acid | 33.831 | 1.2 |
| epigallocatechin | 43.007 | 87.2 |

The inventors next examined the reduction in IL-8 levels induced by TNF-α in HaCaT cells following treatment with F4, F4-6 and pure standard of EGC at different concentrations (FIG. 22A). F4 showed the highest and dose-dependent activity compared to F4-6 and purified EGC, when examined in equivalent EGC absolute concentrations. Notably, F4 showed anti-inflammation activity also at 2.2 µg/mL of EGC equivalence which is lower than its $IC_{50}$ (FIG. 22A and FIG. 25).

None of the examined concentrations of pure standard EGC showed any significant IL-8 reduction activity. On the contrary, the concentration of 17.6 µg/mL of EGC even led to increased IL-8 levels.

Example 18

Combination of (−)-Epigallocatechin, Catechin and Gallic Acid Present in F4 Effectively Reduce IL-8 Levels in Cells Following, the combination of the other major compounds found in F4, catechin and gallic acid, were tested for levels of IL-8 in HaCaT cells together with EGC at the proportion of concentrations found in F4 from the GC/MS analysis (Table 4) and at the quantified concentration of EGC found in F4 by HPLC analysis (FIG. 24). For example, combination 1 (comb-1; FIG. 22B) was taken at an EGC concentration of 50 µg/mL (HPLC analysis; FIG. 24), 30 µg/mL and 7 µg/mL of catechin and gallic acid, respectively (Table 4). Comb-1 was serially diluted, such that the most diluted sample, combination 6 (comb-6) contained 1.56 µg/mL of EGC, 0.94 µg/mL of catechin and 0.22 µg/mL of gallic acid. From the tested combinations, only combination 1 showed significant anti-inflammatory activity on HaCaT cells. When diluted, the combination was no longer active. In addition, the individual pure compounds (i.e., EGC, catechin and gallic acid), were inactive for reduction of IL-8 levels in HaCaT cells once tested separately at the concentration present in comb-1.

Example 19

Fraction 4 of the Ethanol Extract of E. crassifolium Reduces MMP3 and MMP9 Expression in Cells The effect of treatment with F4 on the expression of MMP3 and MMP9 in HaCaT cells was performed at $IC_{50}$ concentration of F4, determined based to be 3.0 µg/mL EGC on the absolute EGC content of F4 (FIG. 25). Expression of both MMP3 and MMP9 was significantly induced by TNF-α (to 4.5±0.5 and 2.0±0.2 the amount of non-treated cells, respectively) and reduced by F4 (to 2.7±0.4 and 0.8±0.4 the amount that of non-treated cells, respectively; FIG. 23).

DISCUSSION

Here the inventors present in vitro indications for anti-inflammatory activity of the ethanol extract of E. crassifolium tubers on HaCaT normal keratinocyte cell line. The inventors also demonstrated that the different compounds detected in the EE interact to convey the reduction in IL-8 levels.

The inventors found the EE to reduce IL-8 levels induced by TNF-α. The inventors next sought to examine the effect of the EE and active fractions (F3 and F4) on inflammation that was induced in these skin cells by UVB light, an abundant natural inducer. Both acute and long-term exposure to UVB radiation causes inflammation and may induce skin cancer. UVB exposure also leads to TNF-α and IL-8 upregulation in the epidermis of normal human skin. The inventors found that the EE and to a lesser extent F4, but not F3, had a significant impact against UVB-induced inflammation in skin cells. The fact that the EE is more active than its separated fractions under similar conditions may suggest that additional compounds or relative concentrations present in the EE, and not in F4, enhanced IL-8 levels reduction. F4 also reduced MMP3 and MMP9 gene expression. Since MMP3 and MMP9 expression is a biomarker for skin inflammation, these results further validate the suggested anti-inflammatory activity of the E. crassifolium tubers extract.

F4 isolated from the EE was found to contain relative high concentrations of EGC, a polyphenol. Plant-derived polyphenols contain aromatic ring(s) bearing one or more hydroxyl group(s) are found in many consumed food plants such as tea, cocoa, grape, apple, blueberry, peach and orange. Polyphenols have been proposed to have many health benefits, including lessening diabetes, providing anti-cancer, anti-allergenic, anti-artherogenic, anti-inflammatory, and anti-microbial activities, as well as playing a cardioprotective role. Multiple previous studies have shown, in both in vitro and in vivo models, that tea polyphenols are effective scavengers of reactive oxygen species and may function as anti-oxidants [20]. In this study the inventors showed by an in vitro assay that the EE and fractions (F3 and F4) have anti-oxidative effects, although lower than those of green tea.

More specifically, EGC is part of a large group of catechins that have many health benefits. For example, green tea (*Camellia sinensis*) extracts, which have a long history of safe and beneficial human consumption contain the polyphenols (−)-epigallocatechin gallate (EGCG) as the most abundant compound, followed by (−)-epicatechin gallate (ECG), (−)-epigallocatechin (EGC), (−)-epicatechin and (−)-catechin. All these compounds from green tea, except for catechin, reduced IL-8 production in human nasal fibroblasts and A549 epithelial cells. The inventors therefore sought to determine whether EGC is one of the anti-inflammatory active molecules in the EE.

The inventors found that the commercial standard EGC had lower ability to reduce IL-8 levels in cells in comparison to F4. These results suggest that additional compounds in F4 may confer EGC with better activity. Other compounds found in F4 include gallic acid, trans-catechin and cis-catechin, along with palmitic acid and stearic acid. In addition, when trans- and cis-catechins were removed from the active fraction (as in F4-6), activity was reduced. It is, therefore, possible that although purified catechin is not active on its own, the presence of trans- and cis-catechins is needed to enhance EGC and gallic acid anti-inflammatory activity. Indeed, activity of a combination of EGC, gallic acid and catechin at similar relative amounts and concentrations as found in F4 was higher than that of the individual compounds. A similar trend of increased anti-oxidant activity of a combination of these compounds present in total extracts made from grape seeds and skins or green or Labrador tea was reported previously. However, the EE and F4 activity was still higher than that of the combination produced from pure compounds, suggesting that additional compounds are present in the plant and contribute to its high overall anti-inflammatory activity.

The inventors have shown that an ethanol extract of *E. crassifolium*, a plant used in folk-medicine plant, has substantial in vitro anti-inflammatory and anti-oxidative activities. EGC and additional phenolic compounds are suggested to be some of the active compounds in this extract, whereas certain combinations of these compounds present in the plant extract led to increased activity. The anti-oxidative activity of the EE and its ability to suppress UVB-induced increase in IL-8 level suggest it to be a noteworthy candidate for inclusion in products for skin treatment and protection.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A composition consisting essentially of a therapeutically effective amount of: epigallocatechin, mannofuranose, α-D-xylopyranose, gallic acid, palmitic acid, stearic acid, trans-catechin, cis-catechin, and a pharmaceutically or a nutraceutically acceptable carrier, wherein said composition being formulated for topical or oral administration, and wherein composition is characterized by an anti-inflammatory activity, an antioxidant activity, or both.

2. The composition of claim 1, wherein epigallocatechin is present in an amount of 35-50% (w/w) of said composition.

3. The composition of claim 1, wherein mannofuranose is present in an amount of 15-22% (w/w) of said composition.

4. The composition of claim 1, wherein α-D-xylopyranose is present in an amount of 1.5-3.5% (w/w) of said composition.

5. The composition of claim 1, wherein gallic acid is present in an amount of 3-7% (w/w) of said composition.

6. The composition of claim 1, wherein palmitic acid is present in an amount of 4-8% (w/w) of said composition.

7. The composition of claim 1, wherein stearic acid is present in an amount of 0.5-3.5% (w/w) of said composition.

8. The composition of claim 1, wherein trans-catechin is present in an amount of 8-15% (w/w) of said composition.

9. The composition of claim 1, wherein cis-catechin is present in an amount of 7-16% (w/w) of said composition.

10. The composition of claim 1, wherein any one of said: epigallocatechin, mannofuranose, α-D-xylopyranose, gallic acid, palmitic acid, stearic acid, trans-catechin, and cis-catechin, is derived from a polar extract of *Erodium* plant tuber.

11. The composition of claim 10, wherein said polar solvent comprises 50-90% (v/v) ethanol.

12. The composition of claim 1, wherein said *Erodium* plant is *Erodium crassifolium* L'Her.

13. The composition of claim 1, being a pharmaceutical composition or a nutraceutical composition.

14. The composition of claim 1, being in the form of: (i) a gel, a cream, an ointment, a paste, or a lotion; or (ii) a tablet.

15. A method for treating a subject afflicted with an inflammatory or a condition associated therewith, comprising administering to said subject a therapeutically effective amount of the composition of claim 1, wherein said administering is topically, orally, or both.

16. The method of claim 15, wherein said inflammatory disease comprises an inflammatory skin disease.

17. The method of claim 16, wherein said skin disease is selected from the group consisting of: a cutaneous disease, a dermal disease, a bullous skin disease, *Pemphigus vulgaris*, Bullous pemphigoid, *Pemphigus foliaceus*, and any combination thereof.

18. The method of claim 15, wherein said inflammatory disease is induced by irradiation, oxidative stress, or both.

19. The method of claim 15, wherein said treating comprises reducing the expression level, the activity, or both, of interleukin 8 (IL-8), matrix metalloprotease 3 (MMP3), MMP9, or any combination thereof, in said subject.

20. A composition consisting essentially of: epigallocatechin in an amount of 35-50% (w/w) of said composition, mannofuranose in an amount of 15-22% (w/w) of said composition, α-D-xylopyranose in an amount of 1.5-3.5% (w/w) of said composition, gallic acid in an amount of 3-7% (w/w) of said composition, palmitic acid in an amount of 4-8% (w/w) of said composition, stearic acid in an amount of 0.5-3.5% (w/w) of said composition, trans-catechin in an amount of 8-15% (w/w) of said composition, cis-catechin in an amount of 7-16% (w/w) of said composition, and a pharmaceutically or a nutraceutically acceptable carrier, being formulated for oral or topical administration, and wherein said composition is characterized by an anti-inflammatory activity, an antioxidant activity, or both.

21. The composition of claim 20, being in the form of: (i) a gel, a cream, an ointment, a paste, or a lotion; or (ii) a tablet.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ttgacagcga caagaagtgg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tcacgtcgtc cttatgcaag                                               20

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
gcagtttgct cagcctatc                                                19

<210> SEQ ID NO 4
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 4
tcacctccaa tccaaggaac                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cagcctcaag atcatcagca                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tgtggtcatg agtccttcca                                          20
```